United States Patent
Alexander et al.

(10) Patent No.: US 9,815,797 B2
(45) Date of Patent: Nov. 14, 2017

(54) FUSED BICYCLIC HETEROAROMATIC DERIVATIVES AS MODULATORS OF TNF ACTIVITY

(71) Applicant: UCB BIOPHARMA SPRL, Brussels (BE)

(72) Inventors: Rikki Peter Alexander, Slough (GB); Gregory Foulkes, Abingdon (GB); Martin Clive Hutchings, Slough (GB); Victoria Elizabeth Jackson, Slough (GB); Boris Kroeplien, Slough (GB); James Thomas Reuberson, Slough (GB); Sarah Margaret Rook, Abingdon (GB); Zhaoning Zhu, Slough (GB)

(73) Assignee: UCB Biopharma SPRL, Brussels (BE)

( * ) Notice: Subject to any disclaimer, the term of this patent is extended or adjusted under 35 U.S.C. 154(b) by 0 days.

(21) Appl. No.: 15/101,283

(22) PCT Filed: Dec. 8, 2014

(86) PCT No.: PCT/EP2014/076877
§ 371 (c)(1),
(2) Date: Jun. 2, 2016

(87) PCT Pub. No.: WO2015/086523
PCT Pub. Date: Jun. 18, 2015

(65) Prior Publication Data
US 2016/0304470 A1    Oct. 20, 2016

(30) Foreign Application Priority Data

Dec. 9, 2013  (GB) .................................. 1321752.6
May 23, 2014  (GB) .................................. 1409244.9

(51) Int. Cl.
| | | |
|---|---|---|
| *C07D 239/74* | (2006.01) |
| *A61K 31/47* | (2006.01) |
| *A61K 31/472* | (2006.01) |
| *A61K 31/498* | (2006.01) |
| *A61K 31/506* | (2006.01) |
| *A61K 31/517* | (2006.01) |
| *C07D 215/14* | (2006.01) |
| *C07D 237/28* | (2006.01) |
| *A61K 31/502* | (2006.01) |
| *C07D 215/06* | (2006.01) |
| *C07D 237/32* | (2006.01) |
| *C07D 241/44* | (2006.01) |
| *A61K 45/06* | (2006.01) |
| *C07D 217/16* | (2006.01) |
| *C07D 241/42* | (2006.01) |
| *C07D 403/04* | (2006.01) |

(52) U.S. Cl.
CPC ............ *C07D 239/74* (2013.01); *A61K 31/47* (2013.01); *A61K 31/472* (2013.01); *A61K 31/498* (2013.01); *A61K 31/502* (2013.01); *A61K 31/506* (2013.01); *A61K 31/517* (2013.01); *A61K 45/06* (2013.01); *C07D 215/06* (2013.01); *C07D 215/14* (2013.01); *C07D 217/16* (2013.01); *C07D 237/28* (2013.01); *C07D 237/32* (2013.01); *C07D 241/42* (2013.01); *C07D 241/44* (2013.01); *C07D 403/04* (2013.01)

(58) Field of Classification Search
CPC .............. A61K 2300/00; A61K 31/472; A61K 31/498; A61K 31/502; A61K 31/517; A61K 31/47; A61K 31/506; A61K 45/06; C07D 215/06; C07D 215/14; C07D 217/16; C07D 237/28; C07D 237/32; C07D 239/74
See application file for complete search history.

(56) References Cited

U.S. PATENT DOCUMENTS 5,869,511 A * 2/1999 Cohan .................... A61K 31/42
                                                514/307

FOREIGN PATENT DOCUMENTS

| EP | 0 399 818 A1 | 11/1990 |
|---|---|---|
| EP | 0 527 534 A1 | 2/1993 |
| EP | 0 567 107 A1 | 10/1993 |
| EP | 1 541 558 A1 | 6/2005 |
| WO | 96/39145 A1 | 12/1996 |
| WO | 00/12497 A2 | 3/2000 |
| WO | 01/38315 A1 | 5/2001 |
| WO | 2007/022946 A1 | 3/2007 |
| WO | 2010/099379 A1 | 9/2010 |
| WO | 2013/186229 A1 | 12/2013 |
| WO | 2014/009295 A1 | 1/2014 |
| WO | 2014/009296 A1 | 1/2014 |

OTHER PUBLICATIONS

Anderson (Chem and Biol 10:787-797, 2003.*
Thiel (Nature Biotechnol 2:513-519, 2004.*
Tansey et al., "The TNF superfamily in 2009: new pathways, new indications, and new drugs", Drug Discovery Today, 2009, 14(23/24), 1082-1088.
Carneiro et al., "Emerging Role for TNF-α in Erectile Dysfunction", J. Sexual Medicine, 2010, vol. 7, 3823-3834.

(Continued)

*Primary Examiner* — Savitha Rao
(74) *Attorney, Agent, or Firm* — McDonnell Boehnen Hulbert & Berghoff LLP

(57) ABSTRACT

A series of substituted heteroaromatic compounds containing two fused six-membered rings, tivity, are accordingly of benefit in the treatment and/or prevention of various human ailments, including autoimmune and inflammatory disorders; neurological and neurodegenerative disorders; pain and nociceptive disorders; cardiovascular disorders; metabolic disorders; ocular disorders; and oncological disorders.

8 Claims, No Drawings

(56) References Cited

OTHER PUBLICATIONS

Wu et al., "Do TNF Inhibitors Reduce the Risk of Myocardial Infarction in Psoriasis Patients?", JAMA, 2013, 309(19), 2043-2044.
Hauwermeiren et al., "Safe TNF-based antitumor therapy following p55TNFR reduction in intestinal epithelium", The Journal of Clinical Investigation, 2013, 123(6), 2590-2603.
Ishikawa et al., "Cyclic Guanidines. IX. Synthesis of 2-Amino-3,4-dihydroquinazolines as Blood Platelet Aggregation Inhibitors", Chemical and Pharmaceutical Bulletin, 1980, 28(5), 1357-1364.

\* cited by examiner

FUSED BICYCLIC HETEROAROMATIC DERIVATIVES AS MODULATORS OF TNF ACTIVITY

This application is the US national phase under 35 U.S.C. §371 of international application PCT/EP2014/076877, filed Dec. 8, 2014, which claims priority to GB application 1321752.6, filed Dec. 9, 2013, and GB 1409244.9, filed May 23, 2014.

The present invention relates to a class of fused bicyclic heteroaromatic derivatives, and to their use in therapy. More particularly, this invention is concerned with pharmacologically active substituted heteroaromatic compounds containing two fused six-membered rings. These compounds are modulators of the signalling of TNFα, and are accordingly of benefit as pharmaceutical agents, especially in the treatment of adverse inflammatory and autoimmune disorders, neurological and neurodegenerative disorders, pain and nociceptive disorders, cardiovascular disorders, metabolic disorders, ocular disorders, and oncological disorders.

TNFα is the prototypical member of the Tumour Necrosis Factor (TNF) superfamily of proteins that share a primary function of regulating cell survival and cell death. One structural feature common to all known members of the TNF superfamily is the formation of trimeric complexes that bind to, and activate, specific TNF superfamily receptors. By way of example, TNFα exists in soluble and transmembrane forms and signals through two receptors, known as TNFR1 and TNFR2, with distinct functional endpoints.

Various products capable of modulating TNFα activity are already commercially available. All are approved for the treatment of inflammatory and autoimmune disorders such as rheumatoid arthritis and Crohn's disease. All currently approved products are macromolecular and act by inhibiting the binding of human TNFα to its receptor. Typical macromolecular TNFα inhibitors include anti-TNFα antibodies; and soluble TNFα receptor fusion proteins. Examples of commercially available anti-TNFα antibodies include fully human antibodies such as adalimumab (Humira®) and golimumab (Simponi®), chimeric antibodies such as infliximab (Remicade®), and pegylated Fab' fragments such as certolizumab pegol (Cimzia®). An example of a commercially available soluble TNFα receptor fusion protein is etanercept (Enbrel®).

TNF superfamily members, including TNFα itself, are implicated in a variety of physiological and pathological functions that are believed to play a part in a range of conditions of significant medical importance (see, for example, M. G. Tansey & D. E. Szymkowski, *Drug Discovery Today*, 2009, 14, 1082-1088; and F. S. Carneiro et al., *J. Sexual Medicine*, 2010, 7, 3823-3834).

The compounds in accordance with the present invention, being potent modulators of human TNFα activity, are therefore beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

In addition, the compounds in accordance with the present invention may be beneficial as pharmacological standards for use in the development of new biological tests and in the search for new pharmacological agents. Thus, in one embodiment, the compounds of this invention may be useful as radioligands in assays for detecting pharmacologically active compounds. In an alternative embodiment, certain compounds of this invention may be useful for coupling to a fluorophore to provide fluorescent conjugates that can be utilised in assays (e.g. a fluorescence polarisation assay) for detecting pharmacologically active compounds.

Co-pending international patent applications WO 2013/186229 (published 19 Dec. 2013), WO 2014/009295 (published 16 Jan. 2014) and WO 2014/009296 (also published 16 Jan. 2014) describe fused imidazole derivatives which are modulators of human TNFα activity.

None of the prior art available to date, however, discloses or suggests the precise structural class of fused bicyclic heteroaromatic derivatives as provided by the present invention.

The compounds in accordance with the present invention potently inhibit the binding of a fluorescence conjugate to TNFα when tested in the fluorescence polarisation assay described herein. Indeed, when tested in that assay, the compounds of the present invention exhibit an $IC_{50}$ value of 50 μM or less, generally of 20 μM or less, usually of 5 μM or less, typically of 1 μM or less, suitably of 500 nM or less, ideally of 100 nM or less, and preferably of 20 nM or less (the skilled person will appreciate that a lower $IC_{50}$ figure denotes a more active compound).

Certain compounds in accordance with the present invention potently neutralise the activity of TNFα in a commercially available HEK-293 derived reporter cell line known as HEK-Blue™ CD40L. This is a stable HEK-293 transfected cell line expressing SEAP (secreted embryonic alkaline phosphatase) under the control of the IFNβ minimal promoter fused to five NF-κB binding sites. Secretion of SEAP by these cells is stimulated in a concentration-dependent manner by TNFα. When tested in the HEK-293 bioassay, also referred to herein as the reporter gene assay, certain compounds of the present invention exhibit an $IC_{50}$ value of 50 μM or less, generally of 20 μM or less, usually of 5 μM or less, typically of 1 μM or less, suitably of 500 nM or less, ideally of 100 nM or less, and preferably of 20 nM or less (as before, the skilled person will appreciate that a lower $IC_{50}$ figure denotes a more active compound).

The present invention provides a compound of formula (I) or an N-oxide thereof, or a pharmaceutically acceptable salt or solvate thereof, or a glucuronide derivative thereof, or a co-crystal thereof:

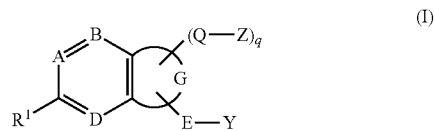

(I)

wherein
q is zero or 1;
A represents C—$R^2$ or N;
B represents C—$R^3$ or N;
D represents C—$R^4$ or N;
G represents the residue of a six-membered heteroaromatic ring selected from pyridinyl, pyridazinyl, pyrimidinyl, pyrazinyl and triazinyl;
E represents a covalent bond; or E represents —O—, —S—, —S(O)—, —S(O)$_2$—, —S(O)(N$R^5$)— or —N($R^5$)—; or E represents an optionally substituted straight or branched $C_{1-4}$ alkylene chain;
Q represents a covalent bond; or Q represents —O—, —S—, —S(O)—, —S(O)$_2$—, —S(O)(N$R^6$)—, —N($R^6$)—, —C(O)N($R^6$)—, —N($R^6$)C(O)—, —S(O)$_2$N($R^6$)— or —N($R^6$)S(O)$_2$—; or Q represents an optionally substituted straight or branched $C_{1-6}$ alkylene chain optionally comprising one, two or three heteroatom-containing linkages independently selected from —O—, —S—, —S(O)—, —S(O)$_2$—, —S(O)(NR$^6$)—, —N(R$^6$)—, —C(O)N(R$^6$)—, —N(R$^6$)C(O)—, —S(O)$_2$N(R$^6$)— and —N(R$^6$)S(O)$_2$—;

Y represents $C_{3-7}$ cycloalkyl, aryl, $C_{3-7}$ heterocycloalkyl or heteroaryl, any of which groups may be optionally substituted by one or more substituents;

Z represents hydrogen, halogen or trifluoromethyl; or Z represents $C_{1-6}$ alkyl, $C_{3-7}$ cycloalkyl, aryl, $C_{3-7}$ heterocycloalkyl, $C_{3-7}$ heterocycloalkenyl or heteroaryl, any of which groups may be optionally substituted by one or more substituents; or Z represents —Z$^1$—Z$^2$ or —Z$^1$—C(O)—Z$^2$, either of which moieties may be optionally substituted by one or more substituents;

Z$^1$ represents a divalent radical derived from an aryl, $C_{3-7}$ heterocycloalkyl or heteroaryl group;

Z$^2$ represents aryl, $C_{3-7}$ heterocycloalkyl, $C_{3-7}$ heterocycloalkenyl or heteroaryl;

R$^1$, R$^2$, R$^3$ and R$^4$ independently represent hydrogen, halogen, cyano, nitro, hydroxy, trifluoromethyl, trifluoromethoxy, —OR$^a$, —SR$^a$, —SOR$^a$, —SO$_2$R$^a$, —SF$_5$, —NR$^b$R$^c$, —NR$^c$COR$^d$, —NR$^c$CO$_2$R$^d$, —NHCONR$^b$R$^c$, —NR$^c$SO$_2$R$^e$, —N(SO$_2$R$^e$)$_2$, —NHSO$_2$NR$^b$R$^c$, —COR$^d$, —CO$_2$R$^d$, —CONR$^b$R$^c$, —CON(OR$^a$)R$^b$, —SO$_2$NR$^b$R$^c$ or —SO(NR$^b$)R$^e$; or $C_{1-6}$ alkyl, $C_{2-6}$ alkenyl, $C_{2-6}$ alkynyl, $C_{3-7}$ cycloalkyl, $C_{4-7}$ cycloalkenyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, $C_{3-7}$ heterocycloalkenyl, $C_{4-9}$ heterobicycloalkyl, heteroaryl, heteroaryl($C_{1-6}$)alkyl, ($C_{3-7}$)heterocycloalkyl($C_{1-6}$)alkyl-aryl-, heteroaryl($C_{3-7}$)heterocycloalkyl-, ($C_{3-7}$)cycloalkyl-heteroaryl-, ($C_{3-7}$)cycloalkyl($C_{1-6}$)alkyl-heteroaryl-, ($C_{4-7}$)cycloalkenyl-heteroaryl-, ($C_{4-9}$)bicycloalkyl-heteroaryl-, ($C_{3-7}$)heterocycloalkyl-heteroaryl-, ($C_{3-7}$)heterocycloalkyl($C_{1-6}$)alkyl-hetero aryl-, ($C_{3-7}$)heterocycloalkenyl-heteroaryl-, ($C_{4-9}$)heterobicycloalkyl-heteroaryl- or ($C_{4-9}$)spiroheterocycloalkyl-heteroaryl-, any of which groups may be optionally substituted by one or more substituents;

R$^5$ and R$^6$ independently represent hydrogen or $C_{1-6}$ alkyl;

R$^a$ represents $C_{1-6}$ alkyl, aryl, aryl($C_{1-6}$)alkyl, heteroaryl or heteroaryl($C_{1-6}$)alkyl, any of which groups may be optionally substituted by one or more substituents;

R$^b$ and R$^c$ independently represent hydrogen or trifluoromethyl; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents; or R$^b$ and R$^c$, when taken together with the nitrogen atom to which they are both attached, represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents;

R$^d$ represents hydrogen; or $C_{1-6}$ alkyl, $C_{3-7}$ cycloalkyl, aryl, $C_{3-7}$ heterocycloalkyl or heteroaryl, any of which groups may be optionally substituted by one or more substituents; and R$^e$ represents $C_{1-6}$ alkyl, aryl or heteroaryl, any of which groups may be optionally substituted by one or more substituents.

The present invention also provides a compound of formula (I) as defined above or an N-oxide thereof, or a pharmaceutically acceptable salt or solvate thereof, or a glucuronide derivative thereof, or a co-crystal thereof, for use in therapy.

The present invention also provides a compound of formula (I) as defined above or an N-oxide thereof, or a pharmaceutically acceptable salt or solvate thereof, or a glucuronide derivative thereof, or a co-crystal thereof, for use in the treatment and/or prevention of disorders for which the administration of a modulator of TNF α function is indicated.

In another aspect, the present invention provides a compound of formula (I) as defined above or an N-oxide thereof, or a pharmaceutically acceptable salt or solvate thereof, or a glucuronide derivative thereof, or a co-crystal thereof, for use in the treatment and/or prevention of an inflammatory or autoimmune disorder, a neurological or neurodegenerative disorder, pain or a nociceptive disorder, a cardiovascular disorder, a metabolic disorder, an ocular disorder, or an oncological disorder.

The present invention also provides a method for the treatment and/or prevention of disorders for which the administration of a modulator of TNFα function is indicated which comprises administering to a patient in need of such treatment an effective amount of a compound of formula (I) as defined above or an N-oxide thereof, or a pharmaceutically acceptable salt or solvate thereof, or a glucuronide derivative thereof, or a co-crystal thereof.

In another aspect, the present invention provides a method for the treatment and/or prevention of an inflammatory or autoimmune disorder, a neurological or neurodegenerative disorder, pain or a nociceptive disorder, a cardiovascular disorder, a metabolic disorder, an ocular disorder, or an oncological disorder, which comprises administering to a patient in need of such treatment an effective amount of a compound of formula (I) as defined above or an N-oxide thereof, or a pharmaceutically acceptable salt or solvate thereof, or a glucuronide derivative thereof, or a co-crystal thereof.

Where any of the groups in the compounds of formula (I) above is stated to be optionally substituted, this group may be unsubstituted, or substituted by one or more substituents. Typically, such groups will be unsubstituted, or substituted by one or two substituents.

For use in medicine, the salts of the compounds of formula (I) will be pharmaceutically acceptable salts. Other salts may, however, be useful in the preparation of the compounds of use in the invention or of their pharmaceutically acceptable salts. Standard principles underlying the selection and preparation of pharmaceutically acceptable salts are described, for example, in *Handbook of Pharmaceutical Salts: Properties, Selection and Use*, ed. P. H. Stahl & C. G. Wermuth, Wiley-VCH, 2002. Suitable pharmaceutically acceptable salts of the compounds of use in this invention include acid addition salts which may, for example, be formed by mixing a solution of the compound of use in the invention with a solution of a pharmaceutically acceptable acid such as hydrochloric acid, sulphuric acid, methanesulphonic acid, fumaric acid, maleic acid, succinic acid, acetic acid, benzoic acid, citric acid, tartaric acid or phosphoric acid. Furthermore, where the compounds of use in the invention carry an acidic moiety, e.g. carboxy, suitable pharmaceutically acceptable salts thereof may include alkali metal salts, e.g. sodium or potassium salts; alkaline earth metal salts, e.g. calcium or magnesium salts; ammonium salts; and salts formed with suitable organic ligands, e.g. quaternary ammonium salts, and meglumine salts.

The present invention includes within its scope solvates of the compounds of formula (I) above. Such solvates may be formed with common organic solvents, e.g. hydrocarbon solvents such as benzene or toluene; chlorinated solvents such as chloroform or dichloromethane; alcoholic solvents such as methanol, ethanol or isopropanol; ethereal solvents such as diethyl ether or tetrahydrofuran; or ester solvents such as ethyl acetate. Alternatively, the solvates of the compounds of formula (I) may be formed with water, in which case they will be hydrates.

The present invention also includes co-crystals within its scope. The technical term "co-crystal" is used to describe the situation where neutral molecular components are present within a crystalline compound in a definite stoichiometric ratio. The preparation of pharmaceutical co-crystals enables modifications to be made to the crystalline form of an active pharmaceutical ingredient, which in turn can alter its physicochemical properties without compromising its intended biological activity (see *Pharmaceutical Salts and Co-crystals*, ed. J. Wouters & L. Quere, RSC Publishing, 2012). Typical examples of co-crystal formers, which may be present in the co-crystal alongside the active pharmaceutical ingredient, include L-ascorbic acid, citric acid, glutaric acid, urea and nicotinamide.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in *Design of Prodrugs*, ed. H. Bundgaard, Elsevier, 1985.

Suitable alkyl groups which may be present on the compounds of use in the invention include straight-chained and branched $C_{1-6}$ alkyl groups, for example $C_{1-4}$ alkyl groups. Typical examples include methyl and ethyl groups, and straight-chained or branched propyl, butyl and pentyl groups. Particular alkyl groups include methyl, ethyl, n-propyl, isopropyl, n-butyl, sec-butyl, isobutyl, tert-butyl, 2,2-dimethylpropyl and 3-methylbutyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

The expression "$C_{1-4}$ alkylene chain" refers to a divalent straight or branched alkylene chain containing 1 to 4 carbon atoms. Typical examples include methylene, ethylene, methylmethylene, ethylmethylene and dimethylmethylene.

Suitable $C_{2-6}$ alkenyl groups include vinyl and allyl.

Suitable $C_{2-6}$ alkynyl groups include ethynyl, propargyl and butynyl.

The term "$C_{3-7}$ cycloalkyl" as used herein refers to monovalent groups of 3 to 7 carbon atoms derived from a saturated monocyclic hydrocarbon, and may comprise benzo-fused analogues thereof. Suitable $C_{3-7}$ cycloalkyl groups include cyclopropyl, cyclobutyl, benzocyclobutenyl, cyclopentyl, indanyl, cyclohexyl and cycloheptyl.

The term "$C_{4-7}$ cycloalkenyl" as used herein refers to monovalent groups of 4 to 7 carbon atoms derived from a partially unsaturated monocyclic hydrocarbon. Suitable $C_{4-7}$ cycloalkenyl groups include cyclobutenyl, cyclopentenyl, cyclohexenyl and cycloheptenyl.

The term "$C_{4-9}$ bicycloalkyl" as used herein refers to monovalent groups of 4 to 9 carbon atoms derived from a saturated bicyclic hydrocarbon. Typical bicycloalkyl groups include bicyclo[3.1.0]hexanyl, bicyclo[4.1.0]heptanyl and bicyclo[2.2.2]octanyl.

The term "aryl" as used herein refers to monovalent carbocyclic aromatic groups derived from a single aromatic ring or multiple condensed aromatic rings. Suitable aryl groups include phenyl and naphthyl, preferably phenyl.

Suitable aryl($C_{1-6}$)alkyl groups include benzyl, phenylethyl, phenylpropyl and naphthylmethyl.

The term "$C_{3-7}$ heterocycloalkyl" as used herein refers to saturated monocyclic rings containing 3 to 7 carbon atoms and at least one heteroatom selected from oxygen, sulphur and nitrogen, and may comprise benzo-fused analogues thereof. Suitable heterocycloalkyl groups include oxetanyl, azetidinyl, tetrahydrofuranyl, dihydrobenzo-furanyl, dihydrobenzothienyl, pyrrolidinyl, indolinyl, isoindolinyl, oxazolidinyl, thiazolidinyl, isothiazolidinyl, imidazolidinyl, tetrahydropyranyl, chromanyl, tetrahydro-thiopyranyl, piperidinyl, 1,2,3,4-tetrahydroquinolinyl, 1,2,3,4-tetrahydroisoquinolinyl, piperazinyl, 1,2,3,4-tetrahydroquinoxalinyl, hexahydro-[1,2,5]thiadiazolo[2,3-a]pyrazinyl, homopiperazinyl, morpholinyl, benzoxazinyl, thiomorpholinyl, azepanyl, oxazepanyl, diazepanyl, thiadiazepanyl and azocanyl.

The term "$C_{3-7}$ heterocycloalkenyl" as used herein refers to monounsaturated or polyunsaturated monocyclic rings containing 3 to 7 carbon atoms and at least one heteroatom selected from oxygen, sulphur and nitrogen, and may comprise benzo-fused analogues thereof. Suitable heterocycloalkenyl groups include thiazolinyl, isothiazolinyl, imidazolinyl, dihydropyranyl, dihydrothiopyranyl and 1,2,3,6-tetrahydropyridinyl.

The term "$C_{4-9}$ heterobicycloalkyl" as used herein corresponds to $C_{4-9}$ bicycloalkyl wherein one or more of the carbon atoms have been replaced by one or more heteroatoms selected from oxygen, sulphur and nitrogen. Typical heterobicycloalkyl groups include 3-azabicyclo[3.1.0]hexanyl, 2-oxa-5-azabicyclo[2.2.1]heptanyl, 6-azabicyclo[3.2.0]heptanyl, 3-azabicyclo[3.1.1]heptanyl, 6-oxa-3-azabicyclo[3.1.1]heptanyl, 3-azabicyclo[4.1.0]-heptanyl, 2-oxabicyclo[2.2.2]octanyl, quinuclidinyl, 2-oxa-5-azabicyclo[2.2.2]octanyl, 3-azabicyclo[3.2.1]octanyl, 8-azabicyclo[3.2.1]octanyl, 3-oxa-8-azabicyclo[3.2.1]octanyl, 3,8-diazabicyclo[3.2.1]octanyl, 3,6-diazabicyclo[3.2.2]nonanyl, 3-oxa-7-azabicyclo-[3.3.1]nonanyl, 3,7-dioxa-9-azabicyclo[3.3.1]nonanyl and 3,9-diazabicyclo[4.2.1]nonanyl.

The term "$C_{4-9}$ spiroheterocycloalkyl" as used herein refers to saturated bicyclic ring systems containing 4 to 9 carbon atoms and at least one heteroatom selected from oxygen, sulphur and nitrogen, in which the two rings are linked by a common atom. Suitable spiroheterocycloalkyl groups include 5-azaspiro[2.3]hexanyl, 5-azaspiro[2.4]heptanyl, 2-azaspiro[3.3]heptanyl, 2-oxa-6-azaspiro[3.3]heptanyl, 3-oxa-6-azaspiro[3.3]-heptanyl, 6-thia-2-azaspiro[3.3]heptanyl, 2-oxa-6-azaspiro[3.4]octanyl, 2-oxa-6-azaspiro-[3.5]nonanyl, 7-oxa-2-azaspiro[3.5]nonanyl, 2-oxa-7-azaspiro[3.5]nonanyl and 2,4,8-triazaspiro[4.5]decanyl.

The term "heteroaryl" as used herein refers to monovalent aromatic groups containing at least 5 atoms derived from a single ring or multiple condensed rings, wherein one or more carbon atoms have been replaced by one or more heteroatoms selected from oxygen, sulphur and nitrogen. Suitable heteroaryl groups include furyl, benzofuryl, dibenzofuryl, thienyl, benzothienyl, thieno[2,3-c]pyrazolyl, thieno[3,4-b][1,4]dioxinyl, dibenzothienyl, pyrrolyl, indolyl, pyrrolo[2,3-b]pyridinyl, pyrrolo[3,2-c]pyridinyl, pyrrolo[3,4-b]pyridinyl, pyrazolyl, pyrazolo[1,5-a]pyridinyl, pyrazolo[3,4-c]pyrimidinyl, indazolyl, 4,5,6,7-tetrahydroindazolyl, oxazolyl, benzoxazolyl, isoxazolyl, thiazolyl, benzothiazolyl, isothiazolyl, imidazolyl, benzimidazolyl, imidazo[2,1-b]thiazolyl, imidazo[1,2-a]pyridinyl, imidazo[4,5-b]pyridinyl, purinyl, imidazo[1,2-a]pyrimidinyl, imidazo[1,2-a]

pyrazinyl, oxadiazolyl, thiadiazolyl, triazolyl, [1,2,4] triazolo[1,5-a]-pyrimidinyl, benzotriazolyl, tetrazolyl, pyridinyl, quinolinyl, isoquinolinyl, naphthyridinyl, pyridazinyl, cinnolinyl, phthalazinyl, pyrimidinyl, quinazolinyl, pyrazinyl, quinoxalinyl, pteridinyl, triazinyl and chromenyl groups.

The term "halogen" as used herein is intended to include fluorine, chlorine, bromine and iodine atoms, typically fluorine, chlorine or bromine.

Where the compounds of formula (I) have one or more asymmetric centres, they may accordingly exist as enantiomers. Where the compounds of use in the invention possess two or more asymmetric centres, they may additionally exist as diastereomers. The invention is to be understood to extend to the use of all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto ($CH_2C=O$) ↔ enol ($CH=CHOH$) tautomers or amide ($NHC=O$) ↔ hydroxyimine ($N=COH$) tautomers. Formula (I) and the formulae depicted hereinafter are intended to represent all individual tautomers and all possible mixtures thereof, unless stated or shown otherwise.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^1H$, $^2H$ (deuterium) or $^3H$ (tritium) atom, preferably $^1H$. Similarly, by way of example, each individual carbon atom present in formula (I), or in the formulae depicted hereinafter, may be present as a $^{12}C$, $^{13}C$ or $^{14}C$ atom, preferably $^{12}C$.

In one aspect, the present invention provides a compound of formula (I) as depicted above or an N-oxide thereof, or a pharmaceutically acceptable salt or solvate thereof, or a glucuronide derivative thereof, or a co-crystal thereof, wherein Q represents —O—, —S—, —S(O)—, —S(O)$_2$—, —S(O)(NR$^6$)—, —N(R$^6$)—, —C(O)N(R$^6$)—, —N(R$^6$)C(O)—, —S(O)$_2$N(R$^6$)— or —N(R$^6$)S(O)$_2$—; or Q represents an optionally substituted straight or branched $C_{1-6}$ alkylene chain optionally comprising one, two or three heteroatom-containing linkages independently selected from —O—, —S—, —S(O)—, —S(O)$_2$—, —S(O)(NR$^6$)—, —N(R$^6$)—, —C(O)N(R$^6$)—, —N(R$^6$)C(O)—, —S(O)$_2$N(R$^6$)— and —N(R$^6$)S(O)$_2$—;

Z represents $C_{3-7}$ cycloalkyl, aryl, $C_{3-7}$ heterocycloalkyl, $C_{3-7}$ heterocycloalkenyl or heteroaryl, any of which groups may be optionally substituted by one or more substituents; or Z represents —Z$^1$—Z$^2$ or —Z$^1$—C(O)—Z$^2$, either of which moieties may be optionally substituted by one or more substituents; and q, A, B, D, G, E, Y, R$^1$, R$^6$, Z$^1$ and Z$^2$ are as defined above.

In another aspect, the present invention provides a compound of formula (I) as depicted above or an N-oxide thereof, or a pharmaceutically acceptable salt or solvate thereof, or a glucuronide derivative thereof, or a co-crystal thereof, wherein R$^1$ represents halogen or cyano; or $C_{1-6}$ alkyl, $C_{2-6}$ alkenyl, $C_{2-6}$ alkynyl, $C_{3-7}$ cycloalkyl, $C_{4-7}$ cycloalkenyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, $C_{3-7}$ heterocycloalkenyl, $C_{4-9}$ heterobicycloalkyl, heteroaryl, heteroaryl($C_{1-6}$)alkyl, ($C_{3-7}$)heterocycloalkyl($C_{1-6}$)alkyl-aryl-, heteroaryl($C_{3-7}$)heterocycloalkyl-, ($C_{3-7}$)cycloalkyl-heteroaryl-, ($C_{3-7}$)cycloalkyl-($C_{1-6}$)alkyl-heteroaryl-, ($C_{4-7}$)cycloalkenyl-heteroaryl-, ($C_{4-9}$)bicycloalkyl-heteroaryl-, ($C_{3-7}$)heterocycloalkyl-heteroaryl-, ($C_{3-7}$)heterocycloalkyl($C_{1-6}$)alkyl-heteroaryl-, ($C_{3-7}$)heterocycloalkenyl-heteroaryl-, ($C_{4-9}$)heterobicycloalkyl-heteroaryl- or ($C_{4-9}$) spiroheterocycloalkyl-heteroaryl-, any of which groups may be optionally substituted by one or more substituents; and q, A, B, D, G, E, Q, Y and Z are as defined above.

In one embodiment, q is zero. In another embodiment, q is 1.

In one embodiment, A represents C—R$^2$. In another embodiment, A represents N.

In one embodiment, B represents C—R$^3$. In another embodiment, B represents N.

In one embodiment, D represents C—R$^4$. In another embodiment, D represents N.

In a first embodiment, A represents C—R$^2$, B represents C—R$^3$ and D represents C—R$^4$.

In a second embodiment, A represents C—R$^2$, B represents C—R$^3$ and D represents N.

In a third embodiment, A represents C—R$^2$, B represents N and D represents C—R$^4$.

In a fourth embodiment, A represents C—R$^2$, B represents N and D represents N.

In a fifth embodiment, A represents N, B represents C—R$^3$ and D represents C—R$^4$.

In a sixth embodiment, A represents N, B represents C—R$^3$ and D represents N.

In a seventh embodiment, A represents N, B represents N and D represents C—R$^4$.

In an eighth embodiment, A represents N, B represents N and D represents N.

Suitably, A represents C—R$^2$, and B and D are as defined above; or A represents N, B represents C—R$^3$, and D is as defined above.

Suitably, A represents C—R$^2$, B represents C—R$^3$ and D is as defined above; or A represents N, B represents C—R$^3$ and D represents C—R$^4$.

Particular sub-classes of compounds in accordance with the present invention include the compounds of formula (IA-A), (IA-B), (IA-C), (IA-D), (IA-E), (IA-F) and (IA-G):

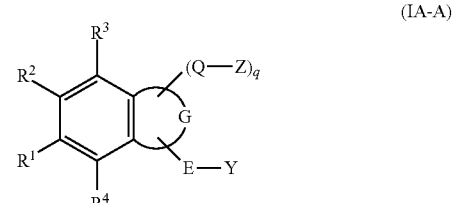

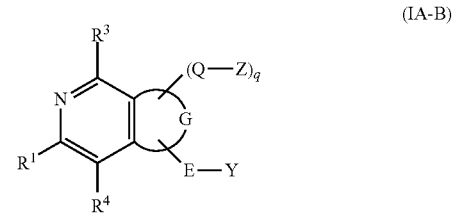

-continued

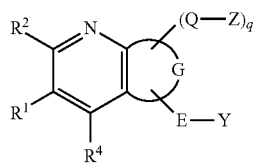
(IA-C)

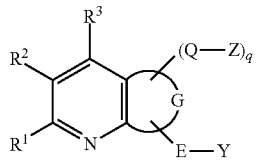
(IA-D)

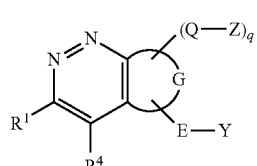
(IA-E)

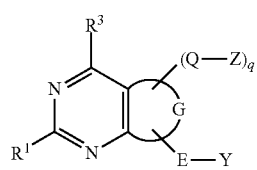
(IA-F)

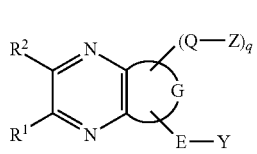
(IA-G)

wherein q, G, E, Q, Y, Z, $R^1$, $R^2$, $R^3$ and $R^4$ are as defined above.

In the compounds of the invention, the moiety G is defined as representing the residue of a six-membered heteroaromatic ring as specified above. From this it is to be understood that the variable G, when taken together with the two carbon atoms of the six-membered ring to which the G-containing ring is fused, represents a six-membered heteroaromatic ring as specified above.

Suitably, the moiety G in the compounds of the invention represents the residue of a six-membered heteroaromatic ring selected from pyridinyl, pyridazinyl, pyrimidinyl and pyrazinyl.

In a first embodiment, the moiety G in the compounds of the invention represents the residue of a pyridine ring.

In a second embodiment, the moiety G in the compounds of the invention represents the residue of a pyridazine ring.

In a third embodiment, the moiety G in the compounds of the invention represents the residue of a pyrimidine ring.

In a fourth embodiment, the moiety G in the compounds of the invention represents the residue of a pyrazine ring.

In a fifth embodiment, the moiety G in the compounds of the invention represents the residue of a triazine ring.

Particular sub-classes of compounds in accordance with the present invention include the compounds of formula (IB-A), (IB-B), (IB-C), (IB-D), (IB-E), (IB-F), (IB-G), (IB-H), (IB-J), (IB-K) and (IIB-L):

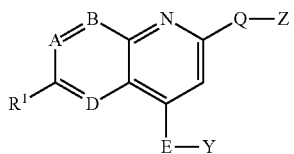
(IB-A)

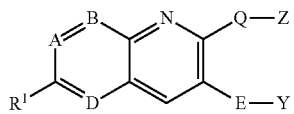
(IB-B)

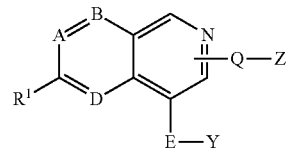
(IB-C)

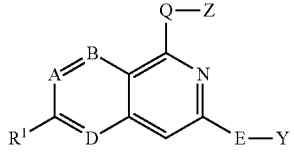
(IB-D)

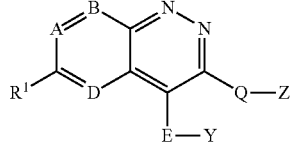
(IB-E)

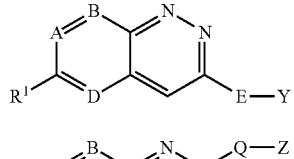
(IB-F)

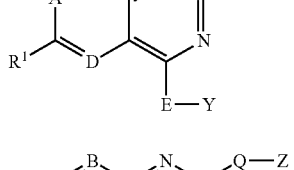
(IB-G)

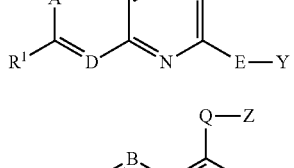
(IB-H)

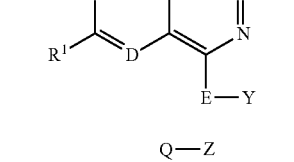
(IB-J)

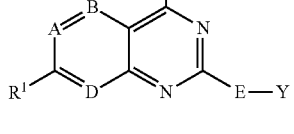
(IB-K)

(IB-L)

wherein

A, B, D, E, Q, Y, Z and $R^1$ are as defined above.

Suitable sub-classes of compounds in accordance with the present invention include the compounds of formula (IB-B), (IB-C), (IB-E), (IB-G) and (IB-H) as depicted above.

Where the compounds in accordance with the invention comprise an optionally substituted straight or branched alkylene chain, typical values thereof include methylene (—CH$_2$—), (methyl)methylene, ethylene (—CH$_2$CH$_2$—), (ethyl)methylene, (dimethyl)-methylene, (methyl)ethylene, propylene (—CH$_2$CH$_2$CH$_2$—), (propyl)methylene and (dimethyl)ethylene, any of which chains may be optionally substituted by one or more substituents. Suitably, such chains are unsubstituted, monosubstituted or disubstituted. Typically, such chains are unsubstituted or monosubstituted. In one embodiment, such chains are unsubstituted. In another embodiment, such chains are monosubstituted. In a further embodiment, such chains are disubstituted.

Examples of typical substituents on the alkylene chain which may be present in a compound in accordance with the invention include halogen, cyano, trifluoromethyl, oxo, hydroxy, $C_{1-6}$ alkoxy, carboxy($C_{1-6}$)alkoxy, trifluoromethoxy, amino, $C_{1-6}$ alkylamino, di($C_{1-6}$)alkylamino, $C_{2-6}$ alkylcarbonylamino, carboxy, benzyloxycarbonyl, tetrazolyl, aminocarbonyl, $C_{1-6}$ alkylaminocarbonyl and di($C_{1-6}$)alkylaminocarbonyl.

Specific examples of suitable substituents on the alkylene chain which may be present in a compound in accordance with the invention include fluoro, cyano, trifluoromethyl, hydroxy, methoxy, carboxymethoxy, amino, acetylamino, carboxy, benzyloxycarbonyl and tetrazolyl.

In a first embodiment, E represents a covalent bond, whereby the integer Y is attached directly to the six-membered ring.

In a second embodiment, E represents —O—, —S—, —S(O)—, —S(O)$_2$—, —S(O)(NR$^5$)— or —N(R$^5$)—. In a first aspect of that embodiment, E represents —O—. In a second aspect of that embodiment, E represents —S—. In a third aspect of that embodiment, E represents —S(O)—. In a fourth aspect of that embodiment, E represents —S(O)$_2$—. In a fifth aspect of that embodiment, E represents —S(O)(NR$^5$)—. In a sixth aspect of that embodiment, E represents —N(R$^5$)—.

In a third embodiment, E represents an optionally substituted straight or branched $C_{1-4}$ alkylene chain. In a first aspect of that embodiment, E represents an optionally substituted methylene (—CH$_2$—) linkage. In a second aspect of that embodiment, E represents an optionally substituted (methyl)methylene linkage. In a third aspect of that embodiment, E represents an optionally substituted (ethyl)methylene linkage.

Generally, E represents a covalent bond; or E represents —N(R$^5$)—; or E represents an optionally substituted straight or branched $C_{1-4}$ alkylene chain.

Typically, E represents —N(R$^5$)—; or E represents an optionally substituted straight or branched $C_{1-4}$ alkylene chain.

Alternatively, E represents —O—; or E represents an optionally substituted straight or branched $C_{1-4}$ alkylene chain.

Suitably, E represents a covalent bond; or E represents —N(R$^5$)—; or E represents methylene (—CH$_2$—), (methyl)methylene or (ethyl)methylene, any of which groups may be optionally substituted by one or more substituents.

Generally, E represents —N(R$^5$)—; or E represents methylene (—CH$_2$—) or (methyl)methylene, either of which groups may be optionally substituted by one or more substituents.

Alternatively, E represents —O—; or E represents methylene (—CH$_2$—) or (methyl)methylene, either of which groups may be optionally substituted by one or more substituents.

Appositely, E represents methylene (—CH$_2$—) or (methyl)methylene, either of which groups may be optionally substituted by one or more substituents.

Selected examples of typical substituents on the linkage represented by E include halogen, trifluoromethyl, hydroxy, $C_{1-6}$ alkoxy, carboxy($C_{1-6}$)alkoxy, trifluoromethoxy, amino, $C_{1-6}$ alkylamino, di($C_{1-6}$)alkylamino, $C_{2-6}$ alkylcarbonylamino, carboxy, benzyloxycarbonyl and tetrazolyl.

Specific examples of typical substituents on the linkage represented by E include fluoro, trifluoromethyl, hydroxy, methoxy, carboxymethoxy, trifluoromethoxy, amino, methylamino, dimethylamino, acetylamino, carboxy, benzyloxycarbonyl and tetrazolyl.

Typical values of E include —N(R$^5$)—, —CH$_2$—, —CH(OH)—, —CH(OCH$_3$)—, —CH(OCH$_2$CO$_2$H)—, —CH(NH$_2$)—, —CH(NHCOCH$_3$)—, —CH(CO$_2$H)—, —CH(CO$_2$benzyl)-, —CH(CH$_3$)—, —C(CH$_3$)(OH)— and —CH(CH$_2$CH$_3$)—; or E may represent a covalent bond. In addition, E may represent —O—.

Illustrative values of E include —O—, —CH$_2$— and —CH(CH$_3$)—.

Suitable values of E include —CH$_2$— and —CH(CH$_3$)—.

In one embodiment, E represents —CH$_2$—.

In another embodiment, E represents —CH(CH$_3$)—. In a particular aspect of that embodiment, the —CH(CH$_3$)— linkage represented by E is in the (S) stereochemical configuration.

In a first embodiment, Q represents a covalent bond, whereby the integer Z is attached directly to the six-membered ring.

In a second embodiment, Q represents —O—, —S—, —S(O)—, —S(O)$_2$—, —S(O)(NR$^6$)—, —N(R$^6$)—, —C(O)N(R$^6$)—, —N(R$^6$)C(O)—, —S(O)$_2$N(R$^6$)— or —N(R$^6$)S(O)$_2$—. In a first aspect of that embodiment, Q represents —O—. In a second aspect of that embodiment, Q represents —S—. In a third aspect of that embodiment, Q represents —S(O)—. In a fourth aspect of that embodiment, Q represents —S(O)$_2$—. In a fifth aspect of that embodiment, Q represents —S(O)(NR$^6$)—. In a sixth aspect of that embodiment, Q represents —N(R$^6$)—. In a seventh aspect of that embodiment, Q represents —C(O)N(R$^6$)—. In an eighth aspect of that embodiment, Q represents —N(R$^6$)C(O)—. In a ninth aspect of that embodiment, Q represents —S(O)$_2$N(R$^6$)—. In a tenth aspect of that embodiment, Q represents —N(R$^6$)S(O)$_2$—.

In a third embodiment, Q represents an optionally substituted straight or branched $C_{1-6}$ alkylene chain optionally comprising one, two or three heteroatom-containing linkages independently selected from —O—, —S—, —S(O)—, —S(O)$_2$—, —S(O)(NR$^6$)—, —N(R$^6$)—, —C(O)N(R$^6$)—, —N(R$^6$)C(O)—, —S(O)$_2$N(R$^6$)— and —N(R$^6$)S(O)$_2$—. In a first aspect of that embodiment, Q represents an optionally substituted straight or branched $C_{1-6}$ alkylene chain. In a second aspect of that embodiment, Q represents an optionally substituted straight or branched $C_{1-6}$ alkylene chain comprising one heteroatom-containing linkage independently selected from —O—, —S—, —S(O)—, —S(O)$_2$—, —S(O)(NR$^6$)—, —N(R$^6$)—, —C(O)N(R$^6$)—, —N(R$^6$)C(O)—, —S(O)$_2$N(R$^6$)— and —N(R$^6$)S(O)$_2$—. In a third aspect of that embodiment, Q represents an optionally substituted straight or branched $C_{1-6}$ alkylene chain comprising two heteroatom-containing linkages independently selected from —O—, —S—, —S(O)—, —S(O)$_2$—, —S(O)(NR$^6$)—, —N(R$^6$)—, —C(O)N(R$^6$)—, —N(R$^6$)C(O)—, —S(O)$_2$N(R$^6$)— and —N(R$^6$)S(O)$_2$—. In a fourth aspect of that embodiment, Q represents an optionally substituted straight or branched $C_{1-6}$ alkylene chain comprising three heteroatom-containing linkages independently selected from —O—, —S—, —S(O)—, —S(O)$_2$—, —S(O)(NR$^6$)—, —N(R$^6$)—, —C(O)N(R$^6$)—, —N(R$^6$)C(O)—, —S(O)$_2$N(R$^6$)— and —N(R$^6$)S(O)$_2$—. In a fifth aspect of that embodiment, Q represents an optionally substituted straight or branched $C_{1-6}$ alkylene chain comprising one, two or three heteroatom-containing linkages independently selected from —O—, —S—, —N(R$^6$)—, —C(O)N(R$^6$)— and —N(R$^6$)C(O)—.

Typically, Q represents a covalent bond; or Q represents —S(O)— or —S(O)$_2$—; or Q represents an optionally substituted straight or branched $C_{1-6}$ alkylene chain optionally comprising one or two heteroatom-containing linkages selected from —O—, —S—, —N(R$^6$)—, —C(O)N(R$^6$)— and —N(R$^6$)C(O)—.

Generally, Q represents a covalent bond; or Q represents an optionally substituted straight or branched $C_{1-6}$ alkylene chain.

Selected examples of typical substituents on the linkage represented by Q include halogen, cyano, trifluoromethyl, hydroxy, $C_{1-6}$ alkoxy and amino.

Specific examples of typical substituents on the linkage represented by Q include fluoro, cyano, trifluoromethyl, hydroxy, methoxy and amino.

Suitably, Q represents a covalent bond; or Q represents —S(O)—, —S(O)$_2$— or —N(R$^6$)—; or Q represents —CH$_2$—, —CH(F)—, —CF$_2$—, —CH(CN)—, —CH(CH$_3$)—, —CH(OH)—, —CH(CH$_2$OH)—, —CH(OCH$_3$)—, —CH(NH$_2$)—, —CH$_2$CH$_2$—, —CH(OH)CH$_2$—, —CH(OH)CF$_2$—, —CH(OCH$_3$)CH$_2$—, —CH$_2$O—, —CH(CH$_3$)O—, —C(CH$_3$)$_2$O—, —CH(CH$_2$CH$_3$)O—, —CH(CF$_3$)O—, —CH$_2$S—, —CH$_2$S(O)—, —CH$_2$S(O)$_2$—, —CH$_2$N(R$^6$)—, —CH$_2$CH$_2$CH$_2$—, —CH(OH)CH$_2$CH$_2$—, —CH(OCH$_3$)CH$_2$CH$_2$—, —CH$_2$CH$_2$O—, —CH$_2$OCH$_2$—, —CH$_2$OCH(F)—, —CH$_2$OCF$_2$—, —CH$_2$OCH(CH$_3$)—, —CH(CH$_3$)OCH$_2$—, —CH$_2$OC(CH$_3$)$_2$—, —C(CH$_3$)$_2$OCH$_2$—, —CH$_2$SCH$_2$—, —CH$_2$S(O)CH$_2$—, —CH$_2$S(O)$_2$CH$_2$—, —CH$_2$CH$_2$N(R$^6$)—, —CH$_2$N(R$^6$)CH$_2$—, —CH$_2$N(R$^6$)C(O)—, —CH$_2$CH$_2$OCH$_2$—, —CH$_2$CH$_2$N(R$^6$)C(O)—, —CH$_2$OCH$_2$CH$_2$—, —CH$_2$OCH$_2$CF$_2$—, —CH$_2$OCH$_2$CH(CH$_3$)—, —CH$_2$OCH(CH$_3$)CH$_2$—, —CH$_2$OC(CH$_3$)$_2$CH$_2$—, —CH$_2$OCH$_2$CH(CH$_3$)CH$_2$—, —CH$_2$OCH$_2$CH$_2$O—, —CH$_2$OCH$_2$C(O)N(R$^6$)— or —CH$_2$OCH$_2$CH$_2$OCH$_2$—.

Appositely, Q represents a covalent bond; or Q represents —CH$_2$—, —CH(CN)—, —CH(OH)—, —CH(OCH$_3$)—, —CH$_2$O—, —CH$_2$N(R$^6$)— or —CH$_2$OCH$_2$—.

Generally, Q represents a covalent bond; or Q represents —CH$_2$—.

Particular values of Q include —CH$_2$—, —CH(OH)—, —CH$_2$O—, —CH$_2$S— and —CH$_2$OCH$_2$—. In a first embodiment, Q represents —CH$_2$—. In a second embodiment, Q represents —CH(OH)—. In a third embodiment, Q represents —CH$_2$O—. In a fourth embodiment, Q represents —CH$_2$S—. In a fifth embodiment, Q represents —CH$_2$OCH$_2$—.

Generally, Y represents $C_{3-7}$ cycloalkyl, aryl or heteroaryl, any of which groups may be optionally substituted by one or more substituents.

Typically, Y represents aryl or heteroaryl, either of which groups may be optionally substituted by one or more substituents.

In a first embodiment, Y represents optionally substituted $C_{3-7}$ cycloalkyl. In one aspect of that embodiment, Y represents unsubstituted $C_{3-7}$ cycloalkyl. In another aspect of that embodiment, Y represents monosubstituted $C_{3-7}$ cycloalkyl. In a further aspect of that embodiment, Y represents disubstituted $C_{3-7}$ cycloalkyl.

In a second embodiment, Y represents optionally substituted aryl. In one aspect of that embodiment, Y represents unsubstituted aryl. In another aspect of that embodiment, Y represents monosubstituted aryl. In a further aspect of that embodiment, Y represents disubstituted aryl.

In a third embodiment, Y represents optionally substituted $C_{3-7}$ heterocycloalkyl. In one aspect of that embodiment, Y represents unsubstituted $C_{3-7}$ heterocycloalkyl. In another aspect of that embodiment, Y represents monosubstituted $C_{3-7}$ heterocycloalkyl. In a further aspect of that embodiment, Y represents disubstituted $C_{3-7}$ heterocycloalkyl.

In a fourth embodiment, Y represents optionally substituted heteroaryl. In one aspect of that embodiment, Y represents unsubstituted heteroaryl. In another aspect of that embodiment, Y represents monosubstituted heteroaryl. In a further aspect of that embodiment, Y represents disubstituted heteroaryl.

Suitably, Y represents benzocyclobutenyl, phenyl, thienyl, thiazolyl or pyridinyl, any of which groups may be optionally substituted by one or more substituents.

Appropriately, Y represents phenyl, thienyl or thiazolyl, any of which groups may be optionally substituted by one or more substituents.

Appositely, Y represents phenyl, which may be optionally substituted by one or more substituents.

Examples of optional substituents which may be present on the moiety Y include one, two or three substituents independently selected from halogen, cyano, nitro, $C_{1-6}$ alkyl, trifluoromethyl, hydroxy, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, ($C_{1-6}$)alkylsulfonyloxy, amino, $C_{1-6}$ alkylamino, di($C_{1-6}$)alkylamino, arylamino, $C_{2-6}$ alkylcarbonylamino, $C_{1-6}$ alkylsulfonylamino, formyl, $C_{2-6}$ alkylcarbonyl, $C_{3-6}$ cycloalkylcarbonyl, $C_{3-6}$ heterocycloalkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl and di($C_{1-6}$)alkylaminosulfonyl.

Illustrative examples of optional substituents on the moiety Y include halogen, $C_{1-6}$ alkyl, $C_{1-6}$ alkoxy and difluoromethoxy. Additional examples include cyano.

Typical examples of optional substituents on the moiety Y include halogen, cyano and difluoromethoxy.

Examples of particular substituents on the moiety Y include fluoro, chloro, bromo, cyano, nitro, methyl, isopropyl, trifluoromethyl, hydroxy, methoxy, difluoromethoxy, trifluoromethoxy, methylthio, methylsulfinyl, methylsulfonyl, methylsulfonyloxy, amino, methylamino, tert-butylamino, dimethylamino, phenylamino, acetylamino, methylsulfonylamino, formyl, acetyl, cyclopropylcarbonyl, azetidinylcarbonyl, pyrrolidinylcarbonyl, piperidinylcarbonyl, piperazinylcarbonyl, morpholinylcarbonyl, carboxy, methoxycarbonyl, aminocarbonyl, methylaminocarbonyl, dimethylaminocarbonyl, aminosulfonyl, methylaminosulfonyl and dimethylaminosulfonyl.

Illustrative examples of particular substituents on the moiety Y include chloro, methyl, methoxy and difluoromethoxy. Additional examples include cyano.

Typical examples of particular substituents on the moiety Y include fluoro, chloro, cyano and difluoromethoxy.

Typical values of Y include benzocyclobutenyl, phenyl, fluorophenyl (including 2-fluorophenyl, 3-fluorophenyl and 4-fluorophenyl), chlorophenyl (including 2-chlorophenyl, 3-chlorophenyl and 4-chlorophenyl), difluorophenyl (including 2,6-difluorophenyl), (chloro)(fluoro)phenyl (including 5-chloro-2-fluorophenyl and 2-chloro-5-fluorophenyl), dichlorophenyl (including 2,5-dichlorophenyl and 2,6-dichlorophenyl), methylphenyl (including 4-methylphenyl), dimethylphenyl (including 2,5-dimethylphenyl and 2,6-dimethylphenyl), (trifluoromethyl)phenyl [including 2-(trifluoromethyl)phenyl], (chloro)(trifluoromethyl)phenyl [including 5-chloro-2-(trifluoromethyl)phenyl], (methyl)-(trifluoromethyl)phenyl [including 2-methyl-5-(trifluoromethyl)phenyl], bis(trifluoro-methyl)phenyl [including 2,5-bis(trifluoromethyl)phenyl], methoxyphenyl (including 2-methoxyphenyl), (difluoromethoxy)phenyl [including 2-(difluoromethoxy)phenyl and 3-(difluoromethoxy)phenyl], (difluoromethoxy)(fluoro)phenyl [including 2-(difluoro-methoxy)-5-fluorophenyl and 2-(difluoromethoxy)-6-fluorophenyl], (chloro)(difluoromethoxy)phenyl [including 5-chloro-2-(difluoromethoxy) phenyl and 6-chloro-2-(difluoromethoxy)phenyl], (cyano) (difluoromethoxy)phenyl [including 6-cyano-2-(difluoromethoxy)phenyl], (trifluoromethoxy)phenyl [including 2-(trifluoromethoxy)-phenyl], methylsulfonyloxyphenyl, (amino)(chloro)phenyl (including 5-amino-2-chlorophenyl), methylthienyl (including 3-methylthien-2-yl), methylthiazolyl (including 2-methyl-1,3-thiazol-4-yl), (chloro)(methyl)thiazolyl (including 5-chloro-2-methyl-1,3-thiazol-4-yl), dimethylthiazolyl (including 2,4-dimethyl-1,3-thiazol-5-yl) and pyridinyl (including pyridin-3-yl and pyridin-4-yl).

Illustrative values of Y include phenyl, chlorophenyl, methylphenyl, methoxyphenyl and (difluoromethoxy)phenyl.

Selected values of Y include dichlorophenyl, dimethylphenyl, (difluoromethoxy)-phenyl, (difluoromethoxy)(fluoro)phenyl, (chloro)(difluoromethoxy)phenyl, (cyano)-(difluoromethoxy)phenyl, methylsulfonyloxyphenyl, methylthienyl and dimethylthiazolyl.

In one embodiment, Y represents 2,5-dichlorophenyl.
In another embodiment, Y represents phenyl.
In another embodiment, Y represents 2-chlorophenyl.
In another embodiment, Y represents 2-methylphenyl.
In another embodiment, Y represents 2,5-dimethylphenyl.
In another embodiment, Y represents 2-methoxyphenyl.
In a particular embodiment, Y represents 2-(difluoromethoxy)phenyl.
In another embodiment, Y represents (difluoromethoxy)(fluoro)phenyl.
In another embodiment, Y represents (chloro)(difluoromethoxy) phenyl.
In another embodiment, Y represents (cyano)(difluoromethoxy) phenyl.
In another embodiment, Y represents 3-methylthien-2-yl.
In another embodiment, Y represents 2,4-dimethyl-1,3-thiazol-5-yl.

In one embodiment, Z represents hydrogen.
In another embodiment, Z is other than hydrogen.
In a selected embodiment, Z represents hydrogen; or Z represents $C_{1-6}$ alkyl, $C_{3-7}$ cycloalkyl, aryl, $C_{3-7}$ heterocycloalkyl, $C_{3-7}$ heterocycloalkenyl or heteroaryl, any of which groups may be optionally substituted by one or more substituents; or Z represents —$Z^1$—$Z^2$ or —$Z^1$—C(O)—$Z^2$, either of which moieties may be optionally substituted by one or more substituents.

In a further embodiment, Z represents $C_{1-6}$ alkyl, $C_{3-7}$ cycloalkyl, aryl, $C_{3-7}$ heterocycloalkyl, $C_{3-7}$ heterocycloalkenyl or heteroaryl, any of which groups may be optionally substituted by one or more substituents; or Z represents —$Z^1$—$Z^2$ or —$Z^1$—C(O)—$Z^2$, either of which moieties may be optionally substituted by one or more substituents.

Suitably, Z represents hydrogen; or Z represents $C_{1-6}$ alkyl, aryl or heteroaryl, any of which groups may be optionally substituted by one or more substituents; or Z represents —$Z^1$—$Z^2$, which moiety may be optionally substituted by one or more substituents.

Appositely, Z represents hydrogen; or Z represents $C_{1-6}$ alkyl, which group may be optionally substituted by one or more substituents.

Typically, Z represents hydrogen, fluoro or trifluoromethyl; or Z represents methyl, ethyl, n-propyl, isopropyl, n-butyl, sec-butyl, isobutyl, tert-butyl, cyclopropyl, cyclobutyl, cyclopentyl, cyclohexyl, phenyl, tetrahydrofuranyl, pyrrolidinyl, indolinyl, tetrahydropyranyl, piperidinyl, 1,2,3,4-tetrahydroquinolinyl, morpholinyl, azocanyl, thiazolinyl, furyl, thienyl, pyrazolyl, 4,5,6,7-tetrahydroindazolyl, benzoxazolyl, isoxazolyl, thiazolyl, benzothiazolyl, imidazolyl, benzimidazolyl, [1,2,4]triazolo[1,5-c]-pyrimidinyl, tetrazolyl, pyridinyl, quinolinyl, isoquinolinyl, phthalazinyl, pyrimidinyl or pyrazinyl, any of which groups may be optionally substituted by one or more substituents; or Z represents —$Z^1$—$Z^2$ or —$Z^1$—C(O)—$Z^2$, either of which moieties may be optionally substituted by one or more substituents.

The moiety $Z^1$ represents a divalent radical derived from an aryl, $C_{3-7}$ heterocycloalkyl or heteroaryl group, any of which groups may be optionally substituted by one or more substituents. Typically, the moiety $Z^1$ represents a divalent radical derived from a phenyl, pyrrolidinyl, piperazinyl, pyrazolyl, thiazolyl, triazolyl, tetrazolyl or pyridinyl group, any of which groups may be optionally substituted by one or more substituents. Typical values of the moiety $Z^1$ include the groups of formula (Za), (Zb), (Zc), (Zd), (Ze), (Zf), (Zg), (Zh), (Zj) and (Zk):

(Za)

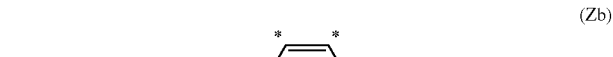

(Zb)

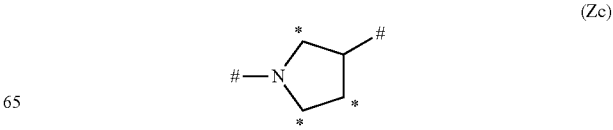

(Zc)

-continued

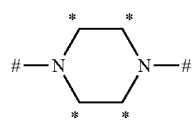
(Zd)

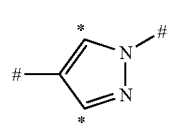
(Ze)

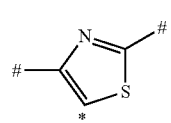
(Zf)

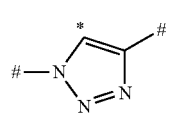
(Zg)

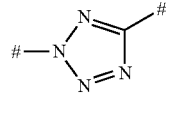
(Zh)

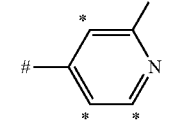
(Zj)

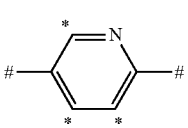
(Zk)

wherein the symbols # represent the points of attachment of the moiety $Z^1$ to the remainder of the molecule; and the asterisks (*) represent the site of attachment of optional substituents.

Particular values of the moiety $Z^1$ include the groups of formula (Za), (Zc), (Ze), (Zf), (Zg), (Zh) and (Zj) as depicted above.

The moiety $Z^2$ represents aryl, $C_{3-7}$ heterocycloalkyl, $C_{3-7}$ heterocycloalkenyl or heteroaryl, any of which groups may be optionally substituted by one or more substituents. Typically, $Z^2$ represents phenyl, pyrrolidinyl, oxazolidinyl, imidazolidinyl, morpholinyl, imidazolinyl, thiazolyl, imidazolyl, tetrazolyl or pyridinyl, any of which groups may be optionally substituted by one or more substituents.

Examples of optional substituents which may be present on the moiety Z, $Z^1$ or $Z^2$ include one, two or three substituents independently selected from halogen, cyano, nitro, $C_{1-6}$ alkyl, trifluoromethyl, oxo, hydroxy, hydroxy($C_{1-6}$) alkyl, $C_{1-6}$ alkoxy, difluoro-methoxy, trifluoromethoxy, $C_{1-3}$ alkylenedioxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, di($C_{1-6}$)alkylamino($C_{1-6}$)alkyl, $C_{2-6}$ alkylcarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl, di($C_{1-6}$)alkylaminosulfonyl, aminocarbonylamino and hydrazinocarbonyl.

Examples of particular substituents on the moiety Z, $Z^1$ or $Z^2$ include fluoro, chloro, bromo, cyano, nitro, methyl, ethyl, isopropyl, trifluoromethyl, oxo, hydroxy, hydroxymethyl, methoxy, difluoromethoxy, trifluoromethoxy, methylenedioxy, methylthio, methylsulfinyl, methylsulfonyl, amino, methylamino, tert-butylamino, dimethylamino, dimethylaminomethyl, dimethylaminoethyl, acetylamino, methylsulfonylamino, formyl, acetyl, carboxy, methoxycarbonyl, tert-butoxycarbonyl, aminocarbonyl, methylaminocarbonyl, dimethylaminocarbonyl, aminosulfonyl, methylaminosulfonyl, dimethylaminosulfonyl, aminocarbonylamino and hydrazinocarbonyl.

Typical values of $Z^2$ include phenyl, hydroxyphenyl, oxopyrrolidinyl, dioxo-pyrrolidinyl, (hydroxy)(oxo)pyrrolidinyl, (amino)(oxo)pyrrolidinyl, (oxo)oxazolidinyl, oxoimidazolidinyl, morpholinyl, imidazolinyl, methylthiazolyl, formylthiazolyl, imidazolyl, tetrazolyl and pyridinyl.

Selected values of $Z^2$ include oxopyrrolidinyl and (oxo) oxazolidinyl. In one embodiment, $Z^2$ represents oxopyrrolidinyl. In another embodiment, $Z^2$ represents (oxo)oxazolidinyl.

Typical values of Z include hydrogen, fluoro, trifluoromethyl, methyl, ethyl, n-propyl, isopropyl, isobutyl, tert-butyl, cyclopropyl, cyclopentyl, cyclohexyl, oxo-cyclohexyl, phenyl, bromophenyl, cyanophenyl, nitrophenyl, methoxyphenyl, difluoro-methoxyphenyl, trifluoromethoxyphenyl, methylenedioxyphenyl, methylsulfonylphenyl, dimethylaminophenyl, acetylaminophenyl, methylsulfonylaminophenyl, carboxyphenyl, aminocarbonylphenyl, methylaminocarbonylphenyl, dimethylaminocarbonylphenyl, aminocarbonylaminophenyl, tetrahydrofuranyl, oxopyrrolidinyl, dimethylamino-pyrrolidinyl, tert-butoxycarbonylpyrrolidinyl, indolinyl, tetrahydropyranyl, piperidinyl, ethylpiperidinyl, tert-butoxycarbonylpiperidinyl, amino carbonylpiperidinyl, 2-oxo-3,4-dihydroquinolinyl, morpholinyl, azocanyl, oxothiazolinyl, furyl, hydroxymethylfuryl, thienyl, methylpyrazolyl, dimethylpyrazolyl, 4,5,6,7-tetrahydroindazolyl, benzoxazolyl, methylisoxazolyl, dimethylisoxazolyl, methylthiazolyl, aminothiazolyl, benzothiazolyl, methylbenzothiazolyl, aminobenzothiazolyl, imidazolyl, methylimidazolyl, methyl-benzimidazolyl, dimethyl[1,2,4] triazolo[1,5-c]pyrimidinyl, dimethylaminoethyltetrazolyl, pyridinyl, fluoropyridinyl, chloropyridinyl, cyanopyridinyl, methylpyridinyl, (cyano)-(methyl)pyridinyl, trifluoromethylpyridinyl, oxopyridinyl, methoxypyridinyl, methylsulfonylpyridinyl, dimethylaminomethylpyridinyl, acetylaminopyridinyl, carboxypyridinyl, methoxycarbonylpyridinyl, aminocarbonylpyridinyl, (aminocarbonyl)(fluoro)-pyridinyl, methylaminocarbonylpyridinyl, dimethylaminocarbonylpyridinyl, hydrazino-carbonylpyridinyl, quinolinyl, isoquinolinyl, (methyl)(oxo)phthalazinyl, pyrimidinyl, pyrazinyl, oxopyrrolidinylphenyl, dioxopyrrolidinylphenyl, (hydroxy)(oxo)pyrrolidinylphenyl, (amino)(oxo)pyrrolidinylphenyl, (oxo)oxazolidinylphenyl, oxoimidazolidinylphenyl, imidazolinylphenyl, methylthiazolylphenyl, formylthiazolylphenyl, imidazolyl-phenyl, tetrazolylphenyl, phenylpyrrolidinyl, hydroxyphenylpiperazinyl, (methyl)-(phenyl)pyrazolyl, oxoimidazolidinylthiazolyl, hydroxyphenyltriazolyl, morpholinyl-tetrazolyl, oxopyrrolidinylpyridinyl, (oxo)oxazolidinylpyridinyl, oxoimidazolidinyl-pyridinyl, pyridinylthiazolyl, pyridinyltetrazolyl and morpholinylcarbonylphenyl.

Particular values of Z include hydrogen, methyl, methylsulfonylphenyl, pyridinyl, methylsulfonylpyridinyl, oxopyrrolidinylphenyl, (hydroxy)(oxo)pyrrolidinylphenyl and (oxo)oxazolidinylphenyl.

Selected values of Z include hydrogen and methyl.

In a first embodiment, Z represents hydrogen. In a second embodiment, Z represents methyl. In a third embodiment, Z represents methylsulfonylphenyl. In one aspect of that embodiment, Z represents 3-(methylsulfonyl)phenyl. In another aspect of that embodiment, Z represents 4-(methylsulfonyl)phenyl. In a fourth embodiment, Z represents pyridinyl. In one aspect of that embodiment, Z represents pyridin-4-yl. In a fifth embodiment, Z represents oxopyrrolidinylphenyl. In one aspect of that embodiment, Z represents 3-(2-oxopyrrolidin-1-yl)phenyl. In a sixth embodiment, Z represents (hydroxy)(oxo)pyrrolidinylphenyl. In one aspect of that embodiment, Z represents 3-(3-hydroxy-2-oxopyrrolidin-1-yl)phenyl. In another aspect of that embodiment, Z represents 3-(4-hydroxy-2-oxopyrrolidin-1-yl)phenyl. In a seventh embodiment, Z represents (oxo)oxazolidinylphenyl. In one aspect of that embodiment, Z represents 3-(2-oxo-oxazolidin-3-yl)phenyl. In an eighth embodiment, Z represents methylsulfonylpyridinyl.

Suitably, $R^1$, $R^2$, $R^3$ and $R^4$ independently represent hydrogen, halogen, cyano, trifluoromethyl or —$CO_2R^d$; or $C_{1-6}$ alkyl, $C_{2-6}$ alkynyl, aryl, $C_{3-7}$ heterocycloalkyl, $C_{3-7}$ heterocycloalkenyl, heteroaryl, ($C_{3-7}$)heterocycloalkyl($C_{1-6}$)alkyl-aryl-, heteroaryl-($C_{3-7}$)heterocycloalkyl-, ($C_{3-7}$)cycloalkyl-heteroaryl-, ($C_{3-7}$)cycloalkyl($C_{1-6}$)alkyl-heteroaryl-, ($C_{4-7}$)cycloalkenyl-heteroaryl-, ($C_{4-9}$)bicycloalkyl-heteroaryl-, ($C_{3-7}$)heterocycloalkyl-heteroaryl-, ($C_{3-7}$)heterocycloalkyl($C_{1-6}$)alkyl-hetero aryl-, ($C_{3-7}$)heterocycloalkenyl-heteroaryl-, ($C_{4-9}$)heterobicycloalkyl-heteroaryl- or ($C_{4-9}$)spiroheterocycloalkyl-heteroaryl-, any of which groups may be optionally substituted by one or more substituents.

Typically, $R^1$, $R^2$, $R^3$ and $R^4$ independently represent hydrogen; or aryl or heteroaryl, either of which groups may be optionally substituted by one or more substituents.

Examples of optional substituents which may be present on $R^1$, $R^2$, $R^3$ or $R^4$ include one, two or three substituents independently selected from halogen, halo-($C_{1-6}$)alkyl, cyano, cyano($C_{1-6}$)alkyl, nitro, nitro($C_{1-6}$)alkyl, $C_{1-6}$ alkyl, difluoromethyl, trifluoromethyl, difluoroethyl, trifluoroethyl, $C_{2-6}$ alkenyl, hydroxy, hydroxy($C_{1-6}$)alkyl, $C_{1-6}$ alkoxy, difluoromethoxy, trifluoromethoxy, trifluoroethoxy, carboxy($C_{3-7}$)cycloalkyloxy, $C_{1-3}$ alkylenedioxy, $C_{1-6}$ alkoxy($C_{1-6}$)alkyl, pentafluorothio, $C_{1-6}$ alkylthio, $C_{1-6}$ alkylsulphinyl, $C_{1-6}$ alkylsulphonyl, ($C_{1-6}$)alkylsulphonyl($C_{1-6}$)alkyl, oxo, amino, amino-($C_{1-6}$)alkyl, $C_{1-6}$ alkylamino, di($C_{1-6}$)alkylamino, hydroxy($C_{1-6}$)alkylamino, $C_{1-6}$ alkoxyamino, ($C_{1-6}$)alkoxy($C_{1-6}$)alkylamino, [($C_{1-6}$)alkoxy](hydroxy)($C_{1-6}$)alkylamino, [($C_{1-6}$)alkylthio](hydroxy)($C_{1-6}$)alkylamino, N—[($C_{1-6}$)alkyl]-N-[hydroxy($C_{1-6}$)alkyl]amino, di($C_{1-6}$)alkylamino($C_{1-6}$)alkylamino, N-[di($C_{1-6}$)alkylamino($C_{1-6}$)alkyl]-N-[hydroxy($C_{1-6}$)-alkyl]amino, hydroxy($C_{1-6}$)alkyl($C_{3-7}$)cycloalkylamino, (hydroxy)[($C_{3-7}$)cycloalkyl($C_{1-6}$)-alkyl]amino, ($C_{3-7}$)heterocycloalkyl($C_{1-6}$)alkylamino, oxo($C_{3-7}$)heterocycloalkyl($C_{1-6}$)alkylamino, ($C_{1-6}$)alkylheteroarylamino, heteroaryl($C_{1-6}$)alkylamino, ($C_{1-6}$)alkylheteroaryl($C_{1-6}$)-alkylamino, $C_{2-6}$ alkylcarbonylamino, N—[($C_{1-6}$)alkyl]-N—[($C_{2-6}$)alkylcarbonyl]amino, ($C_{2-6}$)-alkylcarbonylamino($C_{1-6}$)alkyl, $C_{3-6}$ alkenylcarbonylamino, bis[($C_{3-6}$)alkenylcarbonyl]-amino, N—[($C_{1-6}$)alkyl]-N—[($C_{3-7}$)cycloalkylcarbonyl]amino, $C_{2-6}$ alkoxycarbonylamino, $C_{2-6}$ alkoxycarbonyl($C_{1-6}$)alkylamino, $C_{1-6}$ alkylaminocarbonylamino, $C_{1-6}$ alkylsulphonylamino, N—[($C_{1-6}$)alkyl]-N—[($C_{1-6}$)alkylsulphonyl]amino, bis[($C_{1-6}$)alkylsulphonyl]amino, N—[($C_1$-$C_6$)alkyl]-N-[carboxy($C_{1-6}$)alkyl]amino, carboxy($C_{3-7}$)cycloalkylamino, carboxy-($C_{3-7}$)cycloalkyl($C_{1-6}$)alkylamino, formyl, $C_{2-6}$ alkylcarbonyl, ($C_{3-7}$)cycloalkylcarbonyl, phenylcarbonyl, ($C_{2-6}$)alkylcarbonyloxy($C_{1-6}$)alkyl, carboxy, carboxy($C_{1-6}$)alkyl, $C_{2-6}$ alkoxycarbonyl, $C_{2-6}$ alkoxycarbonyl($C_{1-6}$)alkyl, morpholinyl($C_{1-6}$)alkoxycarbonyl, $C_{2-6}$ alkoxycarbonylmethylidenyl, a carboxylic acid isostere or prodrug moiety Ω, —($C_{1-6}$)alkyl-Ω, aminocarbonyl, $C_{1-6}$ alkylaminocarbonyl, hydroxy($C_{1-6}$)alkylaminocarbonyl, di($C_{1-6}$)alkylaminocarbonyl, aminocarbonyl($C_{1-6}$)alkyl, aminosulphonyl, di($C_{1-6}$)alkylaminosulphonyl, ($C_{1-6}$)alkylsulphoximinyl and [($C_{1-6}$)alkyl][N—($C_{1-6}$)alkyl]-sulphoximinyl.

By the expression "carboxylic acid isostere or prodrug moiety" is meant any functional group, structurally distinct from a carboxylic acid moiety, that will be recognised by a biological system as being similar to, and thus capable of mimicking, a carboxylic acid moiety, or will be readily convertible by a biological system in vivo into a carboxylic acid moiety. A synopsis of some common carboxylic acid isosteres is presented by N. A. Meanwell in *J. Med. Chem.*, 2011, 54, 2529-2591 (cf. in particular FIGS. 25 and 26). An alternative carboxylic acid isostere is described by N Pemberton et al. in *ACS Med. Chem. Lett.*, 2012, 3, 574-578. Typical examples of suitable carboxylic acid isostere or prodrug moieties represented by Ω include the functional groups of formula (i) to (xliii):

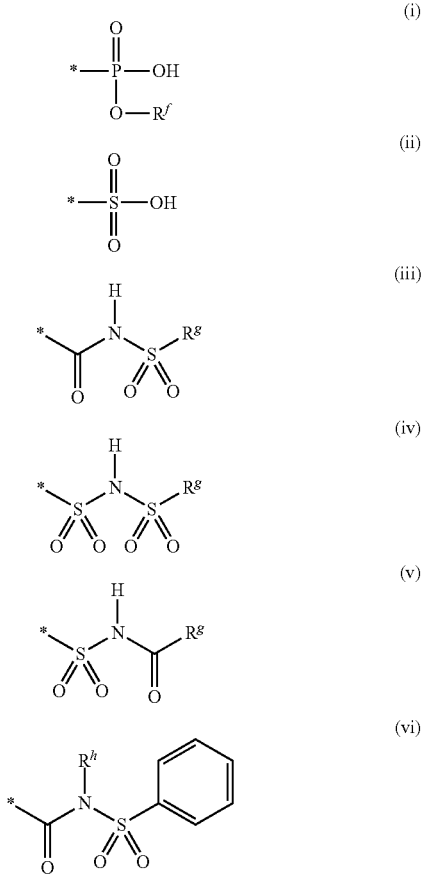

(vii)
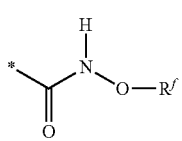
(viii)
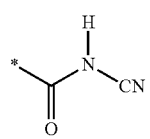
(ix)
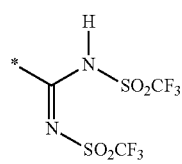
(x)
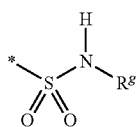
(xi)
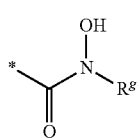
(xii)
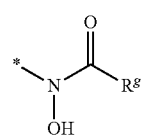
(xiii)
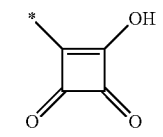
(xiv)
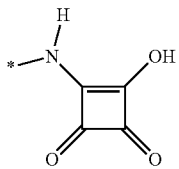
(xv)
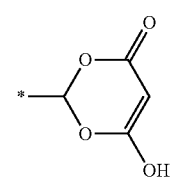
(xvi)
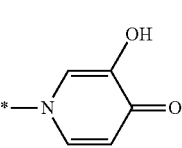
(xvii)
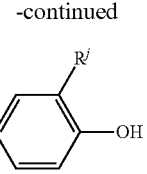
(xviii)
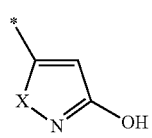
(xix)
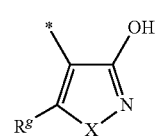
(xx)
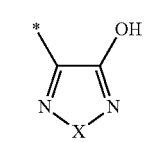
(xxi)
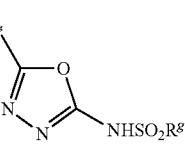
(xxii)
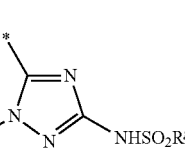
(xxiii)
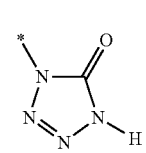
(xxiv)
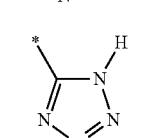
(xxv)
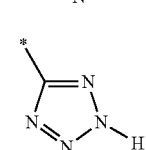
(xxvi)
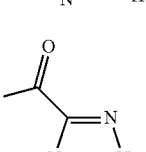
(xxvii)
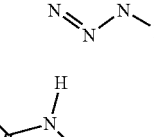
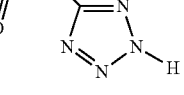

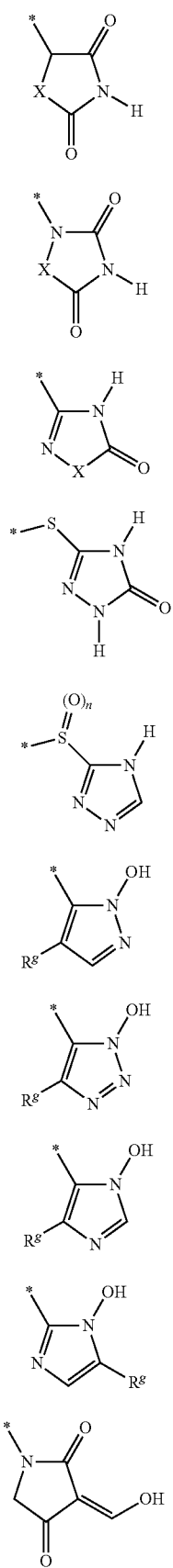

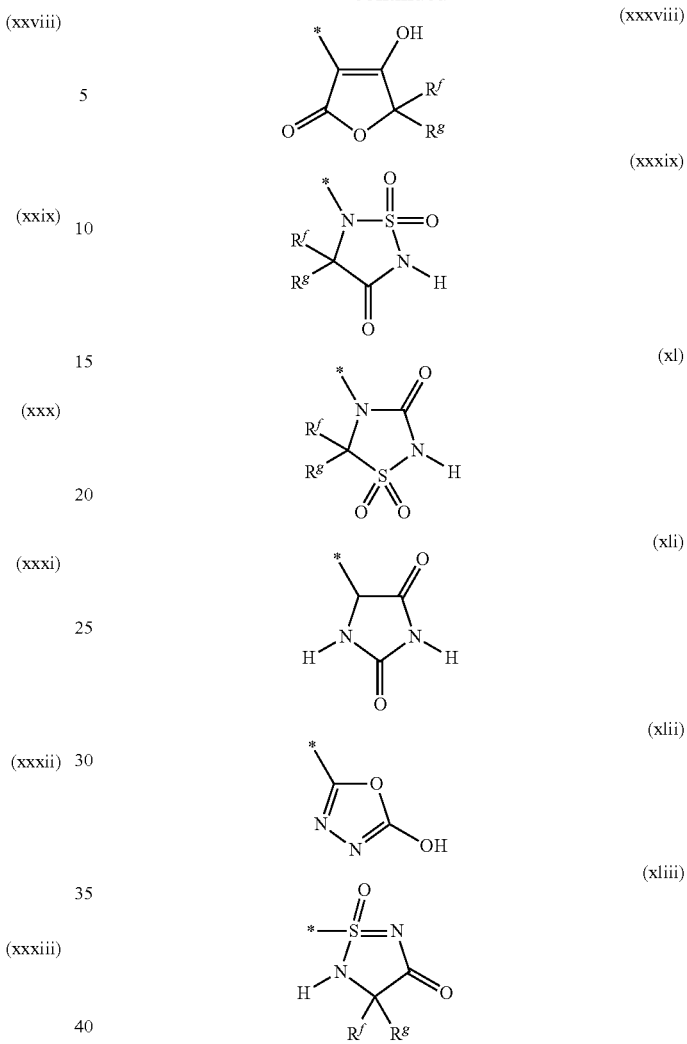

wherein
the asterisk (*) represents the site of attachment to the remainder of the molecule;
n is zero, 1 or 2;
X represents oxygen or sulphur;
$R^f$ represents hydrogen, $C_{1-6}$ alkyl or —CH$_2$CH(OH)CH$_2$OH;
$R^g$ represents $C_{1-6}$ alkyl, trifluoromethyl, —CH$_2$CH$_2$F, —CH$_2$CHF$_2$, —CH$_2$CF$_3$ or —CF$_2$CF$_3$;
$R^h$ represents hydrogen, cyano or —CO$_2$R$^d$, in which R$^d$ is as defined above; and
$R^j$ represents hydrogen or halogen.

In one embodiment, n is zero. In another embodiment, n is 1. In a further embodiment, n is 2.

In one embodiment, X represents oxygen. In another embodiment, X represents sulphur.

In one embodiment, $R^f$ represents hydrogen. In another embodiment, $R^f$ represents $C_{1-6}$ alkyl, especially methyl. In a further embodiment, $R^f$ is —CH$_2$CH(OH)CH$_2$OH.

In one embodiment, $R^g$ represents $C_{1-6}$ alkyl, especially methyl. In another embodiment, $R^g$ represents trifluoromethyl, —CH$_2$CH$_2$F, —CH$_2$CHF$_2$, —CH$_2$CF$_3$ or —CF$_2$CF$_3$. In a first aspect of that embodiment, $R^g$ represents trifluoromethyl. In a second aspect of that embodiment, $R^g$ represents —CH$_2$CH$_2$F. In a third aspect of that embodiment, $R^g$ represents —CH$_2$CHF$_2$. In a fourth aspect of that embodiment, $R^g$ represents —CH$_2$CF$_3$. In a fifth aspect of that embodiment, $R^g$ represents —CF$_2$CF$_3$.

In one embodiment, $R^h$ is hydrogen. In another embodiment, $R^h$ represents cyano. In a further embodiment, $R^h$ represents —CO$_2$R$^d$, especially methoxycarbonyl.

In one embodiment, $R^j$ represents hydrogen. In another embodiment, $R^j$ represents halogen, especially chloro.

In a selected embodiment, Ω represents tetrazolyl, especially a C-linked tetrazolyl moiety of formula (xxiv) or (xxv) as depicted above, in particular a group of formula (xxiv) as depicted above.

In another embodiment, Ω represents C$_{1-6}$ alkylsulphonylaminocarbonyl, i.e. a moiety of formula (iii) as depicted above wherein $R^g$ represents C$_{1-6}$ alkyl.

In another embodiment, Ω represents C$_{1-6}$ alkylaminosulphonyl, i.e. a moiety of formula (x) as depicted above wherein $R^g$ represents C$_{1-6}$ alkyl.

In a further embodiment, Ω represents (C$_{1-6}$)alkylcarbonylaminosulphonyl, i.e. a moiety of formula (v) as depicted above wherein $R^g$ represents C$_{1-6}$ alkyl.

Typical examples of optional substituents which may be present on R$^1$, R$^2$, R$^3$ or R$^4$ include one, two or three substituents independently selected from hydroxy(C$_{1-6}$)alkyl and C$_{1-6}$ alkylsulphonyl.

Examples of particular substituents on R$^1$, R$^2$, R$^3$ or R$^4$ include fluoro, chloro, bromo, fluoromethyl, fluoroisopropyl, cyano, cyanoethyl, nitro, nitromethyl, methyl, ethyl, isopropyl, isobutyl, tert-butyl, difluoromethyl, trifluoromethyl, difluoroethyl, trifluoroethyl, ethenyl, hydroxy, hydroxymethyl, hydroxyisopropyl, methoxy, isopropoxy, difluoromethoxy, trifluoromethoxy, trifluoroethoxy, carboxycyclobutyloxy, methylenedioxy, ethylenedioxy, methoxymethyl, methoxyethyl, pentafluorothio, methylthio, methylsulphinyl, methylsulphonyl, methylsulphonylethyl, oxo, amino, aminomethyl, aminoisopropyl, methylamino, ethylamino, dimethylamino, hydroxyethylamino, hydroxypropylamino, (hydroxy)(methyl)propylamino, methoxyamino, methoxyethylamino, (hydroxy)(methoxy)(methyl)propylamino, (hydroxy)(methylthio)butylamino, N-(hydroxyethyl)-N-(methyl)amino, dimethylaminoethylamino, (dimethylamino)(methyl)-propylamino, N-(dimethylaminoethyl)-N-(hydroxyethyl)amino, hydroxymethyl-cyclopentylamino, hydroxycyclobutylmethylamino, (cyclopropyl)(hydroxy)propylamino, morpholinylethylamino, oxopyrrolidinylmethylamino, ethyloxadiazolylamino, methyl-thiadiazolylamino, thiazolylmethylamino, thiazolylethylamino, pyrimidinylmethylamino, methylpyrazolylmethylamino, acetylamino, N-acetyl-N-methylamino, N-isopropyl-carbonyl-N-methylamino, acetylaminomethyl, ethenylcarbonylamino, bis(ethenyl-carbonyl)amino, N-cyclopropylcarbonyl-N-methylamino, methoxycarbonylamino, ethoxycarbonylamino, tert-butoxycarbonylamino, methoxycarbonylethylamino, ethylaminocarbonylamino, butylaminocarbonylamino, methylsulphonylamino, N-methyl-N-(methylsulphonyl)amino, bis(methylsulphonyl)amino, N-(carboxymethyl)-N-methylamino, N-(carboxyethyl)-N-methylamino, carboxycyclopentylamino, carboxycyclopropylmethylamino, formyl, acetyl, isopropylcarbonyl, cyclobutylcarbonyl, phenylcarbonyl, acetoxyisopropyl, carboxy, carboxymethyl, carboxyethyl, methoxycarbonyl, ethoxycarbonyl, n-butoxycarbonyl, tert-butoxycarbonyl, methoxycarbonylmethyl, ethoxycarbonylmethyl, ethoxycarbonylethyl, morpholinylethoxycarbonyl, ethoxycarbonylmethylidenyl, methylsulphonylaminocarbonyl, acetylaminosulphonyl, methoxyaminocarbonyl, tetrazolyl, tetrazolylmethyl, hydroxyoxadiazolyl, aminocarbonyl, methylamino-carbonyl, hydroxyethylaminocarbonyl, dimethylaminocarbonyl, aminocarbonylmethyl, aminosulphonyl, methylaminosulphonyl, dimethylaminosulphonyl, methylsulphoximinyl and (methyl)(N-methyl)sulphoximinyl.

Typical examples of particular substituents which may be present on R$^1$, R$^2$, R$^3$ or R$^4$ include one, two or three substituents independently selected from hydroxyisopropyl and methylsulphonyl.

Typically, R$^1$ represents hydrogen, halogen, cyano or —CO$_2$R$^d$; or C$_{1-6}$ alkyl, C$_{2-6}$ alkynyl, aryl, C$_{3-7}$ heterocycloalkyl, C$_{3-7}$ heterocycloalkenyl, heteroaryl, (C$_{3-7}$)heterocycloalkyl(C$_{1-6}$)alkyl-aryl-, heteroaryl(C$_{3-7}$)heterocycloalkyl-, (C$_{3-7}$)cycloalkyl-heteroaryl-, (C$_{3-7}$)cycloalkyl (C$_{1-6}$)alkyl-heteroaryl-, (C$_{4-7}$)cycloalkenyl-heteroaryl-, (C$_{4-9}$)bicycloalkyl-heteroaryl-, (C$_{3-7}$)heterocycloalkyl-heteroaryl-, (C$_3$-C$_7$)heterocycloalkyl(C$_{1-6}$)alkyl-hetero aryl-, (C$_{3-7}$)heterocycloalkenyl-heteroaryl-, (C$_{4-9}$)heterobicycloalkyl-heteroaryl- or (C$_{4-9}$)spiroheterocycloalkyl-heteroaryl-, any of which groups may be optionally substituted by one or more substituents.

Suitably, R$^1$ represents halogen, cyano or —CO$_2$R$^d$; or C$_{1-6}$ alkyl, C$_{2-6}$ alkynyl, aryl, C$_{3-7}$ heterocycloalkyl, C$_{3-7}$ heterocycloalkenyl, heteroaryl, (C$_{3-7}$)heterocycloalkyl-(C$_{1-6}$)alkyl-aryl-, heteroaryl(C$_{3-7}$)heterocycloalkyl-, (C$_{3-7}$) cycloalkyl-heteroaryl-, (C$_{3-7}$)cycloalkyl(C$_{1-6}$)alkyl-hetero aryl-, (C$_{4-7}$)cycloalkenyl-heteroaryl-, (C$_{4-9}$)bicycloalkyl-heteroaryl-, (C$_{3-7}$)heterocycloalkyl-hetero aryl-, (C$_{3-7}$)heterocycloalkyl(C$_{1-6}$)alkyl-heteroaryl-, (C$_{3-7}$)heterocycloalkenyl-heteroaryl-, (C$_{4-9}$)heterobicycloalkyl-heteroaryl- or (C$_{4-9}$)spiroheterocycloalkyl-heteroaryl-, any of which groups may be optionally substituted by one or more substituents.

Generally, R$^1$ represents halogen or cyano; or C$_{1-6}$ alkyl, C$_{2-6}$ alkynyl, aryl, C$_{3-7}$ heterocycloalkyl, C$_{3-7}$ heterocycloalkenyl, heteroaryl, (C$_{3-7}$)heterocycloalkyl(C$_{1-6}$)alkyl-aryl-, heteroaryl(C$_{3-7}$)heterocycloalkyl-, (C$_{3-7}$)cycloalkyl-heteroaryl-, (C$_{3-7}$)cycloalkyl-(C$_{1-6}$)alkyl-hetero aryl-, (C$_{4-7}$) cyclo alkenyl-hetero aryl-, (C$_{4-9}$)bicycloalkyl-heteroaryl-, (C$_{3-7}$)heterocycloalkyl-heteroaryl-, (C$_{3-7}$)heterocycloalkyl (C$_{1-6}$)alkyl-hetero aryl-, (C$_{3-7}$)heterocycloalkenyl-heteroaryl-, (C$_{4-9}$)heterobicycloalkyl-heteroaryl- or (C$_{4-9}$) spiroheterocycloalkyl-heteroaryl-, any of which groups may be optionally substituted by one or more substituents.

More generally, R$^1$ represents halogen; or R$^1$ represents aryl, C$_{3-7}$ heterocycloalkyl, heteroaryl, (C$_{3-7}$)cycloalkyl-heteroaryl-, (C$_{3-7}$)heterocycloalkyl-heteroaryl-, (C$_{4-9}$)heterobicycloalkyl-heteroaryl- or (C$_{4-9}$)spiroheterocycloalkyl-heteroaryl-, any of which groups may be optionally substituted by one or more substituents.

Appositely, R$^1$ represents hydrogen; or R$^1$ represents aryl or heteroaryl, either of which groups may be optionally substituted by one or more substituents.

In a first embodiment, R$^1$ represents hydrogen.

In a second embodiment, R$^1$ represents halogen. In one aspect of that embodiment, R$^1$ represents bromo.

In a third embodiment, R$^1$ represents cyano.

In a fourth embodiment, R$^1$ represents —CO$_2$R$^d$.

In a fifth embodiment, R$^1$ represents optionally substituted C$_{1-6}$ alkyl. In one aspect of that embodiment, R$^1$ represents optionally substituted ethyl.

In a sixth embodiment, R$^1$ represents optionally substituted C$_{2-6}$ alkynyl. In one aspect of that embodiment, R$^1$ represents optionally substituted butynyl.

In a seventh embodiment, R$^1$ represents optionally substituted aryl. In one aspect of that embodiment, R$^1$ represents optionally substituted phenyl.

In an eighth embodiment, $R^1$ represents optionally substituted $C_{3-7}$ heterocycloalkyl.

In a ninth embodiment, $R^1$ represents optionally substituted $C_{3-7}$ heterocycloalkenyl.

In a tenth embodiment, $R^1$ represents optionally substituted heteroaryl. In selected aspects of that embodiment, $R^1$ represents benzofuryl, thienyl, indolyl, pyrazolyl, indazolyl, isoxazolyl, thiazolyl, imidazolyl, pyridinyl, quinolinyl, pyridazinyl, pyrimidinyl or pyrazinyl, any of which groups may be optionally substituted by one or more substituents.

In an eleventh embodiment, $R^1$ represents optionally substituted $(C_{3-7})$-heterocycloalkyl$(C_{1-6})$alkyl-aryl-. In a first aspect of that embodiment, $R^1$ represents optionally substituted pyrrolidinylmethylphenyl-. In a second aspect of that embodiment, $R^1$ represents optionally substituted piperazinylmethylphenyl-.

In a twelfth embodiment, $R^1$ represents optionally substituted heteroaryl$(C_{3-7})$-heterocycloalkyl-. In one aspect of that embodiment, $R^1$ represents optionally substituted pyridinylpiperazinyl-.

In a thirteenth embodiment, $R^1$ represents optionally substituted $(C_{3-7})$cycloalkyl-heteroaryl-. In a first aspect of that embodiment, $R^1$ represents optionally substituted cyclohexylpyrazolyl-. In a second aspect of that embodiment, $R^1$ represents optionally substituted cyclohexylpyridinyl-. In a third aspect of that embodiment, $R^1$ represents optionally substituted cyclopropylpyrimidinyl-. In a fourth aspect of that embodiment, $R^1$ represents optionally substituted cyclobutylpyrimidinyl-. In a fifth aspect of that embodiment, $R^1$ represents optionally substituted cyclopentylpyrimidinyl-. In a sixth aspect of that embodiment, $R^1$ represents optionally substituted cyclohexylpyrimidinyl-. In a seventh aspect of that embodiment, $R^1$ represents optionally substituted cyclohexylpyrazinyl-.

In a fourteenth embodiment, $R^1$ represents optionally substituted $(C_{4-7})$-cycloalkenyl-heteroaryl-.

In a fifteenth embodiment, $R^1$ represents optionally substituted $(C_{3-7})$-heterocycloalkyl-heteroaryl-. In a first aspect of that embodiment, $R^1$ represents optionally substituted pyrrolidinylpyridinyl-. In a second aspect of that embodiment, $R^1$ represents optionally substituted tetrahydropyranylpyridinyl-. In a third aspect of that embodiment, $R^1$ represents optionally substituted piperidinylpyridinyl-. In a fourth aspect of that embodiment, $R^1$ represents optionally substituted piperazinylpyridinyl-. In a fifth aspect of that embodiment, $R^1$ represents optionally substituted morpholinylpyridinyl-. In a sixth aspect of that embodiment, $R^1$ represents optionally substituted thiomorpholinylpyridinyl-. In a seventh aspect of that embodiment, $R^1$ represents optionally substituted diazepanylpyridinyl-. In an eighth aspect of that embodiment, $R^1$ represents optionally substituted oxetanylpyrimidinyl-. In a ninth aspect of that embodiment, $R^1$ represents optionally substituted azetidinylpyrimidinyl-. In a tenth aspect of that embodiment, $R^1$ represents optionally substituted tetrahydrofuranylpyrimidinyl-. In an eleventh aspect of that embodiment, $R^1$ represents optionally substituted pyrrolidinylpyrimidinyl-. In a twelfth aspect of that embodiment, $R^1$ represents optionally substituted tetrahydropyranylpyrimidinyl-. In a thirteenth aspect of that embodiment, $R^1$ represents optionally substituted piperidinylpyrimidinyl-. In a fourteenth aspect of that embodiment, $R^1$ represents optionally substituted piperazinylpyrimidinyl-. In a fifteenth aspect of that embodiment, $R^1$ represents optionally substituted morpholinylpyrimidinyl-. In a sixteenth aspect of that embodiment, $R^1$ represents optionally substituted thiomorpholinylpyrimidinyl-. In a seventeenth aspect of that embodiment, $R^1$ represents optionally substituted azepanylpyrimidinyl-. In an eighteenth aspect of that embodiment, $R^1$ represents optionally substituted oxazepanylpyrimidinyl-. In a nineteenth aspect of that embodiment, $R^1$ represents optionally substituted diazepanylpyrimidinyl-. In a twentieth aspect of that embodiment, $R^1$ represents optionally substituted thiadiazepanylpyrimidinyl-. In a twenty-first aspect of that embodiment, $R^1$ represents optionally substituted oxetanylpyrazinyl-. In a twenty-second aspect of that embodiment, $R^1$ represents optionally substituted piperidinylpyrazinyl-.

In a sixteenth embodiment, $R^1$ represents optionally substituted $(C_{3-7})$-heterocycloalkyl$(C_{1-6})$alkyl-heteroaryl-. In a first aspect of that embodiment, $R^1$ represents optionally substituted morpholinylmethylthienyl-. In a second aspect of that embodiment, $R^1$ represents optionally substituted morpholinylethylpyrazolyl-.

In a seventeenth embodiment, $R^1$ represents optionally substituted $(C_{3-7})$-heterocycloalkenyl-heteroaryl-.

In an eighteenth embodiment, $R^1$ represents optionally substituted $(C_{4-9})$-heterobicycloalkyl-heteroaryl-.

In a nineteenth embodiment, $R^1$ represents optionally substituted $(C_{4-9})$-spiroheterocycloalkyl-heteroaryl-.

In a twentieth embodiment, $R^1$ represents optionally substituted $(C_{3-7})$cycloalkyl-$(C_{1-6})$alkyl-heteroaryl-. In one aspect of that embodiment, $R^1$ represents optionally substituted cyclohexylmethylpyrimidinyl-.

In a twenty-first embodiment, $R^1$ represents optionally substituted $(C_{4-9})$-bicycloalkyl-heteroaryl-.

Appositely, $R^1$ represents hydrogen, bromo, iodo or —$CO_2R^d$; or ethyl, butynyl, phenyl, pyrrolidinyl, piperidinyl, piperazinyl, morpholinyl, 1,2,3,6-tetrahydropyridinyl, benzofuryl, thienyl, indolyl, pyrazolyl, indazolyl, isoxazolyl, thiazolyl, imidazolyl, pyridinyl, quinolinyl, pyridazinyl, pyrimidinyl, pyrazinyl, pyrrolidinylmethylphenyl, piperazinylmethylphenyl, pyridinylpiperazinyl, cyclohexylpyrazolyl, cyclohexylpyridinyl, cyclopropylpyrimidinyl, cyclobutylpyrimidinyl, cyclopentylpyrimidinyl, cyclohexylpyrimidinyl, cyclohexylpyrazinyl, cyclohexylmethylpyrimidinyl, cyclohexenylpyridinyl, cyclohexenylpyrimidinyl, bicyclo[3.1.0]hexanylpyridinyl, bicyclo[3.1.0]hexanylpyrimidinyl, bicyclo[4.1.0]heptanylpyrimidinyl, bicyclo[2.2.2]octanylpyrimidinyl, pyrrolidinylpyridinyl, tetrahydropyranylpyridinyl, piperidinylpyridinyl, piperazinylpyridinyl, morpholinylpyridinyl, thiomorpholinylpyridinyl, diazepanylpyridinyl, oxetanylpyrimidinyl, azetidinylpyrimidinyl, tetrahydrofuranylpyrimidinyl, pyrrolidinylpyrimidinyl, tetrahydropyranylpyrimidinyl, piperidinylpyrimidinyl, piperazinylpyrimidinyl, hexahydro-[1,2,5]thiadiazolo[2,3-c]pyrazinylpyrimidinyl, morpholinylpyrimidinyl, thiomorpholinylpyrimidinyl, azepanylpyrimidinyl, oxazepanylpyrimidinyl, diazepanylpyrimidinyl, thiadiazepanylpyrimidinyl, oxetanylpyrazinyl, piperidinylpyrazinyl, morpholinylmethylthienyl, morpholinylethylpyrazolyl, 3-azabicyclo[3.1.0]-hexanylpyridinyl, 3-azabicyclo[3.1.0]hexanylpyridazinyl, 3-azabicyclo[3.1.0]hexanylpyrimidinyl, 2-oxa-5-azabicyclo[2.2.1]heptanylpyrimidinyl, 3-azabicyclo[3.1.1]heptanylpyrimidinyl, 6-oxa-3-azabicyclo[3.1.1]heptanylpyrimidinyl, 3-azabicyclo[4.1.0]heptanylpyridinyl, 3-azabicyclo[4.1.0]heptanylpyrimidinyl, 2-oxabicyclo[2.2.2]octanylpyrimidinyl, 3-azabicyclo[3.2.1]octanylpyrimidinyl, 8-azabicyclo[3.2.1]octanylpyrimidinyl, 3-oxa-8-azabicyclo[3.2.1]octanylpyrimidinyl, 3,6-diazabicyclo[3.2.2]-nonanylpyrimidinyl, 3-oxa-7-azabicyclo[3.3.1]nonanylpyrimidinyl, 3,7-dioxa-9-azabicyclo[3.3.1]nonanylpyrimidinyl, 5-azaspiro[2.3]hexanylpyrimidinyl, 5-azaspiro-[2.4]heptanylpyrimidinyl, 2-azaspiro[3.3]heptanylpyrimidinyl, 2-oxa-6-azaspiro[3.3]-heptanylpyrimidinyl, 3-oxa-6-azaspiro[3.3]heptanylpyrimidinyl, 6-thia-2-azaspiro[3.3]-heptanylpyrimidinyl, 2-oxa-6-azaspiro[3.4]octanylpyrimidinyl, 2-oxa-6-azaspiro[3.5]-nonanylpyrimidinyl, 2-oxa-7-azaspiro[3.5]nonanylpyrimidinyl or 2,4,8-triazaspiro[4.5]-decanylpyrimidinyl, any of which groups may be optionally substituted by one or more substituents.

Appropriately, $R^1$ represents hydrogen; or $R^1$ represents phenyl or pyrimidinyl, either of which groups may be optionally substituted by one or more substituents.

Typical examples of optional substituents on $R^1$ include one, two or three substituents independently selected from halogen, halo($C_{1-6}$)alkyl, cyano, cyano($C_{1-6}$)alkyl, nitro ($C_{1-6}$)alkyl, $C_{1-6}$ alkyl, trifluoromethyl, difluoroethyl, trifluoroethyl, $C_{2-6}$ alkenyl, hydroxy, hydroxy($C_{1-6}$)alkyl, $C_{1-6}$ alkoxy, trifluoroethoxy, carboxy($C_{3-7}$)cycloalkyloxy, pentafluorothio, $C_{1-6}$ alkylthio, $C_{1-6}$ alkylsulphonyl, ($C_{1-6}$)alkylsulphonyl($C_{1-6}$)alkyl, oxo, amino, amino($C_{1-6}$)alkyl, $C_{1-6}$ alkylamino, di($C_{1-6}$)alkylamino, ($C_{1-6}$)alkoxy($C_{1-6}$)alkylamino, N—[($C_{1-6}$)alkyl]-N-[hydroxy($C_{1-6}$)alkyl]amino, ($C_{2-6}$)alkylcarbonylamino($C_{1-6}$)alkyl, $C_{1-6}$ alkylsulphonylamino, N—[($C_{1-6}$)alkyl]-N—[($C_{1-6}$)alkylsulphonyl]amino, bis[($C_{1-6}$)alkylsulphonyl]amino, N—[($C_{1-6}$)alkyl]-N-[carboxy($C_{1-6}$)alkyl]amino, carboxy($C_{3-7}$)cycloalkylamino, carboxy($C_{3-7}$)cycloalkyl($C_{1-6}$)alkylamino, formyl, $C_{2-6}$ alkylcarbonyl, ($C_{2-6}$)alkyl-carbonyloxy($C_{1-6}$)alkyl, carboxy, carboxy($C_{1-6}$)alkyl, $C_{2-6}$ alkoxycarbonyl, $C_{2-6}$ alkoxycarbonyl($C_{1-6}$)alkyl, morpholinyl($C_{1-6}$)alkoxycarbonyl, $C_{2-6}$ alkoxycarbonylmethylidenyl, a carboxylic acid isostere or prodrug moiety Ω as defined herein, —($C_{1-6}$)alkyl-Ω, aminocarbonyl, aminosulphonyl, ($C_{1-6}$) alkylsulphoximinyl and [($C_{1-6}$)alkyl][N—($C_{1-6}$)alkyl]sulphoximinyl.

Suitable examples of optional substituents on $R^1$ include one, two or three substituents independently selected from hydroxy($C_{1-6}$)alkyl and $C_{1-6}$ alkylsulphonyl.

Typical examples of particular substituents on $R^1$ include one, two or three substituents independently selected from fluoro, chloro, fluoromethyl, fluoroisopropyl, cyano, cyanoethyl, nitromethyl, methyl, ethyl, isopropyl, trifluoromethyl, difluoroethyl, ethenyl, hydroxy, hydroxymethyl, hydroxyisopropyl, methoxy, isopropoxy, trifluoroethoxy, carboxycyclobutyloxy, pentafluorothio, methylthio, methylsulphonyl, methylsulphonylethyl, oxo, amino, aminomethyl, aminoisopropyl, methylamino, dimethylamino, methoxyethylamino, N-(hydroxyethyl)-N-(methyl)amino, acetylaminomethyl, methylsulphonylamino, N-methyl-N-(methylsulphonyl)amino, bis(methylsulphonyl)amino, N-(carboxy ethyl)-N-(methyl)amino, carboxycyclopentylamino, carboxycyclopropylmethylamino, formyl, acetyl, acetoxyisopropyl, carboxy, carboxymethyl, carboxyethyl, methoxycarbonyl, ethoxycarbonyl, n-butoxycarbonyl, tert-butoxycarbonyl, methoxycarbonylmethyl, ethoxycarbonylmethyl, ethoxycarbonylethyl, morpholinylethoxycarbonyl, ethoxycarbonylmethylidenyl, methylsulphonylaminocarbonyl, acetylaminosulphonyl, methoxyaminocarbonyl, tetrazolyl, tetrazolylmethyl, hydroxyoxadiazolyl, aminocarbonyl, aminosulphonyl, methylsulphoximinyl and (methyl)(N-methyl)sulphoximinyl.

Suitable examples of particular substituents on $R^1$ include one, two or three substituents independently selected from hydroxyisopropyl and methylsulphonyl.

In a particular embodiment, $R^1$ is substituted by hydroxy ($C_{1-6}$)alkyl. In one aspect of that embodiment, $R^1$ is substituted by hydroxyisopropyl, especially 2-hydroxyprop-2-yl.

Selected values of $R^1$ include hydrogen, bromo, iodo, —$CO_2R^d$, methoxycarbonylethyl, ethoxycarbonylethyl, hydroxybutynyl, chlorophenyl, hydroxyphenyl, pentafluoro-thiophenyl, methylsulphonylphenyl, aminomethylphenyl, aminoisopropylphenyl, acetyl-aminomethylphenyl, acetylphenyl, methoxycarbonylphenyl, aminocarbonylphenyl, aminosulphonylphenyl, acetylaminosulphonylphenyl, (methoxycarbonyl)(methyl)-pyrrolidinyl, oxopiperidinyl, ethoxycarbonylpiperidinyl, methylsulphonylpiperazinyl, morpholinyl, methylsulphonyl-1,2,3,6-tetrahydropyridinyl, acetyl-1,2,3,6-tetrahydropyridinyl, tert-butoxycarbonyl-1,2, 3,6-tetrahydropyridinyl, methoxycarbonylmethyl-1,2,3,6-tetrahydropyridinyl, benzofuryl, thienyl, indolyl, pyrazolyl, methylpyrazolyl, dimethylpyrazolyl, (methyl)[N-methyl-N-(methylsulfonyl)amino]pyrazolyl, methylindazolyl, dimethylisoxazolyl, hydroxyisopropylthiazolyl, methylimidazolyl, dimethylimidazolyl, pyridinyl, fluoropyridinyl, cyanopyridinyl, methylpyridinyl, (cyano)-(methyl)pyridinyl, dimethylpyridinyl, trifluoromethylpyridinyl, ethenylpyridinyl, hydroxyisopropylpyridinyl, methoxypyridinyl, (methoxy)(methyl)pyridinyl, isopropoxy-pyridinyl, trifluoroethoxypyridinyl, (methyl)(trifluoroethoxy)pyridinyl, methylsulphonyl-pyridinyl, oxopyridinyl, (methyl)(oxo)pyridinyl, (dimethyl)(oxo)pyridinyl, aminopyridinyl, methylaminopyridinyl, dimethylaminopyridinyl, methoxyethylaminopyridinyl, N-(hydroxyethyl)-N-(methyl)aminopyridinyl, methylsulphonylaminopyridinyl, [bis(methylsulphonyl)amino]pyridinyl, carboxypyridinyl, quinolinyl, hydroxypyridazinyl, pyrimidinyl, fluoroisopropylpyrimidinyl, difluoroethylpyrimidinyl, hydroxyisopropylpyrimidinyl, methoxypyrimidinyl, carboxycyclobutyloxypyrimidinyl, methylthio-pyrimidinyl, methylsulphonylpyrimidinyl, oxopyrimidinyl, aminopyrimidinyl, dimethyl-aminopyrimidinyl, methoxyethylaminopyrimidinyl, N-(carboxyethyl)-N-(methyl)aminopyrimidinyl, carboxycyclopentylaminopyrimidinyl, carboxycyclopropylmethylamino-pyrimidinyl, acetoxyisopropylpyrimidinyl, ethoxycarbonylethylpyrimidinyl, hydroxypyrazinyl, hydroxyisopropylpyrazinyl, pyrrolidinylmethylphenyl, piperazinylmethylphenyl, pyridinylpiperazinyl, carboxycyclohexylpyrazolyl, carboxycyclohexyl-pyridinyl, fluoromethylcyclopropylpyrimidinyl, hydroxycyclopropylpyrimidinyl, acetyl-aminomethylcyclopropylpyrimidinyl, hydroxycyclobutylpyrimidinyl, (difluoro)-(hydroxy)cyclobutylpyrimidinyl, carboxycyclopentylpyrimidinyl, carboxycyclohexyl-pyrimidinyl, (carboxy)(methyl)cyclohexylpyrimidinyl, (carboxy)(hydroxy)cyclohexylpyrimidinyl, carboxymethylcyclohexylpyrimidinyl, ethoxycarbonylcyclohexyl-pyrimidinyl, (methoxycarbonyl)(methyl)cyclohexylpyrimidinyl, (ethoxycarbonyl)-(methyl)cyclohexylpyrimidinyl, carboxycyclohexylpyrazinyl, carboxycyclohexylmethyl-pyrimidinyl, carboxycyclohexenylpyridinyl, carboxycyclohexenylpyrimidinyl, ethoxycarbonylcyclohexenylpyrimidinyl, carboxybicyclo[3.1.0]hexanylpyridinyl, carboxybicyclo[3.1.0]hexanylpyrimidinyl, ethoxycarbonylbicyclo[3.1.0]hexanylpyrimidinyl, carboxybicyclo[4.1.0]heptanylpyrimidinyl, carboxybicyclo[2.2.2]octanylpyrimidinyl, pyrrolidinylpyridinyl, hydroxypyrrolidinylpyridinyl, hydroxytetrahydropyranylpyridinyl, piperidinylpyridinyl, acetylpiperidinylpyridinyl, (carboxy)(methyl)piperidinylpyridinyl, [(carboxy)(methyl)piperidinyl](fluoro)pyridinyl, Rcarboxy)(methyl)piperidinylKchloro)pyridinyl, piperazinylpyridinyl, (methyl)-(piperazinyl)pyridinyl, cyanoethylpiperazinylpyridinyl, trifluoroethylpiperazinylpyridinyl, methylsulphonylpiperazinylpyridinyl, methylsulphonylethylpiperazinylpyridinyl, oxopiperazinylpyridinyl, acetylpiperazinylpyridinyl, (tert-butoxycarbonylpiperazinyl)-(methyl)pyridinyl, carboxymethylpiperazinylpyridinyl, carboxyethylpiperazinylpyridinyl, ethoxycarbonylmethylpiperazinylpyridinyl, ethoxycarbonylethylpiperazinylpyridinyl, morpholinylpyridinyl, thiomorpholinylpyridinyl, oxothiomorpholinylpyridinyl, dioxothiomorpholinylpyridinyl, oxodiazepanylpyridinyl, fluorooxetanylpyrimidinyl, hydroxyoxetanylpyrimidinyl, difluoroazetidinylpyrimidinyl, hydroxyazetidinyl-pyrimidinyl, (hydroxy)(methyl)azetidinylpyrimidinyl, (hydroxy)(trifluoromethyl)-azetidinylpyrimidinyl, carboxyazetidinylpyrimidinyl, (tert-butoxycarbonyl)(hydroxy)-azetidinylpyrimidinyl, tetrazolylazetidinylpyrimidinyl, hydroxytetrahydrofuranyl-pyrimidinyl, hydroxypyrrolidinylpyrimidinyl, carboxypyrrolidinylpyrimidinyl, (carboxy)-(methyl)pyrrolidinylpyrimidinyl, carboxymethylpyrrolidinylpyrimidinyl, ethoxycarbonyl-pyrrolidinylpyrimidinyl, fluorotetrahydropyranylpyrimidinyl, hydroxytetrahydropyranyl-pyrimidinyl, difluoropiperidinylpyrimidinyl, (cyano)(methyl)piperidinylpyrimidinyl, (hydroxy)(nitromethyl)piperidinylpyrimidinyl, (hydroxy)(methyl)piperidinylpyrimidinyl, (hydroxy)(trifluoromethyl)piperidinylpyrimidinyl, (hydroxymethyl)(methyl)piperidinylpyrimidinyl, methylsulphonylpiperidinylpyrimidinyl, oxopiperidinylpyrimidinyl, (formyl)(methyl)piperidinylpyrimidinyl, carboxypiperidinylpyrimidinyl, (carboxy)-(fluoro)piperidinylpyrimidinyl, (carboxy)(methyl)piperidinylpyrimidinyl, (carboxy)-(ethyl)piperidinylpyrimidinyl, (carboxy)(trifluoromethyl)piperidinylpyrimidinyl, (carboxy)(hydroxy)piperidinylpyrimidinyl, (carboxy)(hydroxymethyl)piperidinylpyrimidinyl, (carboxy)(methoxy)piperidinylpyrimidinyl, (amino)(carboxy)piperidinylpyrimidinyl, carboxymethylpiperidinylpyrimidinyl, methoxycarbonylpiperidinyl-pyrimidinyl, ethoxycarbonylpiperidinylpyrimidinyl, (ethoxycarbonyl)(fluoro)piperidinylpyrimidinyl, (methoxycarbonyl)(methyl)piperidinylpyrimidinyl, (ethyl)(methoxy-carbonyl)piperidinylpyrimidinyl, (isopropyl)(methoxycarbonyl)piperidinylpyrimidinyl, (ethoxycarbonyl)(methyl)piperidinylpyrimidinyl, (n-butoxycarbonyl)(methyl)piperidinylpyrimidinyl, (ethoxycarbonyl)(trifluoromethyl)piperidinylpyrimidinyl, (ethoxycarbonyl)-(hydroxymethyl)piperidinylpyrimidinyl, (methoxy)(methoxycarbonyl)piperidinylpyrimidinyl, (carboxy)(methoxycarbonyl)piperidinylpyrimidinyl, (methyl)-(morpholinylethoxycarbonyl)piperidinylpyrimidinyl, ethoxycarbonylmethylpiperidinyl-pyrimidinyl, methylsulphonylaminocarbonylpiperidinylpyrimidinyl, acetylaminosulphonylpiperidinylpyrimidinyl, methoxyaminocarbonylpiperidinylpyrimidinyl, tetrazolylpiperidinylpyrimidinyl, hydroxyoxadiazolylpiperidinylpyrimidinyl, amino-sulphonylpiperidinylpyrimidinyl, piperazinylpyrimidinyl, methylsulphonylpiperazinyl-pyrimidinyl, oxopiperazinylpyrimidinyl, carboxypiperazinylpyrimidinyl, carboxyethylpiperazinylpyrimidinyl, tert-butoxycarbonylpiperazinylpyrimidinyl, tetrazolylmethylpiperazinylpyrimidinyl, trioxohexahydro-[1,2,5]thiadiazolo[2,3-c]pyrazinylpyrimidinyl, morpholinylpyrimidinyl, dimethylmorpholinylpyrimidinyl, hydroxymethylmorpholinyl-pyrimidinyl, carboxymorpholinylpyrimidinyl, (carboxy)(methyl)morpholinylpyrimidinyl, carboxymethylmorpholinylpyrimidinyl, thiomorpholinylpyrimidinyl, dioxothiomorpholinylpyrimidinyl, carboxyazepanylpyrimidinyl, carboxyoxazepanyl-pyrimidinyl, oxodiazepanylpyrimidinyl, (oxodiazepanyl)(trifluoromethyl)pyrimidinyl, (oxodiazepanyl)(methoxy)pyrimidinyl, (methyl)(oxo)diazepanylpyrimidinyl, dioxo-thiadiazolylpyrimidinyl, hydroxyoxetanylpyrazinyl, (carboxy)(methyl)piperidinylpyrazinyl, (ethoxycarbonyl)(methyl)piperidinylpyrazinyl, morpholinylmethylthienyl, morpholinylethylpyrazolyl, carboxy-3-azabicyclo[3.1.0]hexanylpyridinyl, carboxy-3-azabicyclo[3.1.0]hexanylpyrimidinyl, carboxy-3-azabicyclo[3.1.0]hexanylpyrimidinyl, (carboxy)(methyl)-3-azabicyclo[3.1.0]hexanylpyrimidinyl, methoxycarbonyl-3-azabicyclo[3.1.0]hexanylpyrimidinyl, ethoxycarbonyl-3-azabicyclo[3.1.0]hexanylpyrimidinyl, 2-oxa-5-azabicyclo[2.2.1]heptanylpyrimidinyl, carboxy-2-oxa-5-azabicyclo-[2.2.1]heptanylpyrimidinyl, carboxy-3-azabicyclo[3.1.1]heptanylpyrimidinyl, 6-oxa-3-azabicyclo[3.1.1]heptanylpyrimidinyl, carboxy-3-azabicyclo[4.1.0]heptanylpyridinyl, carboxy-3-azabicyclo[4.1.0]heptanylpyrimidinyl, methoxycarbonyl-3-azabicyclo[4.1.0]-heptanylpyrimidinyl, ethoxycarbonyl-3-azabicyclo[4.1.0]heptanylpyrimidinyl, (hydroxy)-(methyl)(oxo)-2-oxabicyclo[2.2.2]octanylpyrimidinyl, carboxy-3-azabicyclo[3.2.1]-octanylpyrimidinyl, methoxycarbonyl-3-azabicyclo[3.2.1]octanylpyrimidinyl, oxo-8-azabicyclo[3.2.1]octanylpyrimidinyl, ethoxycarbonylmethylidenyl-8-azabicyclo[3.2.1]-octanylpyrimidinyl, 3-oxa-8-azabicyclo[3.2.1]octanylpyrimidinyl, oxo-3,6-diazabicyclo-[3.2.2]nonanylpyrimidinyl, carboxy-3-oxa-7-azabicyclo[3.3.1]nonanylpyrimidinyl, 3,7-dioxa-9-azabicyclo[3.3.1]nonanylpyrimidinyl, carboxy-5-azaspiro[2.3]hexanylpyrimidinyl, (carboxy)(methyl)-5-azaspiro[2.3]hexanylpyrimidinyl, carboxy-5-azaspiro-[2.4]heptanylpyrimidinyl, carboxy-2-azaspiro[3.3]heptanylpyrimidinyl, 2-oxa-6-azaspiro-[3.3]heptanylpyrimidinyl, 3-oxa-6-azaspiro[3.3]heptanylpyrimidinyl, dioxo-6-thia-2-azaspiro[3.3]heptanylpyrimidinyl, 2-oxa-6-azaspiro[3.4]octanylpyrimidinyl, 2-oxa-6-azaspiro[3.5]nonanylpyrimidinyl, 2-oxa-7-azaspiro[3.5]nonanylpyrimidinyl and (dioxo)(methyl)-2,4,8-triazaspiro[4.5]decanylpyrimidinyl.

Illustrative values of $R^1$ include hydrogen, methylsulphonylphenyl and hydroxyisopropylpyrimidinyl.

Typically, $R^2$ represents hydrogen, halogen, trifluoromethyl or $-OR^a$; or $R^2$ represents optionally substituted $C_{1-6}$ alkyl.

Suitably, $R^2$ represents hydrogen or halogen.

Typical examples of optional substituents on $R^2$ include $C_{2-6}$ alkoxycarbonyl.

Typical examples of particular substituents on $R^2$ include ethoxycarbonyl.

In a first embodiment, $R^2$ represents hydrogen. In a second embodiment, $R^2$ represents halogen. In one aspect of that embodiment, $R^2$ represents fluoro. In another aspect of that embodiment, $R^2$ represents chloro. In a third embodiment, $R^2$ represents trifluoromethyl. In a fourth embodiment, $R^2$ represents $-OR^a$. In a fifth embodiment, $R^2$ represents optionally substituted $C_{1-6}$ alkyl. In one aspect of that embodiment, $R^2$ represents unsubstituted methyl. In another aspect of that embodiment, $R^2$ represents unsubstituted ethyl. In a further aspect of that embodiment, $R^2$ represents monosubstituted methyl or monosubstituted ethyl.

Typical values of $R^2$ include hydrogen, fluoro, chloro, trifluoromethyl, $-OR^a$, methyl and ethoxycarbonylethyl.

Suitable values of $R^2$ include hydrogen and fluoro.

Typically, $R^3$ represents hydrogen, halogen or $C_{1-6}$ alkyl.

In a first embodiment, $R^3$ represents hydrogen. In a second embodiment, $R^3$ represents halogen. In one aspect of that embodiment, $R^3$ represents fluoro. In a third embodiment, $R^3$ represents $C_{1-6}$ alkyl. In one aspect of that embodiment, $R^3$ represents methyl. In another aspect of that embodiment, $R^3$ represents ethyl.

In a particular embodiment, $R^4$ represents hydrogen.

Suitably, $R^5$ represents hydrogen or methyl.

In a first embodiment, $R^5$ represents hydrogen. In a second embodiment, $R^5$ represents $C_{1-6}$ alkyl, especially methyl.

Suitably, $R^6$ represents hydrogen, methyl or ethyl.

In a first embodiment, $R^6$ represents hydrogen. In a second embodiment, $R^6$ represents $C_{1-6}$ alkyl, especially methyl or ethyl. In one aspect of that embodiment, $R^6$ represents methyl. In another aspect of that embodiment, $R^6$ represents ethyl.

Typical examples of suitable substituents on $R^a$, $R^b$, $R^c$, $R^d$ or $R^e$, or on the heterocyclic moiety —$NR^bR^c$, include halogen, $C_{1-6}$ alkyl, $C_{1-6}$ alkoxy, difluoromethoxy, trifluoromethoxy, $C_{1-6}$ alkoxy($C_{1-6}$)alkyl, $C_{1-6}$ alkylthio, $C_{1-6}$ alkylsulphinyl, $C_{1-6}$ alkylsulphonyl, hydroxy, hydroxy($C_{1-6}$) alkyl, amino($C_{1-6}$)alkyl, cyano, trifluoromethyl, oxo, $C_{2-6}$ alkylcarbonyl, carboxy, $C_{2-6}$ alkoxycarbonyl, $C_{2-6}$ alkylcarbonyloxy, amino, $C_{1-6}$ alkylamino, di($C_{1-6}$)alkylamino, phenylamino, pyridinylamino, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulphonylamino, aminocarbonyl, $C_{1-6}$ alkylaminocarbonyl and di($C_{1-6}$)alkylaminocarbonyl.

Typical examples of specific substituents on $R^a$, $R^b$, $R^c$, $R^d$ or $R^e$, or on the heterocyclic moiety —$NR^bR^c$, include fluoro, chloro, bromo, methyl, ethyl, isopropyl, methoxy, isopropoxy, difluoromethoxy, trifluoromethoxy, methoxymethyl, methylthio, ethylthio, methylsulphinyl, methylsulphonyl, hydroxy, hydroxymethyl, hydroxyethyl, aminomethyl, cyano, trifluoromethyl, oxo, acetyl, carboxy, methoxycarbonyl, ethoxycarbonyl, tert-butoxycarbonyl, acetoxy, amino, methylamino, ethylamino, dimethylamino, phenylamino, pyridinylamino, acetylamino, tert-butoxycarbonylamino, acetylaminomethyl, methylsulphonylamino, aminocarbonyl, methylaminocarbonyl and dimethylaminocarbonyl.

Suitably, $R^a$ represents $C_{1-6}$ alkyl, aryl($C_{1-6}$)alkyl or heteroaryl($C_{1-6}$)alkyl, any of which groups may be optionally substituted by one or more substituents.

Selected values of $R^a$ include methyl, ethyl, benzyl and isoindolylpropyl, any of which groups may be optionally substituted by one or more substituents.

Selected examples of suitable substituents on $R^a$ include $C_{1-6}$ alkoxy and oxo.

Selected examples of specific substituents on $R^a$ include methoxy and oxo.

In one embodiment, $R^a$ represents optionally substituted $C_{1-6}$ alkyl. In one aspect of that embodiment, $R^a$ ideally represents unsubstituted $C_{1-6}$ alkyl, especially methyl. In another aspect of that embodiment, $R^a$ ideally represents substituted $C_{1-6}$ alkyl, e.g. methoxyethyl. In another embodiment, $R^a$ represents optionally substituted aryl. In one aspect of that embodiment, $R^a$ represents unsubstituted aryl, especially phenyl. In another aspect of that embodiment, $R^a$ represents monosubstituted aryl, especially methylphenyl. In another embodiment, $R^a$ represents optionally substituted aryl($C_{1-6}$)alkyl, ideally unsubstituted aryl($C_{1-6}$)alkyl, especially benzyl. In a further embodiment, $R^a$ represents optionally substituted heteroaryl. In a further embodiment, $R^a$ represents optionally substituted heteroaryl($C_{1-6}$)alkyl, e.g. dioxoisoindolylpropyl.

Specific values of $R^a$ include methyl, methoxyethyl, benzyl and dioxoisoindolylpropyl.

In a particular aspect, $R^b$ represents hydrogen or trifluoromethyl; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$) alkyl, any of which groups may be optionally substituted by one or more substituents.

Selected values of $R^b$ include hydrogen; or $C_{1-6}$ alkyl, aryl($C_{1-6}$)alkyl, $C_{3-7}$ heterocycloalkyl or $C_{3-7}$ heterocycloalkyl($C_{1-6}$)alkyl, any of which groups may be optionally substituted by one or more substituents.

Typical values of $R^b$ include hydrogen and $C_{1-6}$ alkyl.

Illustratively, $R^b$ represents hydrogen or trifluoromethyl; or methyl, ethyl, n-propyl, isopropyl, n-butyl, 2-methylpropyl, tert-butyl, pentyl, hexyl, cyclopropyl, cyclobutyl, cyclopentyl, cyclohexyl, cyclopropylmethyl, cyclobutylmethyl, cyclopentylmethyl, cyclohexylmethyl, phenyl, benzyl, phenylethyl, azetidinyl, tetrahydrofuryl, tetrahydrothienyl, pyrrolidinyl, piperidinyl, homopiperidinyl, morpholinyl, azetidinylmethyl, tetrahydrofurylmethyl, pyrrolidinylmethyl, pyrrolidinylethyl, pyrrolidinylpropyl, thiazolidinylmethyl, imidazolidinylethyl, piperidinylmethyl, piperidinylethyl, tetrahydroquinolinylmethyl, piperazinylpropyl, morpholinylmethyl, morpholinylethyl, morpholinylpropyl, pyridinyl, indolylmethyl, pyrazolylmethyl, pyrazolylethyl, imidazolylmethyl, imidazolylethyl, benzimidazolylmethyl, triazolylmethyl, pyridinylmethyl or pyridinylethyl, any of which groups may be optionally substituted by one or more substituents.

Representative values of $R^b$ include hydrogen; or methyl, ethyl, n-propyl, benzyl, pyrrolidinyl or morpholinylpropyl, any of which groups may be optionally substituted by one or more substituents.

Selected examples of suitable substituents on $R^b$ include $C_{1-6}$ alkoxy, $C_{1-6}$ alkylthio, $C_{1-6}$ alkylsulphinyl, $C_{1-6}$ alkylsulphonyl, hydroxy, cyano, $C_{2-6}$ alkoxycarbonyl, di-($C_{1-6}$) alkylamino and $C_{2-6}$ alkoxycarbonylamino.

Selected examples of specific substituents on $R^b$ include methoxy, methylthio, methylsulphinyl, methylsulphonyl, hydroxy, cyano, tert-butoxycarbonyl, dimethylamino and tert-butoxycarbonylamino.

Specific values of $R^b$ include hydrogen, methyl, methoxyethyl, methylthioethyl, methylsulphinylethyl, methylsulphonylethyl, hydroxyethyl, cyanoethyl, dimethylaminoethyl, tert-butoxycarbonylaminoethyl, dihydroxypropyl, benzyl, pyrrolidinyl, tert-butoxycarbonylpyrrolidinyl and morpholinylpropyl.

In one embodiment, $R^b$ represents hydrogen. In another embodiment, $R^b$ represents $C_{1-6}$ alkyl, especially methyl.

Selected values of $R^c$ include hydrogen; or $C_{1-6}$ alkyl, $C_{3-7}$ cycloalkyl or $C_{3-7}$ heterocycloalkyl, any of which groups may be optionally substituted by one or more substituents.

In a particular aspect, $R^c$ represents hydrogen, $C_{1-6}$ alkyl or $C_{3-7}$ cycloalkyl.

Representative values of $R^c$ include hydrogen; or methyl, cyclobutyl, cyclopentyl, cyclohexyl, tetrahydropyranyl and piperidinyl, any of which groups may be optionally substituted by one or more substituents.

Selected examples of suitable substituents on $R^c$ include $C_{2-6}$ alkylcarbonyl and $C_{2-6}$ alkoxycarbonyl.

Selected examples of specific substituents on $R^c$ include acetyl and tert-butoxycarbonyl.

Specific values of $R^c$ include hydrogen, methyl, cyclobutyl, cyclopentyl, cyclohexyl, tetrahydropyranyl, acetylpiperidinyl and tert-butoxycarbonylpiperidinyl, Suitably, $R^c$ represents hydrogen or $C_{1-6}$ alkyl. In one embodiment, $R^c$ is hydrogen. In another embodiment, $R^c$ represents $C_{1-6}$ alkyl, especially methyl or ethyl, particularly methyl. In a further embodiment, $R^c$ represents $C_{3-7}$ cycloalkyl, e.g. cyclopropyl, cyclobutyl, cyclopentyl or cyclohexyl.

Alternatively, the moiety —$NR^bR^c$ may suitably represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents.

Selected examples of suitable substituents on the heterocyclic moiety —NR$^b$R$^c$ include C$_{1-6}$ alkyl, C$_{1-6}$ alkylsulphonyl, hydroxy, hydroxy(C$_{1-6}$)alkyl, amino(C$_{1-6}$)alkyl, cyano, oxo, C$_{2-6}$ alkylcarbonyl, carboxy, C$_{2-6}$ alkoxycarbonyl, amino, C$_{2-6}$ alkylcarbonylamino, C$_{2-6}$ alkylcarbonylamino (C$_{1-6}$)alkyl, C$_{2-6}$ alkoxycarbonylamino, C$_{1-6}$ alkylsulphonylamino and aminocarbonyl.

Selected examples of specific substituents on the heterocyclic moiety —NR$^b$R$^c$ include methyl, methylsulphonyl, hydroxy, hydroxymethyl, aminomethyl, cyano, oxo, acetyl, carboxy, ethoxycarbonyl, amino, acetylamino, acetylaminomethyl, tert-butoxycarbonylamino, methylsulphonylamino and aminocarbonyl.

Specific values of the moiety —NR$^b$R$^c$ include azetidin-1-yl, hydroxyazetidin-1-yl, hydroxymethylazetidin-1-yl, (hydroxy)(hydroxymethyl)azetidin-1-yl, aminomethyl-azetidin-1-yl, cyanoazetidin-1-yl, carboxyazetidin-1-yl, aminoazetidin-1-yl, aminocarbonylazetidin-1-yl, pyrrolidin-1-yl, aminomethylpyrrolidin-1-yl, oxopyrrolidin-1-yl, acetylaminomethylpyrrolidin-1-yl, tert-butoxycarbonylaminopyrrolidin-1-yl, oxooxazolidin-3-yl, hydroxyisoxazolidin-2-yl, thiazolidin-3-yl, oxothiazolidin-3-yl, dioxo-isothiazolidin-2-yl, piperidin-1-yl, hydroxypiperidin-1-yl, hydroxymethylpiperidin-1-yl, aminopiperidin-1-yl, acetylaminopiperidin-1-yl, tert-butoxycarbonylaminopiperidin-1-yl, methylsulphonylaminopiperidin-1-yl, morpholin-4-yl, piperazin-1-yl, methylpiperazin-1-yl, methylsulphonylpiperazin-1-yl, oxopiperazin-1-yl, acetylpiperazin-1-yl, ethoxycarbonylpiperazin-1-yl and oxohomopiperazin-1-yl.

Suitably, R$^d$ represents hydrogen; or C$_{1-6}$ alkyl, aryl or heteroaryl, any of which groups may be optionally substituted by one or more substituents.

Selected examples of suitable values for R$^d$ include hydrogen, methyl, ethyl, isopropyl, 2-methylpropyl, tert-butyl, cyclopropyl, cyclobutyl, phenyl, thiazolidinyl, thienyl, imidazolyl and thiazolyl, any of which groups may be optionally substituted by one or more substituents.

Selected examples of suitable substituents on R$^d$ include halogen, C$_{1-6}$ alkyl, C$_{1-6}$ alkoxy, oxo, C$_{2-6}$ alkylcarbonyloxy and di(C$_{1-6}$)alkylamino.

Selected examples of particular substituents on R$^d$ include fluoro, methyl, methoxy, oxo, acetoxy and dimethylamino.

In one embodiment, R$^d$ represents hydrogen. In another embodiment, R$^d$ represents optionally substituted C$_{1-6}$ alkyl. In one aspect of that embodiment, R$^d$ ideally represents unsubstituted C$_{1-6}$ alkyl, e.g. methyl, ethyl, isopropyl, 2-methylpropyl or tert-butyl, especially methyl. In another aspect of that embodiment, R$^d$ ideally represents substituted C$_{1-6}$ alkyl, e.g. substituted methyl or substituted ethyl, including acetoxymethyl, dimethylaminomethyl and trifluoroethyl. In another embodiment, R$^d$ represents optionally substituted aryl. In one aspect of that embodiment, R$^d$ represents unsubstituted aryl, especially phenyl. In another aspect of that embodiment, R$^d$ represents monosubstituted aryl, especially methylphenyl. In a further aspect of that embodiment, R$^d$ represents disubstituted aryl, e.g. dimethoxyphenyl. In a further embodiment, R$^d$ represents optionally substituted heteroaryl, e.g. thienyl, chlorothienyl, methylthienyl, methylimidazolyl or thiazolyl. In another embodiment, R$^d$ represents optionally substituted C$_{3-7}$ cycloalkyl, e.g. cyclopropyl or cyclobutyl. In a further embodiment, R$^d$ represents optionally substituted C$_{3-7}$ heterocycloalkyl, e.g. thiazolidinyl or oxothiazolidinyl.

Selected examples of specific values for R$^d$ include hydrogen, methyl, acetoxymethyl, dimethylaminomethyl, ethyl, trifluoroethyl, isopropyl, 2-methylpropyl, tert-butyl, cyclopropyl, cyclobutyl, phenyl, dimethoxyphenyl, thiazolidinyl, oxothiazolidinyl, thienyl, chlorothienyl, methylthienyl, methylimidazolyl and thiazolyl.

Suitably, R$^e$ represents C$_{1-6}$ alkyl or aryl, either of which groups may be optionally substituted by one or more substituents.

Selected examples of suitable substituents on R$^e$ include C$_{1-6}$ alkyl, especially methyl.

In one embodiment, R$^e$ represents optionally substituted C$_{1-6}$ alkyl, ideally unsubstituted C$_{1-6}$ alkyl, e.g. methyl or propyl, especially methyl. In another embodiment, R$^e$ represents optionally substituted aryl. In one aspect of that embodiment, R$^e$ represents unsubstituted aryl, especially phenyl. In another aspect of that embodiment, R$^e$ represents monosubstituted aryl, especially methylphenyl. In a further embodiment, R$^e$ represents optionally substituted heteroaryl.

Selected values of R$^e$ include methyl, propyl and methylphenyl.

One sub-class of compounds according to the invention is represented by the compounds of formula (IIA) and N-oxides thereof, and pharmaceutically acceptable salts and solvates thereof, and glucuronide derivatives thereof, and co-crystals thereof:

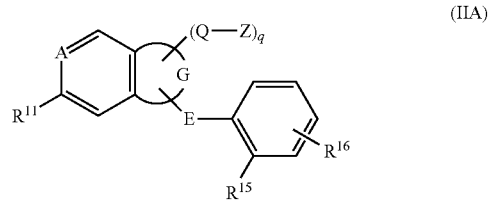

(IIA)

wherein

R$^{11}$ represents halogen or cyano; or R$^{11}$ represents C$_{1-6}$ alkyl, C$_{2-6}$ alkynyl, aryl, C$_{3-7}$ heterocycloalkyl, C$_{3-7}$ heterocycloalkenyl, heteroaryl, (C$_{3-7}$)heterocycloalkyl-(C$_{1-6}$)alkyl-aryl-, heteroaryl(C$_{3-7}$)heterocycloalkyl-, (C$_{3-7}$)cycloalkyl-heteroaryl-, (C$_{3-7}$)cycloalkyl(C$_{1-6}$)alkyl-hetero aryl-, (C$_{4-7}$)cycloalkenyl-heteroaryl-, (C$_{4-9}$)bicycloalkyl-heteroaryl-, (C$_{3-7}$)heterocycloalkyl-hetero aryl-, (C$_{3-7}$)heterocycloalkyl(C$_{1-6}$)alkyl-heteroaryl-, (C$_{3-7}$)heterocycloalkenyl-heteroaryl-, (C$_{4-9}$)heterobicycloalkyl-heteroaryl- or (C$_{4-9}$)spiroheterocycloalkyl-heteroaryl-, any of which groups may be optionally substituted by one or more substituents;

R$^{15}$ and R$^{16}$ independently represent hydrogen, halogen, cyano, nitro, C$_{1-6}$ alkyl, trifluoromethyl, hydroxy, C$_{1-6}$ alkoxy, difluoromethoxy, trifluoromethoxy, C$_{1-6}$ alkylthio, C$_{1-6}$ alkylsulfinyl, C$_{1-6}$ alkylsulfonyl, amino, C$_{1-6}$ alkylamino, di(C$_{1-6}$)alkylamino, arylamino, C$_{2-6}$ alkylcarbonylamino, C$_{1-6}$ alkylsulfonylamino, formyl, C$_{2-6}$ alkylcarbonyl, C$_{3-6}$ cycloalkylcarbonyl, C$_{3-6}$ heterocycloalkylcarbonyl, carboxy, C$_{2-6}$ alkoxycarbonyl, aminocarbonyl, C$_{1-6}$ alkylaminocarbonyl, di(C$_{1-6}$)alkylaminocarbonyl, aminosulfonyl, C$_{1-6}$ alkylaminosulfonyl or di(C$_{1-6}$)alkylaminosulfonyl; and q, A, G, E, Q and Z are as defined above.

Examples of optional substituents which may be present on R$^{11}$ include one, two or three substituents independently selected from halogen, halo(C$_{1-6}$)alkyl, cyano, cyano(C$_{1-6}$)alkyl, nitro, nitro(C$_{1-6}$)alkyl, C$_{1-6}$ alkyl, difluoromethyl, trifluoromethyl, difluoroethyl, trifluoroethyl, $C_{2-6}$ alkenyl, hydroxy, hydroxy($C_{1-6}$)alkyl, $C_{1-6}$ alkoxy, difluoromethoxy, trifluoromethoxy, trifluoroethoxy, carboxy($C_{3-7}$)cycloalkyloxy, $C_{1-3}$ alkylenedioxy, $C_{1-6}$ alkoxy($C_{1-6}$)alkyl, pentafluorothio, $C_{1-6}$ alkylthio, $C_{1-6}$ alkylsulphinyl, $C_{1-6}$ alkylsulphonyl, ($C_{1-6}$)alkylsulphonyl($C_{1-6}$)alkyl, oxo, amino, amino($C_{1-6}$)alkyl, $C_{1-6}$ alkylamino, di($C_{1-6}$)alkylamino, hydroxy($C_{1-6}$)alkylamino, $C_{1-6}$ alkoxyamino, ($C_{1-6}$)alkoxy-($C_{1-6}$)alkyl amino, [($C_{1-6}$)alkoxy](hydroxy)($C_{1-6}$)alkylamino, [($C_{1-6}$)alkylthio](hydroxy)-($C_{1-6}$)alkylamino, N—[($C_{1-6}$)alkyl]-N-[hydroxy($C_{1-6}$)alkyl]amino, di($C_{1-6}$)alkylamino($C_{1-6}$)-alkylamino, N—[di($C_{1-6}$)alkylamino($C_{1-6}$)alkyl]-N-[hydroxy($C_{1-6}$)alkyl]amino, hydroxy-($C_1$-$C_6$)alkyl($C_{3-7}$)cycloalkylamino, (hydroxy)[($C_{3-7}$)cycloalkyl($C_{1-6}$)alkyl]amino, ($C_{3-7}$)heterocycloalkyl($C_{1-6}$)alkylamino, oxo($C_{3-7}$)heterocycloalkyl($C_{1-6}$)alkylamino, ($C_{1-6}$)alkylheteroarylamino, heteroaryl($C_{1-6}$)alkylamino, ($C_{1-6}$)alkylheteroaryl($C_{1-6}$)alkylamino, $C_{2-6}$ alkylcarbonylamino, N—[($C_{1-6}$)alkyl]-N—[($C_{2-6}$)alkylcarbonyl]amino, ($C_{2-6}$)alkylcarbonylamino($C_{1-6}$)alkyl, $C_{3-6}$ alkenylcarbonylamino, bis[($C_{3-6}$)alkenylcarbonyl]amino, N—[($C_{1-6}$)alkyl]-N—[($C_{3-7}$)cycloalkylcarbonyl]amino, $C_{2-6}$ alkoxycarbonylamino, $C_{2-6}$ alkoxycarbonyl($C_{1-6}$)alkylamino, $C_{1-6}$ alkylaminocarbonylamino, $C_{1-6}$ alkylsulphonylamino, N—[($C_{1-6}$)alkyl]-N—[($C_{1-6}$)alkylsulphonyl]amino, bis[($C_{1-6}$)alkylsulphonyl]amino, N—[($C_1$-$C_6$)alkyl]-N-[carboxy($C_{1-6}$)alkyl]amino, carboxy($C_{3-7}$)cycloalkylamino, carboxy-($C_{3-7}$)cycloalkyl($C_{1-6}$)alkylamino, formyl, $C_{2-6}$ alkylcarbonyl, ($C_{3-7}$)cycloalkylcarbonyl, phenylcarbonyl, ($C_{2-6}$)alkylcarbonyloxy($C_{1-6}$)alkyl, carboxy, carboxy($C_{1-6}$)alkyl, $C_{2-6}$ alkoxycarbonyl, $C_{2-6}$ alkoxycarbonyl($C_{1-6}$)alkyl, morpholinyl($C_{1-6}$)alkoxycarbonyl, $C_{2-6}$ alkoxycarbonylmethylidenyl, a carboxylic acid isostere or prodrug moiety Ω as defined herein, —($C_{1-6}$)alkyl-Ω, aminocarbonyl, $C_{1-6}$ alkylaminocarbonyl, hydroxy($C_{1-6}$)alkylaminocarbonyl, di($C_{1-6}$)alkylaminocarbonyl, aminocarbonyl($C_{1-6}$)alkyl, aminosulphonyl, di($C_{1-6}$)alkylaminosulphonyl, ($C_{1-6}$)alkylsulphoximinyl and [($C_{1-6}$)alkyl][N—($C_{1-6}$)alkyl]-sulphoximinyl.

Examples of particular substituents on $R^{11}$ include fluoro, chloro, bromo, fluoromethyl, fluoroisopropyl, cyano, cyanoethyl, nitro, nitromethyl, methyl, ethyl, isopropyl, isobutyl, tert-butyl, difluoromethyl, trifluoromethyl, difluoroethyl, trifluoroethyl, ethenyl, hydroxy, hydroxymethyl, hydroxyisopropyl, methoxy, isopropoxy, difluoromethoxy, trifluoromethoxy, trifluoroethoxy, carboxycyclobutyloxy, methylenedioxy, ethylenedioxy, methoxymethyl, methoxyethyl, pentafluorothio, methylthio, methylsulphinyl, methylsulphonyl, methylsulphonylethyl, oxo, amino, aminomethyl, aminoisopropyl, methylamino, ethylamino, dimethylamino, hydroxyethylamino, hydroxypropylamino, (hydroxy)(methyl)propylamino, methoxyamino, methoxyethylamino, (hydroxy)(methoxy)(methyl)propylamino, (hydroxy)(methylthio)butylamino, N-(hydroxyethyl)-N-(methyl)amino, dimethylaminoethylamino, (dimethylamino)(methyl)-propylamino, N-(dimethylaminoethyl)-N-(hydroxyethyl) amino, hydroxymethyl-cyclopentylamino, hydroxycyclobutylmethylamino, (cyclopropyl)(hydroxy)propylamino, morpholinylethylamino, oxopyrrolidinylmethylamino, ethyloxadiazolylamino, methyl-thiadiazolylamino, thiazolylmethylamino, thiazolylethylamino, pyrimidinylmethylamino, methylpyrazolylmethylamino, acetylamino, N-acetyl-N-methylamino, N-isopropyl-carbonyl-N-methylamino, acetylaminomethyl, ethenylcarbonylamino, bis(ethenyl-carbonyl) amino, N-cyclopropylcarbonyl-N-methylamino, methoxycarbonylamino, ethoxycarbonylamino, tert-butoxycarbonylamino, methoxycarbonylethylamino, ethylaminocarbonylamino, butylaminocarbonylamino, methylsulphonylamino, N-methyl-N-(methylsulphonyl)amino, bis(methylsulphonyl)amino, N-(carboxymethyl)-N-methylamino, N-(carboxyethyl)-N-methylamino, carboxycyclopentylamino, carboxycyclopropylmethylamino, formyl, acetyl, isopropylcarbonyl, cyclobutylcarbonyl, phenylcarbonyl, acetoxyisopropyl, carboxy, carboxymethyl, carboxyethyl, methoxycarbonyl, ethoxycarbonyl, n-butoxycarbonyl, tert-butoxycarbonyl, methoxycarbonylmethyl, ethoxycarbonylmethyl, ethoxycarbonylethyl, morpholinylethoxycarbonyl, ethoxycarbonylmethylidenyl, methylsulphonylaminocarbonyl, acetylaminosulphonyl, methoxyaminocarbonyl, tetrazolyl, tetrazolylmethyl, hydroxyoxadiazolyl, aminocarbonyl, methylamino-carbonyl, hydroxyethylaminocarbonyl, dimethylaminocarbonyl, aminocarbonylmethyl, aminosulphonyl, methylaminosulphonyl, dimethylaminosulphonyl, methylsulphoximinyl and (methyl)(N-methyl)sulphoximinyl.

Generally, $R^{11}$ represents $C_{1-6}$ alkyl, $C_{2-6}$ alkynyl, aryl, $C_{3-7}$ heterocycloalkyl, $C_{3-7}$ heterocycloalkenyl, heteroaryl, ($C_{3-7}$)heterocycloalkyl($C_{1-6}$)alkyl-aryl-, heteroaryl-($C_{3-7}$)heterocycloalkyl-, ($C_{3-7}$)cycloalkyl-heteroaryl-, ($C_{3-7}$)cycloalkyl($C_{1-6}$)alkyl-heteroaryl-, ($C_{4-7}$)cycloalkenyl-heteroaryl-, ($C_{4-9}$) bicycloalkyl-heteroaryl-, ($C_{3-7}$) heterocycloalkyl-heteroaryl-, ($C_{3-7}$)heterocycloalkyl($C_{1-6}$) alkyl-hetero aryl-, ($C_{3-7}$)heterocycloalkenyl-heteroaryl-, ($C_{4-9}$)heterobicycloalkyl-heteroaryl- or ($C_{4-9}$)spiroheterocycloalkyl-heteroaryl-, any of which groups may be optionally substituted by one or more substituents.

More generally, $R^{11}$ represents halogen; or $R^{11}$ represents aryl, $C_{3-7}$ heterocycloalkyl, heteroaryl, ($C_{3-7}$)cycloalkyl-heteroaryl-, ($C_{3-7}$)heterocycloalkyl-heteroaryl-, ($C_{4-9}$)heterobicycloalkyl-heteroaryl- or ($C_{4-9}$)spiroheterocycloalkyl-heteroaryl-, any of which groups may be optionally substituted by one or more substituents.

Appositely, $R^{11}$ represents aryl or heteroaryl, either of which groups may be optionally substituted by one or more substituents.

In a first embodiment, $R^{11}$ represents halogen. In one aspect of that embodiment, $R^{11}$ represents bromo. In one aspect of that embodiment, $R^{11}$ represents iodo.

In a second embodiment, $R^{11}$ represents cyano.

In a third embodiment, $R^{11}$ represents optionally substituted $C_{1-6}$ alkyl. In one aspect of that embodiment, $R^{11}$ represents optionally substituted ethyl.

In a fourth embodiment, $R^{11}$ represents optionally substituted $C_{2-6}$ alkynyl. In one aspect of that embodiment, $R^{11}$ represents optionally substituted butynyl.

In a fifth embodiment, $R^{11}$ represents optionally substituted aryl. In one aspect of that embodiment, $R^{11}$ represents optionally substituted phenyl.

In a sixth embodiment, $R^{11}$ represents optionally substituted $C_{3-7}$ heterocycloalkyl.

In a seventh embodiment, $R^{11}$ represents optionally substituted $C_{3-7}$ heterocycloalkenyl.

In an eighth embodiment, $R^{11}$ represents optionally substituted heteroaryl. In selected aspects of that embodiment, $R^{11}$ represents benzofuryl, thienyl, indolyl, pyrazolyl, indazolyl, isoxazolyl, thiazolyl, imidazolyl, pyridinyl, quinolinyl, pyridazinyl, pyrimidinyl or pyrazinyl, any of which groups may be optionally substituted by one or more substituents.

In a ninth embodiment, $R^{11}$ represents optionally substituted ($C_{3-7}$)-heterocycloalkyl($C_{1-6}$)alkyl-aryl-. In a first aspect of that embodiment, $R^{11}$ represents optionally substituted pyrrolidinylmethylphenyl-. In a second aspect of that embodiment, $R^{11}$ represents optionally substituted piperazinylmethylphenyl-.

In a tenth embodiment, $R^{11}$ represents optionally substituted heteroaryl($C_{3-7}$)-heterocycloalkyl-. In one aspect of that embodiment, $R^{11}$ represents optionally substituted pyridinylpiperazinyl-.

In an eleventh embodiment, $R^{11}$ represents optionally substituted ($C_{3-7}$)cycloalkyl-heteroaryl-. In a first aspect of that embodiment, $R^{11}$ represents optionally substituted cyclohexylpyrazolyl-. In a second aspect of that embodiment, $R^{11}$ represents optionally substituted cyclohexylpyridinyl-. In a third aspect of that embodiment, $R^{11}$ represents optionally substituted cyclopropylpyrimidinyl-. In a fourth aspect of that embodiment, $R^{11}$ represents optionally substituted cyclobutylpyrimidinyl-. In a fifth aspect of that embodiment, $R^{11}$ represents optionally substituted cyclopentylpyrimidinyl-. In a sixth aspect of that embodiment, $R^{11}$ represents optionally substituted cyclohexylpyrimidinyl-. In a seventh aspect of that embodiment, $R^{11}$ represents optionally substituted cyclohexylpyrazinyl-.

In a twelfth embodiment, $R^{11}$ represents optionally substituted ($C_{4-7}$)cycloalkenyl-heteroaryl-.

In a thirteenth embodiment, $R^{11}$ represents optionally substituted ($C_{3-7}$)-heterocycloalkyl-heteroaryl-. In a first aspect of that embodiment, $R^{11}$ represents optionally substituted pyrrolidinylpyridinyl-. In a second aspect of that embodiment, $R^{11}$ optionally substituted tetrahydropyranylpyridinyl-. In a third aspect of that embodiment, $R^{11}$ represents optionally substituted piperidinylpyridinyl-. In a fourth aspect of that embodiment, $R^{11}$ represents optionally substituted piperazinylpyridinyl-. In a fifth aspect of that embodiment, $R^{11}$ represents optionally substituted morpholinylpyridinyl-. In a sixth aspect of that embodiment, $R^{11}$ represents optionally substituted thiomorpholinylpyridinyl-. In a seventh aspect of that embodiment, $R^{11}$ represents optionally substituted diazepanylpyridinyl-. In an eighth aspect of that embodiment, $R^{11}$ represents optionally substituted oxetanylpyrimidinyl-. In a ninth aspect of that embodiment, $R^{11}$ represents optionally substituted azetidinylpyrimidinyl-. In a tenth aspect of that embodiment, $R^{11}$ represents optionally substituted tetrahydrofuranylpyrimidinyl-. In an eleventh aspect of that embodiment, $R^{11}$ represents optionally substituted pyrrolidinylpyrimidinyl-. In a twelfth aspect of that embodiment, $R^{11}$ represents optionally substituted tetrahydropyranylpyrimidinyl-. In a thirteenth aspect of that embodiment, $R^{11}$ represents optionally substituted piperidinylpyrimidinyl-. In a fourteenth aspect of that embodiment, $R^{11}$ represents optionally substituted piperazinylpyrimidinyl-. In a fifteenth aspect of that embodiment, $R^{11}$ represents optionally substituted morpholinylpyrimidinyl-. In a sixteenth aspect of that embodiment, $R^{11}$ represents optionally substituted thiomorpholinylpyrimidinyl-. In a seventeenth aspect of that embodiment, $R^{11}$ represents optionally substituted azepanylpyrimidinyl-. In an eighteenth aspect of that embodiment, $R^{11}$ represents optionally substituted oxazepanylpyrimidinyl-. In a nineteenth aspect of that embodiment, $R^{11}$ represents optionally substituted diazepanylpyrimidinyl-. In a twentieth aspect of that embodiment, $R^{11}$ represents optionally substituted thiadiazepanylpyrimidinyl-. In a twenty-first aspect of that embodiment, $R^{11}$ represents optionally substituted oxetanylpyrazinyl-. In a twenty-second aspect of that embodiment, $R^{11}$ represents optionally substituted piperidinylpyrazinyl-.

In a fourteenth embodiment, $R^{11}$ represents optionally substituted ($C_{3-7}$)-heterocycloalkyl($C_{1-6}$)alkyl-heteroaryl-. In a first aspect of that embodiment, $R^{11}$ represents optionally substituted morpholinylmethylthienyl-. In a second aspect of that embodiment, $R^{11}$ represents optionally substituted morpholinylethylpyrazolyl-.

In a fifteenth embodiment, $R^{11}$ represents optionally substituted ($C_{3-7}$)-heterocycloalkenyl-heteroaryl-.

In a sixteenth embodiment, $R^{11}$ represents optionally substituted ($C_{4-9}$)-heterobicycloalkyl-heteroaryl-.

In a seventeenth embodiment, $R^{11}$ represents optionally substituted ($C_{4-9}$)-spiroheterocycloalkyl-heteroaryl-.

In an eighteenth embodiment, $R^{11}$ represents optionally substituted ($C_{3-7}$)-cycloalkyl($C_{1-6}$)alkyl-heteroaryl-. In one aspect of that embodiment, $R^{11}$ represents optionally substituted cyclohexylmethylpyrimidinyl-.

In a nineteenth embodiment, $R^{11}$ represents optionally substituted ($C_{4-9}$)-bicycloalkyl-heteroaryl-.

Appositely, $R^{11}$ represents bromo or iodo; or $R^{11}$ represents ethyl, butynyl, phenyl, pyrrolidinyl, piperidinyl, piperazinyl, morpholinyl, 1,2,3,6-tetrahydropyridinyl, benzofuryl, thienyl, indolyl, pyrazolyl, indazolyl, isoxazolyl, thiazolyl, imidazolyl, pyridinyl, quinolinyl, pyridazinyl, pyrimidinyl, pyrazinyl, pyrrolidinylmethylphenyl, piperazinylmethylphenyl, pyridinylpiperazinyl, cyclohexylpyrazolyl, cyclohexylpyridinyl, cyclopropylpyrimidinyl, cyclobutylpyrimidinyl, cyclopentylpyrimidinyl, cyclohexylpyrimidinyl, cyclohexylpyrazinyl, cyclohexylmethylpyrimidinyl, cyclohexenylpyridinyl, cyclohexenylpyrimidinyl, bicyclo[3.1.0]hexanylpyridinyl, bicyclo[3.1.0]hexanylpyrimidinyl, bicyclo[4.1.0]heptanylpyrimidinyl, bicyclo[2.2.2]octanylpyrimidinyl, pyrrolidinylpyridinyl, tetrahydropyranylpyridinyl, piperidinylpyridinyl, piperazinylpyridinyl, morpholinylpyridinyl, thiomorpholinylpyridinyl, diazepanylpyridinyl, oxetanylpyrimidinyl, azetidinylpyrimidinyl, tetrahydrofuranylpyrimidinyl, pyrrolidinylpyrimidinyl, tetrahydropyranylpyrimidinyl, piperidinylpyrimidinyl, piperazinylpyrimidinyl, hexahydro-[1,2,5]thiadiazolo[2,3-c]pyrazinylpyrimidinyl, morpholinylpyrimidinyl, thiomorpholinylpyrimidinyl, azepanylpyrimidinyl, oxazepanylpyrimidinyl, diazepanylpyrimidinyl, thiadiazepanylpyrimidinyl, oxetanylpyrazinyl, piperidinylpyrazinyl, morpholinylmethylthienyl, morpholinylethylpyrazolyl, 3-azabicyclo[3.1.0]-hexanylpyridinyl, 3-azabicyclo[3.1.0]hexanylpyridazinyl, 3-azabicyclo[3.1.0]hexanylpyrimidinyl, 2-oxa-5-azabicyclo[2.2.1]heptanylpyrimidinyl, 3-azabicyclo[3.1.1]heptanylpyrimidinyl, 6-oxa-3-azabicyclo[3.1.1]heptanylpyrimidinyl, 3-azabicyclo[4.1.0]heptanylpyridinyl, 3-azabicyclo[4.1.0]heptanylpyrimidinyl, 2-oxabicyclo[2.2.2]octanylpyrimidinyl, 3-azabicyclo[3.2.1]octanylpyrimidinyl, 8-azabicyclo[3.2.1]octanylpyrimidinyl, 3-oxa-8-azabicyclo[3.2.1]octanylpyrimidinyl, 3,6-diazabicyclo[3.2.2]-nonanylpyrimidinyl, 3-oxa-7-azabicyclo[3.3.1]nonanylpyrimidinyl, 3,7-dioxa-9-azabicyclo[3.3.1]nonanylpyrimidinyl, 5-azaspiro[2.3]hexanylpyrimidinyl, 5-azaspiro-[2.4]heptanylpyrimidinyl, 2-azaspiro[3.3]heptanylpyrimidinyl, 2-oxa-6-azaspiro[3.3]-heptanylpyrimidinyl, 3-oxa-6-azaspiro[3.3]heptanylpyrimidinyl, 6-thia-2-azaspiro[3.3]-heptanylpyrimidinyl, 2-oxa-6-azaspiro[3.4]octanylpyrimidinyl, 2-oxa-6-azaspiro[3.5]-nonanylpyrimidinyl, 2-oxa-7-azaspiro[3.5]nonanylpyrimidinyl or 2,4,8-triazaspiro[4.5]-decanylpyrimidinyl, any of which groups may be optionally substituted by one or more substituents.

Appropriately, $R^{11}$ represents phenyl or pyrimidinyl, either of which groups may be optionally substituted by one or more substituents.

Typical examples of optional substituents on $R^{11}$ include one, two or three substituents independently selected from halogen, halo($C_{1-6}$)alkyl, cyano, cyano($C_{1-6}$)alkyl, nitro ($C_{1-6}$)alkyl, $C_{1-6}$ alkyl, trifluoromethyl, difluoroethyl, trifluoroethyl, $C_{2-6}$ alkenyl, hydroxy, hydroxy($C_{1-6}$)alkyl, $C_{1-6}$ alkoxy, trifluoroethoxy, carboxy($C_{3-7}$)cycloalkyloxy, pentafluorothio, $C_{1-6}$ alkylthio, $C_{1-6}$ alkylsulphonyl, ($C_{1-6}$)alkylsulphonyl($C_{1-6}$)alkyl, oxo, amino, amino($C_{1-6}$)alkyl, $C_{1-6}$ alkylamino, di($C_{1-6}$)alkylamino, ($C_{1-6}$)alkoxy($C_{1-6}$)alkylamino, N—[($C_{1-6}$)alkyl]-N-[hydroxy($C_{1-6}$)alkyl]amino, ($C_{2-6}$)alkylcarbonylamino($C_{1-6}$)alkyl, $C_{1-6}$ alkylsulphonylamino, N—[($C_{1-6}$)alkyl]-N—[($C_{1-6}$)alkylsulphonyl]amino, bis[($C_{1-6}$)alkylsulphonyl]amino, N—[($C_{1-6}$)alkyl]-N-[carboxy($C_{1-6}$)alkyl]amino, carboxy($C_{3-7}$)cycloalkylamino, carboxy($C_{3-7}$)cycloalkyl($C_{1-6}$)alkylamino, formyl, $C_{2-6}$ alkylcarbonyl, ($C_{2-6}$)alkyl-carbonyloxy($C_{1-6}$)alkyl, carboxy, carboxy($C_{1-6}$)alkyl, $C_{2-6}$ alkoxycarbonyl, $C_{2-6}$ alkoxycarbonyl($C_{1-6}$)alkyl, morpholinyl($C_{1-6}$)alkoxycarbonyl, $C_{2-6}$ alkoxycarbonylmethylidenyl, a carboxylic acid isostere or prodrug moiety Ω as defined herein, —($C_{1-6}$)alkyl-Ω, aminocarbonyl, aminosulphonyl, ($C_{1-6}$) alkylsulphoximinyl and [($C_{1-6}$)alkyl][N—($C_{1-6}$)alkyl]sulphoximinyl.

Suitable examples of optional substituents on $R^{11}$ include one, two or three substituents independently selected from hydroxy($C_{1-6}$)alkyl and $C_{1-6}$ alkylsulphonyl.

Typical examples of particular substituents on $R^{11}$ include one, two or three substituents independently selected from fluoro, chloro, fluoromethyl, fluoroisopropyl, cyano, cyanoethyl, nitromethyl, methyl, ethyl, isopropyl, trifluoromethyl, difluoroethyl, ethenyl, hydroxy, hydroxymethyl, hydroxyisopropyl, methoxy, isopropoxy, trifluoroethoxy, carboxycyclobutyloxy, pentafluorothio, methylthio, methylsulphonyl, methylsulphonylethyl, oxo, amino, aminomethyl, aminoisopropyl, methylamino, dimethylamino, methoxyethylamino, N-(hydroxyethyl)-N-(methyl)amino, acetylaminomethyl, methylsulphonylamino, N-methyl-N-(methylsulphonyl) amino, bis(methylsulphonyl)amino, N-(carboxy ethyl)-N-(methyl)amino, carboxycyclopentylamino, carboxycyclopropylmethylamino, formyl, acetyl, acetoxyisopropyl, carboxy, carboxymethyl, carboxyethyl, methoxy-carbonyl, ethoxycarbonyl, n-butoxycarbonyl, tert-butoxycarbonyl, methoxycarbonylmethyl, ethoxycarbonylmethyl, ethoxycarbonylethyl, morpholinylethoxycarbonyl, ethoxycarbonylmethylidenyl, methylsulphonylaminocarbonyl, acetylaminosulphonyl, methoxyaminocarbonyl, tetrazolyl, tetrazolylmethyl, hydroxyoxadiazolyl, aminocarbonyl, aminosulphonyl, methylsulphoximinyl and (methyl)(N-methyl)sulphoximinyl.

Suitable examples of particular substituents on $R^{11}$ include one, two or three substituents independently selected from hydroxyisopropyl and methylsulphonyl.

In a particular embodiment, $R^{11}$ is substituted by hydroxy ($C_{1-6}$)alkyl. In one aspect of that embodiment, $R^{11}$ is substituted by hydroxyisopropyl, especially 2-hydroxyprop-2-yl.

Selected values of $R^{11}$ include bromo, iodo, methoxycarbonylethyl, ethoxycarbonylethyl, hydroxybutynyl, chlorophenyl, hydroxyphenyl, pentafluoro-thiophenyl, methylsulphonylphenyl, aminomethylphenyl, aminoisopropylphenyl, acetyl-aminomethylphenyl, acetylphenyl, methoxycarbonylphenyl, aminocarbonylphenyl, aminosulphonylphenyl, acetylaminosulphonylphenyl, (methoxycarbonyl)(methyl)-pyrrolidinyl, oxopiperidinyl, ethoxycarbonylpiperidinyl, methylsulphonylpiperazinyl, morpholinyl, methylsulphonyl-1,2,3,6-tetrahydropyridinyl, acetyl-1,2,3,6-tetrahydropyridinyl, tert-butoxycarbonyl-1,2,3,6-tetrahydropyridinyl, methoxycarbonylmethyl-1,2,3,6-tetrahydropyridinyl, benzofuryl, thienyl, indolyl, pyrazolyl, methylpyrazolyl, dimethylpyrazolyl, (methyl)[N-methyl-N-(methylsulfonyl) amino]pyrazolyl, methylindazolyl, dimethylisoxazolyl, hydroxyisopropylthiazolyl, methylimidazolyl, dimethylimidazolyl, pyridinyl, fluoropyridinyl, cyanopyridinyl, methylpyridinyl, (cyano)-(methyl)pyridinyl, dimethylpyridinyl, trifluoromethylpyridinyl, ethenylpyridinyl, hydroxyisopropylpyridinyl, methoxypyridinyl, (methoxy)(methyl)pyridinyl, isopropoxy-pyridinyl, trifluoroethoxypyridinyl, (methyl)(trifluoroethoxy)pyridinyl, methylsulphonyl-pyridinyl, oxopyridinyl, (methyl)(oxo)pyridinyl, (dimethyl)(oxo)pyridinyl, aminopyridinyl, methylaminopyridinyl, dimethylaminopyridinyl, methoxyethylaminopyridinyl, N-(hydroxyethyl)-N-(methyl)aminopyridinyl, methylsulphonylaminopyridinyl, [bis(methylsulphonyl)amino]pyridinyl, carboxypyridinyl, quinolinyl, hydroxypyridazinyl, pyrimidinyl, fluoroisopropylpyrimidinyl, difluoroethylpyrimidinyl, hydroxyisopropylpyrimidinyl, methoxypyrimidinyl, carboxycyclobutyloxypyrimidinyl, methylthio-pyrimidinyl, methylsulphonylpyrimidinyl, oxopyrimidinyl, aminopyrimidinyl, dimethyl-aminopyrimidinyl, methoxyethylaminopyrimidinyl, N-(carboxyethyl)-N-(methyl)aminopyrimidinyl, carboxycyclopentylaminopyrimidinyl, carboxycyclopropylmethylamino-pyrimidinyl, acetoxyisopropylpyrimidinyl, ethoxycarbonylethylpyrimidinyl, hydroxypyrazinyl, hydroxyisopropylpyrazinyl, pyrrolidinylmethylphenyl, piperazinylmethylphenyl, pyridinylpiperazinyl, carboxycyclohexylpyrazolyl, carboxycyclohexyl-pyridinyl, fluoromethylcyclopropylpyrimidinyl, hydroxycyclopropylpyrimidinyl, acetyl-aminomethylcyclopropylpyrimidinyl, hydroxycyclobutylpyrimidinyl, (difluoro)-(hydroxy)cyclobutylpyrimidinyl, carboxycyclopentylpyrimidinyl, carboxycyclohexyl-pyrimidinyl, (carboxy)(methyl)cyclohexylpyrimidinyl, (carboxy)(hydroxy)cyclohexylpyrimidinyl, carboxymethylcyclohexylpyrimidinyl, ethoxycarbonylcyclohexyl-pyrimidinyl, (methoxycarbonyl)(methyl)cyclohexylpyrimidinyl, (ethoxycarbonyl)-(methyl)cyclohexylpyrimidinyl, carboxycyclohexylpyrazinyl, carboxycyclohexylmethyl-pyrimidinyl, carboxycyclohexenylpyridinyl, carboxycyclohexenylpyrimidinyl, ethoxycarbonylcyclohexenylpyrimidinyl, carboxybicyclo[3.1.0]hexanylpyridinyl, carboxybicyclo[3.1.0]hexanylpyrimidinyl, ethoxycarbonylbicyclo[3.1.0]hexanylpyrimidinyl, carboxybicyclo[4.1.0]heptanylpyrimidinyl, carboxybicyclo[2.2.2]octanylpyrimidinyl, pyrrolidinylpyridinyl, hydroxypyrrolidinylpyridinyl, hydroxytetrahydropyranylpyridinyl, piperidinylpyridinyl, acetylpiperidinylpyridinyl, (carboxy)(methyl)piperidinylpyridinyl, [(carboxy)(methyl)piperidinyl](fluoro)pyridinyl, Rcarboxy)(methyl)piperidinylKchloro)pyridinyl, piperazinylpyridinyl, (methyl)-(piperazinyl)pyridinyl, cyanoethylpiperazinylpyridinyl, trifluoroethylpiperazinylpyridinyl, methylsulphonylpiperazinylpyridinyl, methylsulphonylethylpiperazinylpyridinyl, oxopiperazinylpyridinyl, acetylpiperazinylpyridinyl, (tert-butoxycarbonylpiperazinyl)-(methyl)pyridinyl, carboxymethylpiperazinylpyridinyl, carboxyethylpiperazinylpyridinyl, ethoxycarbonylmethylpiperazinylpyridinyl, ethoxycarbonylethylpiperazinylpyridinyl, morpholinylpyridinyl, thiomorpholinylpyridinyl, oxothiomorpholinylpyridinyl, dioxothiomorpholinylpyridinyl, oxodiazepanylpyridinyl, fluorooxetanylpyrimidinyl, hydroxyoxetanylpyrimidinyl, difluoroazetidinylpyrimidinyl, hydroxyazetidinyl-pyrimidinyl, (hydroxy)(methyl)azetidinylpyrimidinyl, (hydroxy)(trifluoromethyl)-azetidinylpyrimidinyl, carboxyazetidinylpyrimidinyl, (tert-butoxycarbonyl)(hydroxy)-azetidinylpyrimidinyl, tetrazolylazetidinylpyrimidinyl, hydroxytetrahydrofuranylpyrimidinyl, hydroxypyrrolidinylpyrimidinyl, carboxypyrrolidinylpyrimidinyl, (carboxy)-(methyl)pyrrolidinylpyrimidinyl, carboxymethylpyrrolidinylpyrimidinyl, ethoxycarbonyl-pyrrolidinylpyrimidinyl, fluorotetrahydropyranylpyrimidinyl, hydroxytetrahydropyranyl-pyrimidinyl, difluoropiperidinylpyrimidinyl, (cyano)(methyl)piperidinylpyrimidinyl, (hydroxy)(nitromethyl)piperidinylpyrimidinyl, (hydroxy)(methyl)piperidinylpyrimidinyl, (hydroxy)(trifluoromethyl)piperidinylpyrimidinyl, (hydroxymethyl)(methyl)piperidinylpyrimidinyl, methylsulphonylpiperidinylpyrimidinyl, oxopiperidinylpyrimidinyl, (formyl)(methyl)piperidinylpyrimidinyl, carboxypiperidinylpyrimidinyl, (carboxy)-(fluoro)piperidinylpyrimidinyl, (carboxy)(methyl)piperidinylpyrimidinyl, (carboxy)-(ethyl)piperidinylpyrimidinyl, (carboxy)(trifluoromethyl)piperidinylpyrimidinyl, (carboxy)(hydroxy)piperidinylpyrimidinyl, (carboxy)(hydroxymethyl)piperidinylpyrimidinyl, (carboxy)(methoxy)piperidinylpyrimidinyl, (amino)(carboxy)piperidinylpyrimidinyl, carboxymethylpiperidinylpyrimidinyl, methoxycarbonylpiperidinyl-pyrimidinyl, ethoxycarbonylpiperidinylpyrimidinyl, (ethoxycarbonyl)(fluoro)piperidinylpyrimidinyl, (methoxycarbonyl)(methyl)piperidinylpyrimidinyl, (ethyl)(methoxy-carbonyl)piperidinylpyrimidinyl, (isopropyl)(methoxycarbonyl)piperidinylpyrimidinyl, (ethoxycarbonyl)(methyl)piperidinylpyrimidinyl, (n-butoxycarbonyl)(methyl)piperidinylpyrimidinyl, (ethoxycarbonyl)(trifluoromethyl)piperidinylpyrimidinyl, (ethoxycarbonyl)-(hydroxymethyl)piperidinylpyrimidinyl, (methoxy)(methoxycarbonyl)piperidinylpyrimidinyl, (carboxy)(methoxycarbonyl)piperidinylpyrimidinyl, (methyl)-(morpholinylethoxycarbonyl)piperidinylpyrimidinyl, ethoxycarbonylmethylpiperidinyl-pyrimidinyl, methylsulphonylaminocarbonylpiperidinylpyrimidinyl, acetylaminosulphonylpiperidinylpyrimidinyl, methoxyaminocarbonylpiperidinylpyrimidinyl, tetrazolylpiperidinylpyrimidinyl, hydroxyoxadiazolylpiperidinylpyrimidinyl, amino-sulphonylpiperidinylpyrimidinyl, piperazinylpyrimidinyl, methylsulphonylpiperazinyl-pyrimidinyl, oxopiperazinylpyrimidinyl, carboxypiperazinylpyrimidinyl, carboxyethylpiperazinylpyrimidinyl, tert-butoxycarbonylpiperazinylpyrimidinyl, tetrazolylmethylpiperazinylpyrimidinyl, trioxohexahydro-[1,2,5]thiadiazolo[2,3-c]pyrazinylpyrimidinyl, morpholinylpyrimidinyl, dimethylmorpholinylpyrimidinyl, hydroxymethylmorpholinyl-pyrimidinyl, carboxymorpholinylpyrimidinyl, (carboxy)(methyl)morpholinylpyrimidinyl, carboxymethylmorpholinylpyrimidinyl, thiomorpholinylpyrimidinyl, dioxothiomorpholinylpyrimidinyl, carboxyazepanylpyrimidinyl, carboxyoxazepanyl-pyrimidinyl, oxodiazepanylpyrimidinyl, (oxodiazepanyl)(trifluoromethyl)pyrimidinyl, (oxodiazepanyl)(methoxy)pyrimidinyl, (methyl)(oxo)diazepanylpyrimidinyl, dioxo-thiadiazepanylpyrimidinyl, hydroxyoxetanylpyrazinyl, (carboxy)(methyl)piperidinylpyrazinyl, (ethoxycarbonyl)(methyl)piperidinylpyrazinyl, morpholinylmethylthienyl, morpholinylethylpyrazolyl, carboxy-3-azabicyclo[3.1.0]hexanylpyridinyl, carboxy-3-azabicyclo[3.1.0]hexanylpyridazinyl, carboxy-3-azabicyclo[3.1.0]hexanylpyrimidinyl, (carboxy)(methyl)-3-azabicyclo[3.1.0]hexanylpyrimidinyl, methoxycarbonyl-3-azabicyclo[3.1.0]hexanylpyrimidinyl, ethoxycarbonyl-3-azabicyclo[3.1.0]hexanylpyrimidinyl, 2-oxa-5-azabicyclo[2.2.1]heptanylpyrimidinyl, carboxy-2-oxa-5-azabicyclo-[2.2.1]heptanylpyrimidinyl, carboxy-3-azabicyclo[3.1.1]heptanylpyrimidinyl, 6-oxa-3-azabicyclo[3.1.1]heptanylpyrimidinyl, carboxy-3-azabicyclo[4.1.0]heptanylpyridinyl, carboxy-3-azabicyclo[4.1.0]heptanylpyrimidinyl, methoxycarbonyl-3-azabicyclo[4.1.0]-heptanylpyrimidinyl, ethoxycarbonyl-3-azabicyclo[4.1.0]heptanylpyrimidinyl, (hydroxy)-(methyl)(oxo)-2-oxabicyclo[2.2.2]octanylpyrimidinyl, carboxy-3-azabicyclo[3.2.1]-octanylpyrimidinyl, methoxycarbonyl-3-azabicyclo[3.2.1]octanylpyrimidinyl, oxo-8-azabicyclo[3.2.1]octanylpyrimidinyl, ethoxycarbonylmethylidenyl-8-azabicyclo[3.2.1]-octanylpyrimidinyl, 3-oxa-8-azabicyclo[3.2.1]octanylpyrimidinyl, oxo-3,6-diazabicyclo-[3.2.2]nonanylpyrimidinyl, carboxy-3-oxa-7-azabicyclo[3.3.1]nonanylpyrimidinyl, 3,7-dioxa-9-azabicyclo[3.3.1]nonanylpyrimidinyl, carboxy-5-azaspiro[2.3]hexanylpyrimidinyl, (carboxy)(methyl)-5-azaspiro[2.3]hexanylpyrimidinyl, carboxy-5-azaspiro-[2.4]heptanylpyrimidinyl, carboxy-2-azaspiro[3.3]heptanylpyrimidinyl, 2-oxa-6-azaspiro-[3.3]heptanylpyrimidinyl, 3-oxa-6-azaspiro[3.3]heptanylpyrimidinyl, dioxo-6-thia-2-azaspiro[3.3]heptanylpyrimidinyl, 2-oxa-6-azaspiro[3.4]octanylpyrimidinyl, 2-oxa-6-azaspiro[3.5]nonanylpyrimidinyl, 2-oxa-7-azaspiro[3.5]nonanylpyrimidinyl and (dioxo)(methyl)-2,4,8-triazaspiro[4.5]decanylpyrimidinyl.

Illustrative values of $R^{11}$ include methylsulphonylphenyl and hydroxyisopropylpyrimidinyl.

Typically, $R^{15}$ and $R^{16}$ may independently represent hydrogen, fluoro, chloro, bromo, cyano, nitro, methyl, isopropyl, trifluoromethyl, hydroxy, methoxy, difluoromethoxy, trifluoromethoxy, methylthio, methylsulfinyl, methylsulfonyl, amino, methylamino, tert-butylamino, dimethylamino, phenylamino, acetylamino, methylsulfonylamino, formyl, acetyl, cyclopropylcarbonyl, azetidinylcarbonyl, pyrrolidinylcarbonyl, piperidinylcarbonyl, piperazinylcarbonyl, morpholinylcarbonyl, carboxy, methoxycarbonyl, aminocarbonyl, methylaminocarbonyl, dimethylaminocarbonyl, aminosulfonyl, methylaminosulfonyl and dimethylaminosulfonyl.

Suitably, $R^{15}$ and $R^{16}$ may independently represent hydrogen, chloro, methyl, methoxy or difluoromethoxy.

Typical values of $R^{15}$ include hydrogen, halogen, $C_{1-6}$ alkyl, trifluoromethyl, $C_{1-6}$ alkoxy, difluoromethoxy and trifluoromethoxy.

Suitable values of $R^{15}$ include hydrogen, halogen, $C_{1-6}$ alkyl, $C_{1-6}$ alkoxy and difluoromethoxy.

In a first embodiment, $R^{15}$ represents hydrogen. In a second embodiment, $R^{15}$ represents halogen. In a first aspect of that embodiment, $R^{15}$ represents fluoro. In a second aspect of that embodiment, $R^{15}$ represents chloro. In a third embodiment, $R^{15}$ represents $C_{1-6}$ alkyl. In one aspect of that embodiment, $R^{15}$ represents methyl. In a fourth embodiment, $R^{15}$ represents trifluoromethyl. In a fifth embodiment, $R^{15}$ represents $C_{1-6}$ alkoxy. In one aspect of that embodiment, $R^{15}$ represents methoxy. In a sixth embodiment, $R^{15}$ represents difluoromethoxy. In a seventh embodiment, $R^{15}$ represents trifluoromethoxy.

Selected values of $R^{15}$ include hydrogen, fluoro, chloro, methyl, trifluoromethyl, methoxy, difluoromethoxy and trifluoromethoxy.

Illustrative values of $R^{15}$ include hydrogen, chloro, methyl, methoxy and difluoro-methoxy.

Typical values of $R^{16}$ include hydrogen, halogen, cyano, $C_{1-6}$ alkyl, trifluoro-methyl, difluoromethoxy and amino.

In a first embodiment, $R^{16}$ represents hydrogen. In a second embodiment, $R^{16}$ represents halogen. In a first aspect of that embodiment, $R^{16}$ represents fluoro. In a second aspect of that embodiment, $R^{16}$ represents chloro. In a third embodiment, $R^{16}$ represents cyano. In a fourth embodiment, $R^{16}$ represents $C_{1-6}$ alkyl. In one aspect of that embodiment, $R^{16}$ represents methyl. In a fifth embodiment, $R^{16}$ represents trifluoro-methyl. In a sixth embodiment, $R^{16}$ represents difluoromethoxy. In a seventh embodiment, $R^{16}$ represents amino.

Selected values of $R^{16}$ include hydrogen, fluoro, chloro, cyano, methyl, trifluoro-methyl, difluoromethoxy and amino.

In a particular embodiment, $R^{16}$ is attached at the para-position of the phenyl ring relative to the integer $R^{15}$.

A particular sub-group of the compounds of formula (IIA) above is represented by the compounds of formula (IIB) and N-oxides thereof, and pharmaceutically acceptable salts and solvates thereof, and glucuronide derivatives thereof, and co-crystals thereof:

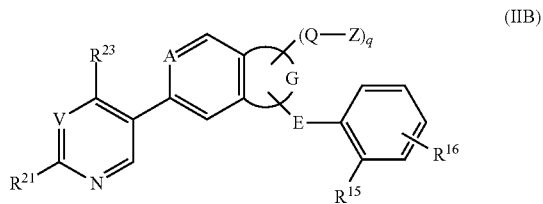

(IIB)

wherein

V represents C—$R^{22}$ or N;

$R^{21}$ represents hydrogen, halogen, halo($C_{1-6}$)alkyl, cyano, $C_{1-6}$ alkyl, trifluoro-methyl, $C_{2-6}$ alkenyl, $C_{2-6}$ alkynyl, hydroxy, hydroxy($C_{1-6}$)alkyl, $C_{1-6}$ alkoxy, ($C_{1-6}$)alkoxy-($C_{1-6}$)alkyl, difluoromethoxy, trifluoromethoxy, trifluoroethoxy, carboxy($C_{3-7}$)cycloalkyloxy, $C_{1-6}$ alkylthio, $C_{1-6}$ alkylsulphonyl, ($C_{1-6}$)alkylsulphonyl($C_{1-6}$)alkyl, amino, amino-($C_{1-6}$)alkyl, $C_{1-6}$ alkylamino, di($C_{1-6}$)alkylamino, ($C_{1-6}$) alkoxy($C_{1-6}$)alkylamino, N—[($C_{1-6}$)-alkyl]-N-[hydroxy ($C_{1-6}$)alkyl]amino, $C_{2-6}$ alkylcarbonylamino, ($C_{2-6}$)alkylcarbonylamino-($C_{1-6}$)alkyl, $C_{2-6}$ alkoxycarbonylamino, N—[($C_{1-6}$)alkyl]-N-[carboxy($C_1$-$C_6$)alkyl]amino, carboxy ($C_{3-7}$)cycloalkylamino, carboxy($C_{3-7}$)cycloalkyl($C_{1-6}$)alkylamino, $C_{1-6}$ alkylsulphonylamino, $C_{1-6}$ alkylsulphonylamino($C_{1-6}$)alkyl, formyl, $C_{2-6}$ alkylcarbonyl, ($C_{2-6}$) alkylcarbonyloxy($C_{1-6}$)alkyl, carboxy, carboxy($C_{1-6}$)alkyl, $C_{2-6}$ alkoxycarbonyl, morpholinyl($C_{1-6}$)alkoxycarbonyl, $C_{2-6}$ alkoxycarbonyl($C_{1-6}$)alkyl, $C_{2-6}$ alkoxycarbonylmethylidenyl, aminocarbonyl, $C_{1-6}$ alkylaminocarbonyl, di($C_{1-6}$) alkylaminocarbonyl, aminosulphonyl, $C_{1-6}$ alkylaminosulphonyl, di($C_{1-6}$)alkylaminosulphonyl, ($C_{1-6}$) alkylsulphoximinyl or [($C_{1-6}$)alkyl][N—($C_{1-6}$)alkyl] sulphoximinyl; or $R^{21}$ represents ($C_{3-7}$)cycloalkyl, ($C_{3-7}$) cycloalkyl($C_{1-6}$)alkyl, ($C_{4-7}$)cycloalkenyl, ($C_{4-9}$) bicycloalkyl, ($C_{3-7}$)heterocycloalkyl, ($C_{3-7}$) heterocycloalkenyl, ($C_{4-9}$)heterobicycloalkyl or ($C_{4-9}$) spiroheterocycloalkyl, any of which groups may be optionally substituted by one or more substituents;

$R^{22}$ represents hydrogen, halogen or $C_{1-6}$ alkyl;

$R^{23}$ represents hydrogen, $C_{1-6}$ alkyl, trifluoromethyl or $C_{1-6}$ alkoxy; and q, A, G, E, Q, Z, $R^{15}$ and $R^{16}$ are as defined above.

In one embodiment, V represents C—$R^{22}$. In another embodiment, V represents N.

Typically, $R^{21}$ represents hydrogen, halogen, halo($C_{1-6}$) alkyl, cyano, $C_{1-6}$ alkyl, trifluoromethyl, $C_{2-6}$ alkenyl, hydroxy, hydroxy($C_{1-6}$)alkyl, $C_{1-6}$ alkoxy, trifluoroethoxy, carboxy($C_{3-7}$)cycloalkyloxy, $C_{1-6}$ alkylthio, $C_{1-6}$ alkylsulphonyl, amino, $C_{1-6}$ alkylamino, di($C_{1-6}$)alkylamino, ($C_{1-6}$) alkoxy($C_{1-6}$)alkylamino, N—[($C_{1-6}$)alkyl]-N-[hydroxy ($C_{1-6}$)alkyl]-amino, N—[($C_{1-6}$)alkyl]-N-[carboxy($C_{1-6}$) alkyl]amino, carboxy($C_{3-7}$)cycloalkylamino, carboxy($C_{3-7}$) cycloalkyl($C_{1-6}$)alkylamino, $C_{1-6}$ alkylsulphonylamino, ($C_{2-6}$)alkylcarbonyl-oxy($C_{1-6}$)alkyl, carboxy, morpholinyl ($C_{1-6}$)alkoxycarbonyl, $C_{2-6}$ alkoxycarbonyl($C_{1-6}$)alkyl or $C_{2-6}$ alkoxycarbonylmethylidenyl; or $R^{21}$ represents ($C_{3-7}$) cycloalkyl, ($C_{3-7}$)cycloalkyl-($C_{1-6}$)alkyl, ($C_{4-7}$)cycloalkenyl, ($C_{4-9}$)bicycloalkyl, ($C_{3-7}$)heterocycloalkyl, ($C_{4-9}$)heterobicycloalkyl or ($C_{4-9}$)spiroheterocycloalkyl, any of which groups may be optionally substituted by one or more substituents.

Where $R^{21}$ represents an optionally substituted ($C_{3-7}$) cycloalkyl group, typical values include cyclopropyl, cyclobutyl, cyclopentyl, cyclohexyl and cycloheptyl, any of which groups may be optionally substituted by one or more substituents.

Where $R^{21}$ represents an optionally substituted ($C_{3-7}$) cycloalkyl($C_{1-6}$)alkyl group, a typical value is cyclohexylmethyl, which group may be optionally substituted by one or more substituents.

Where $R^{21}$ represents an optionally substituted ($C_{4-7}$) cycloalkenyl group, typical values include cyclobutenyl, cyclopentenyl, cyclohexenyl and cycloheptenyl, any of which groups may be optionally substituted by one or more substituents.

Where $R^{21}$ represents an optionally substituted ($C_{4-9}$) bicycloalkyl group, typical values include bicyclo[3.1.0] hexanyl, bicyclo[4.1.0]heptanyl and bicyclo[2.2.2]octanyl, any of which groups may be optionally substituted by one or more substituents.

Where $R^{21}$ represents an optionally substituted ($C_{3-7}$) heterocycloalkyl group, typical values include oxetanyl, azetidinyl, tetrahydrofuranyl, pyrrolidinyl, tetrahydropyranyl, piperidinyl, piperazinyl, hexahydro-[1,2,5]thiadiazolo [2,3-c]pyrazinyl, morpholinyl, thiomorpholinyl, azepanyl, oxazepanyl, diazepanyl and thiadiazepanyl, any of which groups may be optionally substituted by one or more substituents.

Where $R^{21}$ represents an optionally substituted ($C_{3-7}$) heterocycloalkenyl group, a typical value is optionally substituted 1,2,3,6-tetrahydropyridinyl.

Where $R^{21}$ represents an optionally substituted ($C_{4-9}$) heterobicycloalkyl group, typical values include 3-azabicyclo[3.1.0]hexanyl, 2-oxa-5-azabicyclo[2.2.1]heptanyl, 3-azabicyclo[3.1.1]heptanyl, 6-oxa-3-azabicyclo[3.1.1]heptanyl, 3-azabicyclo[4.1.0]-heptanyl, 2-oxabicyclo[2.2.2]octanyl, quinuclidinyl, 2-oxa-5-azabicyclo[2.2.2]octanyl, 3-azabicyclo[3.2.1]octanyl, 8-azabicyclo[3.2.1]octanyl, 3-oxa-8-azabicyclo[3.2.1]octanyl, 3,8-diazabicyclo[3.2.1] octanyl, 3,6-diazabicyclo[3.2.2]nonanyl, 3-oxa-7-azabicyclo-[3.3.1]nonanyl, 3,7-dioxa-9-azabicyclo[3.3.1]nonanyl and 3,9-diazabicyclo[4.2.1]nonanyl, any of which groups may be optionally substituted by one or more substituents.

Where $R^{21}$ represents an optionally substituted ($C_{4-9}$) spiroheterocycloalkyl group, typical values include 5-azaspiro[2.3]hexanyl, 5-azaspiro[2.4]heptanyl, 2-azaspiro [3.3]-heptanyl, 2-oxa-6-azaspiro[3.3]heptanyl, 3-oxa-6-azaspiro[3.3]heptanyl, 6-thia-2-azaspiro[3.3]heptanyl, 2-oxa-6-azaspiro[3.4]octanyl, 2-oxa-6-azaspiro[3.5] nonanyl, 2-oxa-7-azaspiro[3.5]nonanyl and 2,4,8-triazaspiro [4.5]decanyl, any of which groups may be optionally substituted by one or more substituents.

Illustratively, $R^{21}$ represents hydroxy, hydroxy($C_{1-6}$) alkyl, methoxy, carboxycyclobutyloxy, methylthio, methylsulphonyl, methylamino, N-[carboxyethyl]-N-methylamino, carboxycyclopentylamino, carboxycyclopropylmethylamino or ethoxycarbonylethyl; or $R^{21}$ represents cyclopropyl, cyclobutyl, cyclopentyl, cyclohexyl, cyclohexylmethyl, cyclohexenyl, bicyclo[3.1.0]hexanyl, bicyclo[4.1.0]heptanyl, bicyclo[2.2.2]-octanyl, oxetanyl, azetidinyl, tetrahydrofuranyl, pyrrolidinyl, tetrahydropyranyl, piperidinyl, piperazinyl, hexahydro-[1,2,5]thiadiazolo[2,3-a]pyrazinyl, morpholinyl, thiomorpholinyl, azepanyl, oxazepanyl, diazepanyl, thiadiazepanyl, 3-azabicyclo[3.1.0]-hexanyl, 2-oxa-5-azabicyclo[2.2.1]heptanyl, 3-azabicyclo[3.1.1]heptanyl, 6-oxa-3-azabicyclo[3.1.1]heptanyl, 3-azabicyclo[4.1.0]heptanyl, 2-oxabicyclo[2.2.2]octanyl, 3-azabicyclo[3.2.1]octanyl, 8-azabicyclo[3.2.1]octanyl, 3-oxa-8-azabicyclo[3.2.1]octanyl, 3,6-diazabicyclo[3.2.2]nonanyl, 3-oxa-7-azabicyclo[3.3.1]nonanyl, 3,7-dioxa-9-azabicyclo[3.3.1]nonanyl, 5-azaspiro[2.3]hexanyl, 5-azaspiro[2.4]heptanyl, 2-azaspiro-[3.3]heptanyl, 3-oxa-6-azaspiro[3.3]heptanyl or 6-thia-2-azaspiro[3.3]heptanyl, any of which groups may be optionally substituted by one or more substituents.

Examples of optional substituents which may be present on $R^{21}$ include one, two or three substituents independently selected from halogen, halo($C_{1-6}$)alkyl, cyano, cyano-($C_{1-6}$)alkyl, nitro, nitro($C_{1-6}$)alkyl, $C_{1-6}$ alkyl, trifluoromethyl, trifluoroethyl, $C_{2-6}$ alkenyl, hydroxy, hydroxy($C_{1-6}$)alkyl, $C_{1-6}$ alkoxy, difluoromethoxy, trifluoromethoxy, trifluoroethoxy, $C_{1-6}$ alkylthio, $C_{1-6}$ alkylsulphonyl, ($C_{1-6}$)alkylsulphonyl($C_{1-6}$)alkyl, oxo, amino, $C_{1-6}$ alkylamino, di($C_{1-6}$) alkylamino, $C_{2-6}$ alkylcarbonylamino, ($C_{2-6}$) alkylcarbonylamino-($C_{1-6}$)alkyl, $C_{2-6}$ alkoxycarbonylamino, $C_{1-6}$ alkylsulphonylamino, formyl, $C_{2-6}$ alkylcarbonyl, carboxy, carboxy($C_{1-6}$)alkyl, $C_{2-6}$ alkoxycarbonyl, morpholinyl-($C_{1-6}$)alkoxycarbonyl, $C_{2-6}$ alkoxycarbonyl($C_{1-6}$)alkyl, $C_{2-6}$ alkoxycarbonylmethylidenyl, a carboxylic acid isostere or prodrug moiety Ω as defined herein, —($C_{1-6}$)alkyl-Ω, aminocarbonyl, $C_{1-6}$ alkylaminocarbonyl, di($C_{1-6}$)alkylaminocarbonyl, aminosulphonyl, di($C_{1-6}$)alkylaminosulphonyl, ($C_{1-6}$)alkylsulphoximinyl and [($C_{1-6}$)alkyl][N—($C_{1-6}$)alkyl]-sulphoximinyl.

Suitable examples of particular substituents on $R^{21}$ include one, two or three substituents independently selected from fluoro, fluoromethyl, chloro, bromo, cyano, cyanomethyl, cyanoethyl, nitro, nitromethyl, methyl, ethyl, isopropyl, trifluoromethyl, trifluoroethyl, ethenyl, hydroxy, hydroxymethyl, methoxy, ethoxy, difluoromethoxy, trifluoromethoxy, trifluoroethoxy, methylthio, methylsulphonyl, methylsulphonylmethyl, methylsulphonylethyl, oxo, amino, methylamino, dimethylamino, acetylamino, acetylaminomethyl, methoxycarbonylamino, ethoxycarbonylamino, tert-butoxycarbonylamino, methylsulphonylamino, formyl, acetyl, carboxy, carboxymethyl, carboxyethyl, methoxycarbonyl, ethoxycarbonyl, n-butoxycarbonyl, tert-butoxycarbonyl, morpholinylethoxycarbonyl, methoxycarbonylmethyl, ethoxycarbonylmethyl, ethoxycarbonylethyl, ethoxycarbonylmethylidenyl, acetylaminosulphonyl, methoxyaminocarbonyl, tetrazolyl, tetrazolylmethyl, hydroxyoxadiazolyl, aminocarbonyl, methylaminocarbonyl, dimethylaminocarbonyl, methylsulphonylaminocarbonyl, aminosulphonyl, methylaminosulphonyl, dimethylaminosulphonyl, methylsulphoximinyl and (methyl)(N-methyl)sulphoximinyl.

Typically, $R^{21}$ represents hydrogen, fluoro, fluoroisopropyl, cyano, methyl, trifluoromethyl, ethenyl, hydroxy, hydroxyisopropyl, methoxy, isopropoxy, trifluoroethoxy, carboxycyclobutyloxy, methylthio, methylsulphonyl, amino, methylamino, dimethylamino, methoxyethylamino, N-(hydroxyethyl)-N-(methyl)amino, N-[carboxyethyl]-N-methylamino, carboxycyclopentylamino, carboxycyclopropylmethylamino, methylsulphonylamino, acetoxyisopropyl, carboxy, ethoxycarbonylethyl, fluoromethyl-cyclopropyl, hydroxycyclopropyl, (difluoro)(hydroxy)cyclopropyl, acetylaminomethyl-cyclopropyl, hydroxycyclobutyl, carboxycyclopentyl, carboxycyclohexyl, (carboxy)-(methyl)cyclohexyl, (carboxy)(hydroxy)cyclohexyl, carboxymethylcyclohexyl, ethoxycarbonylcyclohexyl, (methoxycarbonyl)(methyl)cyclohexyl, (ethoxycarbonyl)-(methyl)cyclohexyl, carboxycyclohexylmethyl, carboxycyclohexenyl, ethoxycarbonyl-cyclohexenyl, carboxybicyclo[3.1.0]hexanyl, ethoxycarbonylbicyclo[3.1.0]hexanyl, carboxybicyclo[4.1.0]heptanyl, carboxybicyclo[2.2.2]octanyl, fluorooxetanyl, hydroxyoxetanyl, difluoroazetidinyl, hydroxyazetidinyl, (hydroxy)(methyl)azetidinyl, (hydroxy)(trifluoromethyl)azetidinyl, carboxyazetidinyl, (tert-butoxycarbonyl)(hydroxy)-azetidinyl, tetrazolylazetidinyl, hydroxytetrahydrofuranyl, pyrrolidinyl, hydroxy-pyrrolidinyl, carboxypyrrolidinyl, (carboxy)(methyl)pyrrolidinyl, carboxymethyl-pyrrolidinyl, ethoxycarbonylpyrrolidinyl, fluorotetrahydropyranyl, hydroxytetrahydropyranyl, piperidinyl, difluoropiperidinyl, (cyano)(methyl)piperidinyl, (hydroxy)-(nitromethyl)piperidinyl, (hydroxy)(methyl)piperidinyl, (hydroxy)(trifluoromethyl)-piperidinyl, (hydroxymethyl)(methyl)piperidinyl, methylsulphonylpiperidinyl, oxopiperidinyl, (formyl)(methyl)piperidinyl, acetylpiperidinyl, carboxypiperidinyl, (carboxy)(fluoro)piperidinyl, (carboxy)(methyl)piperidinyl, (carboxy)(ethyl)piperidinyl, (carboxy)(trifluoromethyl)piperidinyl, (carboxy)(hydroxy)piperidinyl, (carboxy)-(hydroxymethyl)piperidinyl, (carboxy)(methoxy)piperidinyl, (amino)(carboxy)piperidinyl, carboxymethylpiperidinyl, methoxycarbonylpiperidinyl, (methoxycarbonyl)(methyl)-piperidinyl, (ethyl)(methoxycarbonyl)piperidinyl, (isopropyl)(methoxycarbonyl)-piperidinyl, (methoxy)(methoxycarbonyl)piperidinyl, (carboxy)(methoxycarbonyl)-piperidinyl, ethoxycarbonylpiperidinyl, (ethoxycarbonyl)(fluoro)piperidinyl, (ethoxycarbonyl)(methyl)piperidinyl, (ethoxycarbonyl)(trifluoromethyl)piperidinyl, (ethoxycarbonyl)(hydroxymethyl)piperidinyl, (n-butoxycarbonyl)(methyl)piperidinyl, (methyl)(morpholinylethoxycarbonyl)piperidinyl, ethoxycarbonylmethylpiperidinyl, methylsulphonylaminocarbonylpiperidinyl, acetylaminosulphonylpiperidinyl, methoxyaminocarbonylpiperidinyl, tetrazolylpiperidinyl, hydroxyoxadiazolylpiperidinyl, aminosulphonylpiperidinyl, piperazinyl, cyanoethylpiperazinyl, trifluoroethylpiperazinyl, methylsulphonylpiperazinyl, methylsulphonylethylpiperazinyl, oxopiperazinyl, acetylpiperazinyl, carboxypiperazinyl, tert-butoxycarbonylpiperazinyl, carboxymethyl-piperazinyl, carboxyethylpiperazinyl, ethoxycarbonylmethylpiperazinyl, ethoxycarbonylethylpiperazinyl, tetrazolylmethylpiperazinyl, trioxohexahydro-[1,2,5]thiadiazolo[2,3-a]-pyrazinyl, morpholinyl, dimethylmorpholinyl, hydroxymethylmorpholinyl, carboxy-morpholinyl, (carboxy)(methyl)morpholinyl, carboxymethylmorpholinyl, thiomorpholinyl, oxothiomorpholinyl, dioxothiomorpholinyl, carboxyazepanyl, carboxyoxazepanyl, oxodiazepanyl, (methyl)(oxo)diazepanyl, dioxothiadiazepanyl, carboxy-3-azabicyclo-[3.1.0]hexanyl, (carboxy)(methyl)-3-azabicyclo[3.1.0]hexanyl, methoxycarbonyl-3-azabicyclo[3.1.0]hexanyl, ethoxycarbonyl-3-azabicyclo[3.1.0]hexanyl, 2-oxa-5-azabicyclo[2.2.1]heptanyl, carboxy-2-oxa-5-azabicyclo[2.2.1]heptanyl, carboxy-3-azabicyclo[3.1.1]heptanyl, 6-oxa-3-azabicyclo[3.1.1]heptanyl, carboxy-3-azabicyclo-[4.1.0]heptanyl, methoxycarbonyl-3-azabicyclo[4.1.0]heptanyl, ethoxycarbonyl-3-azabicyclo[4.1.0]heptanyl, (hydroxy)(methyl)(oxo)-2-oxabicyclo[2.2.2]octanyl, carboxy-3-azabicyclo[3.2.1]octanyl, methoxycarbonyl-3-azabicyclo[3.2.1]octanyl, oxo-8-azabicyclo[3.2.1]octanyl, ethoxycarbonylmethylidenyl-8-azabicyclo[3.2.1]octanyl, 3-oxa-8-azabicyclo[3.2.1]octanyl, oxo-3,6-diazabicyclo[3.2.2]nonanyl, carboxy-3-oxa-7-azabicyclo[3.3.1]nonanyl, 3,7-dioxa-9-azabicyclo[3.3.1]nonanyl, carboxy-5-azaspiro-[2.3]hexanyl, (carboxy)(methyl)-5-azaspiro[2.3]hexanyl, carboxy-5-azaspiro[2.4]heptanyl, carboxy-2-azaspiro[3.3] heptanyl, 2-oxa-6-azaspiro[3.3]heptanyl, 3-oxa-6-azaspiro[3.3]-heptanyl, dioxo-6-thia-2-azaspiro[3.3]heptanyl, 2-oxa-6-azaspiro[3.4]octanyl, 2-oxa-6-azaspiro[3.5]nonanyl, 2-oxa-7-azaspiro[3.5]nonanyl or (dioxo)(methyl)-2,4,8-tri-azaspiro-[4.5]decanyl.

In a particular embodiment, $R^{21}$ represents hydroxy $(C_{1-6})$alkyl. In one aspect of that embodiment, $R^{21}$ represents hydroxyisopropyl, especially 2-hydroxyprop-2-yl.

Generally, $R^{22}$ represents hydrogen or $C_{1-6}$ alkyl.

Suitably, $R^{22}$ represents hydrogen, chloro or methyl.

Typically, $R^{22}$ represents hydrogen or methyl.

In one embodiment, $R^{22}$ represents hydrogen. In another embodiment, $R^{22}$ represents $C_{1-6}$ alkyl, especially methyl. In a further embodiment, $R^{22}$ represents halogen. In one aspect of that embodiment, $R^{22}$ represents fluoro. In another aspect of that embodiment, $R^{22}$ represents chloro.

Generally, $R^{23}$ represents hydrogen or $C_{1-6}$ alkyl.

Suitably, $R^{23}$ represents hydrogen, methyl, trifluoromethyl or methoxy.

Typically, $R^{23}$ represents hydrogen or methyl.

In one embodiment, $R^{23}$ represents hydrogen. In another embodiment, $R^{23}$ represents $C_{1-6}$ alkyl, especially methyl. In a further embodiment, $R^{23}$ represents trifluoromethyl. In an additional embodiment, $R^{23}$ represents $C_{1-6}$ alkoxy, especially methoxy.

Particular sub-groups of the compounds of formula (IIB) above are represented by the compounds of formula (IIC), (IID), (IIE), (IIF), (IIG), (IIH), (IIJ), (IIK) and (IIL), and N-oxides thereof, and pharmaceutically acceptable salts and solvates thereof, and glucuronide derivatives thereof, and co-crystals thereof:

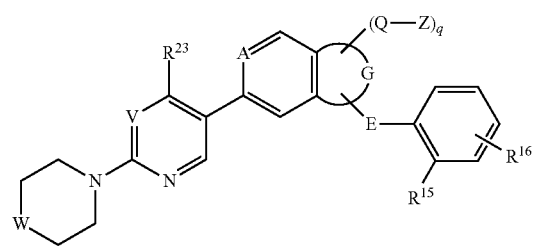
(IIC)

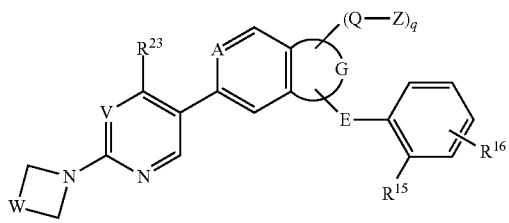
(IID)

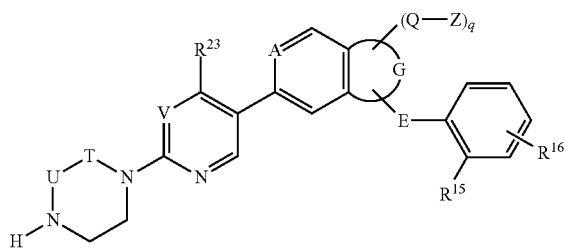
(IIE)

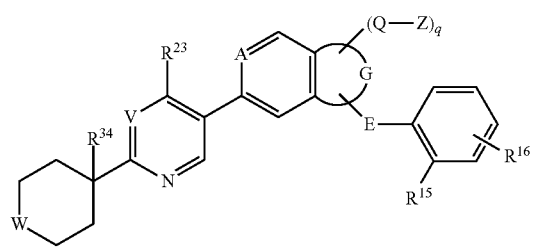
(IIF)

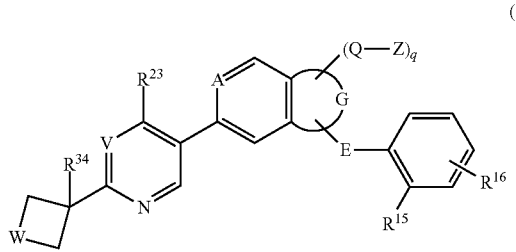
(IIG)

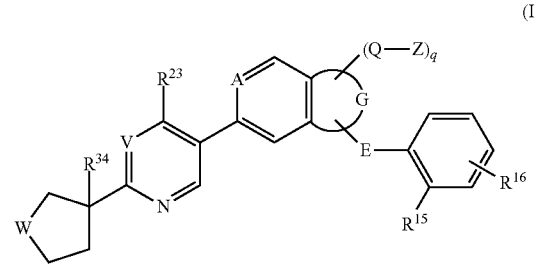
(IIH)

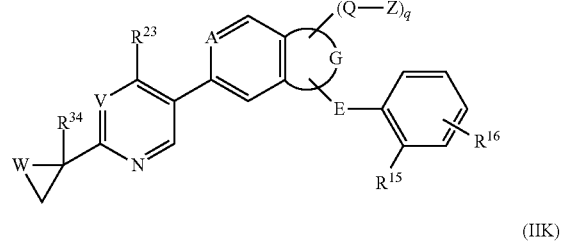
(IIJ)

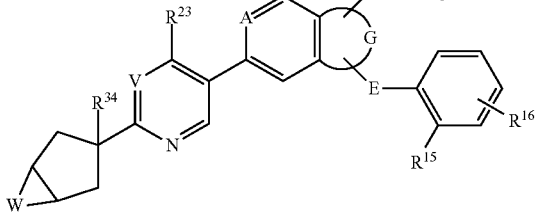
(IIK)

-continued

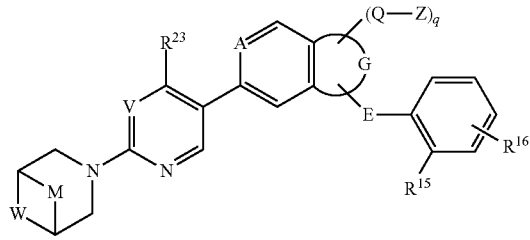

(IIL)

wherein
T represents —CH$_2$— or —CH$_2$CH$_2$—;
U represents C(O) or S(O)$_2$;
W represents O, S, S(O), S(O)$_2$, S(O)(NR$^6$), N(R$^{31}$) or C(R$^{32}$)(R$^{33}$);
-M- represents —CH$_2$— or —CH$_2$CH$_2$—;
R$^{31}$ represents hydrogen, cyano(C$_{1-6}$)alkyl, C$_{1-6}$ alkyl, trifluoromethyl, trifluoroethyl, C$_{1-6}$ alkylsulphonyl, (C$_{1-6}$)alkylsulphonyl(C$_{1-6}$)alkyl, formyl, C$_{2-6}$ alkylcarbonyl, carboxy, carboxy(C$_{1-6}$)alkyl, C$_{2-6}$ alkoxycarbonyl, C$_{2-6}$ alkoxycarbonyl(C$_{1-6}$)alkyl, a carboxylic acid isostere or prodrug moiety Ω, —(C$_{1-6}$)alkyl-Ω, aminocarbonyl, C$_{1-6}$ alkylaminocarbonyl, di(C$_{1-6}$)alkylaminocarbonyl, aminosulphonyl or di(C$_{1-6}$)alkylaminosulphonyl;
R$^{32}$ represents hydrogen, halogen, cyano, hydroxy, hydroxy(C$_{1-6}$)alkyl, C$_{1-6}$ alkylsulphonyl, formyl, C$_{2-6}$ alkylcarbonyl, carboxy, carboxy(C$_{1-6}$)alkyl, C$_{2-6}$ alkoxycarbonyl, C$_{2-6}$ alkoxycarbonyl(C$_{1-6}$)alkyl, aminosulphonyl, (C$_{1-6}$)alkylsulphoximinyl, [(C$_{1-6}$)alkyl][N—(C$_{1-6}$)alkyl]sulphoximinyl, a carboxylic acid isostere or prodrug moiety Ω, or —(C$_{1-6}$)alkyl-Ω;
R$^{33}$ represents hydrogen, halogen, C$_{1-6}$ alkyl, trifluoromethyl, hydroxy, hydroxy-(C$_{1-6}$)alkyl, C$_{1-6}$ alkoxy, amino or carboxy;
R$^{34}$ represents hydrogen, halogen, halo(C$_{1-6}$)alkyl, hydroxy, C$_{1-6}$ alkoxy, C$_{1-6}$ alkylthio, C$_{1-6}$ alkylsulphinyl, C$_{1-6}$ alkylsulphonyl, amino, C$_{1-6}$ alkylamino, di(C$_{1-6}$)alkylamino, (C$_{2-6}$)alkylcarbonylamino, (C$_{2-6}$)alkylcarbonylamino(C$_{1-6}$)alkyl, (C$_{1-6}$)alkylsulphonylamino or (C$_{1-6}$)alkylsulphonylamino(C$_{1-6}$)alkyl; and
q, A, G, E, Q, Z, R$^6$, V, R$^{15}$, R$^{16}$, R$^{23}$ and Ω are as defined above.

In a first embodiment, T represents —CH$_2$—. In a second embodiment, T represents —CH$_2$CH$_2$—.

In a first embodiment, U represents C(O). In a second embodiment, U represents S(O)$_2$.

Generally, W represents O, S(O)$_2$, N(R$^{31}$) or C(R$^{32}$)(R$^{33}$). Typically, W represents O, N(R$^{31}$) or C(R$^{32}$)(R$^{33}$).

In a first embodiment, W represents O. In a second embodiment, W represents S. In a third embodiment, W represents S(O). In a fourth embodiment, W represents S(O)$_2$. In a fifth embodiment, W represents S(O)(NR$^6$). In a sixth embodiment, W represents N(R$^{31}$). In a seventh embodiment, W represents C(R$^{32}$)(R$^{33}$).

In one embodiment, -M- represents —CH$_2$—. In another embodiment, -M- represents —CH$_2$CH$_2$—.

Typically, R$^{31}$ represents hydrogen, cyano(C$_{1-6}$)alkyl, C$_{1-6}$ alkyl, trifluoromethyl, trifluoroethyl, C$_{1-6}$ alkylsulphonyl, (C$_{1-6}$)alkylsulphonyl(C$_{1-6}$)alkyl, formyl, C$_{2-6}$ alkylcarbonyl, carboxy, carboxy(C$_{1-6}$)alkyl, C$_{2-6}$ alkoxycarbonyl, C$_{2-6}$ alkoxycarbonyl-(C$_{1-6}$)alkyl, tetrazolyl(C$_{1-6}$)alkyl, aminocarbonyl, C$_{1-6}$ alkylaminocarbonyl, aminocarbonyl, aminosulphonyl, C$_{1-6}$ alkylaminosulphonyl or di(C$_{1-6}$)alkylaminosulphonyl.

Typical values of R$^{31}$ include hydrogen, cyanoethyl, methyl, ethyl, isopropyl, trifluoromethyl, trifluoroethyl, methylsulphonyl, methylsulphonylethyl, formyl, acetyl, carboxy, carboxymethyl, carboxyethyl, methoxycarbonyl, ethoxycarbonyl, tert-butoxycarbonyl, ethoxycarbonylmethyl, ethoxycarbonylethyl, tetrazolylmethyl, aminocarbonyl, methylamino-carbonyl, dimethylaminocarbonyl, aminosulphonyl, methylaminosulphonyl and dimethylaminosulphonyl.

A particular value of R$^{31}$ is hydrogen.

Generally, R$^{32}$ represents hydrogen, halogen, hydroxy, carboxy, carboxy(C$_{1-6}$)-alkyl, C$_{2-6}$ alkoxycarbonyl, C$_{2-6}$ alkoxycarbonyl(C$_{1-6}$)alkyl, a carboxylic acid isostere or prodrug moiety Ω, or —(C$_{1-6}$)alkyl-Ω.

Typically, R$^{32}$ represents hydrogen, halogen, cyano, hydroxy, hydroxy(C$_{1-6}$)alkyl, C$_{1-6}$ alkylsulphonyl, formyl, carboxy, carboxy(C$_{1-6}$)alkyl, C$_{2-6}$ alkoxycarbonyl, C$_{2-6}$ alkoxycarbonyl(C$_{1-6}$)alkyl, aminosulphonyl, (C$_{1-6}$)alkylsulphoximinyl, [(C$_1$-C$_6$)alkyl][N—(C$_{1-6}$)alkyl]sulphoximinyl, (C$_{1-6}$)alkylsulphonylaminocarbonyl, (C$_{2-6}$)alkylcarbonylaminosulphonyl, (C$_{1-6}$)alkoxyaminocarbonyl, tetrazolyl or hydroxyoxadiazolyl.

Typical values of R$^{32}$ include hydrogen, fluoro, cyano, hydroxy, hydroxymethyl, methylsulphonyl, formyl, carboxy, carboxymethyl, carboxyethyl, methoxycarbonyl, ethoxycarbonyl, tert-butoxycarbonyl, methoxycarbonylmethyl, methoxycarbonylethyl, ethoxycarbonylmethyl, ethoxycarbonylethyl, aminosulphonyl, methylsulphoximinyl, (methyl)(N-methyl)sulphoximinyl, methylsulphonylaminocarbonyl, acetylaminosulphonyl, methoxyaminocarbonyl, tetrazolyl and hydroxyoxadiazolyl.

In a selected embodiment, R$^{32}$ represents carboxy.

Generally, R$^{33}$ represents hydrogen, halogen, C$_{1-6}$ alkyl or trifluoromethyl.

Selected values of R$^{33}$ include hydrogen, fluoro, methyl, ethyl, isopropyl, trifluoromethyl, hydroxy, hydroxymethyl, methoxy, amino and carboxy.

Particular values of R$^{33}$ include hydrogen, fluoro, methyl and trifluoromethyl.

In a first embodiment, R$^{33}$ represents hydrogen. In a second embodiment, R$^{33}$ represents halogen. In one aspect of that embodiment, R$^{33}$ represents fluoro. In a third embodiment, R$^{33}$ represents C$_{1-6}$ alkyl. In a first aspect of that embodiment, R$^{33}$ represents methyl. In a second aspect of that embodiment, R$^{33}$ represents ethyl. In a third aspect of that embodiment, R$^{33}$ represents isopropyl. In a fourth embodiment, R$^{33}$ represents trifluoromethyl. In a fifth embodiment, R$^{33}$ represents hydroxy. In a sixth embodiment, R$^{33}$ represents hydroxy(C$_{1-6}$)alkyl. In one aspect of that embodiment, R$^{33}$ represents hydroxymethyl. In a seventh embodiment, R$^{33}$ represents C$_{1-6}$ alkoxy. In one aspect of that embodiment, R$^{33}$ represents methoxy. In an eighth embodiment, R$^{33}$ represents amino. In a ninth embodiment, R$^{33}$ represents carboxy.

In a first embodiment, R$^{34}$ represents hydrogen. In a second embodiment, R$^{34}$ represents halogen. In one aspect of that embodiment, R$^{34}$ represents fluoro. In a third embodiment, R$^{34}$ represents halo(C$_{1-6}$)alkyl. In one aspect of that embodiment, R$^{34}$ represents fluoromethyl. In a fourth embodiment, R$^{34}$ represents hydroxy. In a fifth embodiment, R$^{34}$ represents C$_{1-6}$ alkoxy, especially methoxy. In a sixth embodiment, R$^{34}$ represents C$_{1-6}$ alkylthio, especially methylthio. In a seventh embodiment, R$^{34}$ represents C$_{1-6}$ alkylsulphinyl, especially methylsulphinyl. In an eighth embodiment, R$^{34}$ represents C$_{1-6}$ alkylsulphonyl, especially methylsulphonyl. In a ninth embodiment, R$^{34}$ represents amino. In a tenth embodiment, R$^{34}$ represents C$_{1-6}$ alkylamino, especially methylamino. In an eleventh embodiment, $R^{34}$ represents di($C_{1-6}$)alkylamino, especially dimethylamino. In a twelfth embodiment, $R^{34}$ represents ($C_{2-6}$) alkylcarbonylamino, especially acetylamino. In a thirteenth embodiment, $R^{34}$ represents ($C_{2-6}$)alkylcarbonylamino ($C_{1-6}$)alkyl, especially acetylaminomethyl. In a fourteenth embodiment, $R^{34}$ represents ($C_{1-6}$)alkylsulphonylamino, especially methylsulphonylamino. In a fifteenth embodiment, $R^{34}$ represents ($C_{1-6}$)alkylsulphonylamino($C_{1-6}$)alkyl, especially methylsulphonylaminomethyl.

Typically, $R^{34}$ represents hydrogen, halogen, halo($C_{1-6}$) alkyl, hydroxy or ($C_{2-6}$)alkylcarbonylamino($C_{1-6}$)alkyl.

Suitably, $R^{34}$ represents hydrogen, halogen or hydroxy.

Selected values of $R^{34}$ include hydrogen, fluoro, fluoromethyl, hydroxy, methoxy, methylthio, methylsulphinyl, methylsulphonyl, amino, methylamino, dimethylamino and acetylaminomethyl.

Particular values of $R^{34}$ include hydrogen, fluoro, fluoromethyl, hydroxy and acetylaminomethyl.

Suitably, $R^{34}$ represents hydrogen, fluoro or hydroxy.

An alternative sub-class of compounds of formula (IIA) above is represented by the compounds of formula (IIM) and N-oxides thereof, and pharmaceutically acceptable salts and solvates thereof, and glucuronide derivatives thereof, and co-crystals thereof:

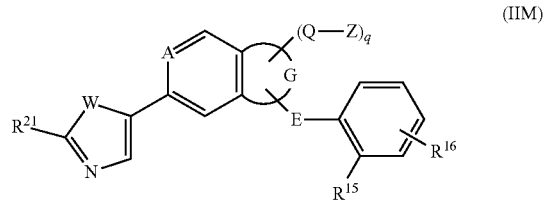

(IIM)

wherein q, A, G, E, Q, Z, W, $R^{15}$, $R^{16}$ and $R^{21}$ are as defined above.

With specific reference to formula (IIM), the integer W is suitably O, S or N—$R^{31}$, especially S or N—$R^{31}$.

Specific novel compounds in accordance with the present invention include each of the compounds whose preparation is described in the accompanying Examples, and pharmaceutically acceptable salts and solvates thereof, and co-crystals thereof.

The compounds in accordance with the present invention are beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

Inflammatory and autoimmune disorders include systemic autoimmune disorders, autoimmune endocrine disorders and organ-specific autoimmune disorders. Systemic autoimmune disorders include systemic lupus erythematosus (SLE), psoriasis, psoriatic arthropathy, vasculitis, polymyositis, scleroderma, multiple sclerosis, systemic sclerosis, ankylosing spondylitis, rheumatoid arthritis, non-specific inflammatory arthritis, juvenile inflammatory arthritis, juvenile idiopathic arthritis (including oligoarticular and polyarticular forms thereof), anaemia of chronic disease (ACD), Still's disease (juvenile and/or adult onset), Behçet's disease and Sjögren's syndrome. Autoimmune endocrine disorders include thyroiditis. Organ-specific autoimmune disorders include Addison's disease, haemolytic or pernicious anaemia, acute kidney injury (AKI; including cisplatin-induced AKI), diabetic nephropathy (DN), obstructive uropathy (including cisplatin-induced obstructive uropathy), glomerulonephritis (including Goodpasture's syndrome, immune complex-mediated glomerulonephritis and antineutrophil cytoplasmic antibodies (ANCA)-associated glomerulonephritis), lupus nephritis (LN), minimal change disease, Graves' disease, idiopathic thrombocytopenic purpura, inflammatory bowel disease (including Crohn's disease, ulcerative colitis, indeterminate colitis and pouchitis), pemphigus, atopic dermatitis, autoimmune hepatitis, primary biliary cirrhosis, autoimmune pneumonitis, autoimmune carditis, myasthenia gravis, spontaneous infertility, osteoporosis, osteopenia, erosive bone disease, chondritis, cartilage degeneration and/or destruction, fibrosing disorders (including various forms of hepatic and pulmonary fibrosis), asthma, rhinitis, chronic obstructive pulmonary disease (COPD), respiratory distress syndrome, sepsis, fever, muscular dystrophy (including Duchenne muscular dystrophy) and organ transplant rejection (including kidney allograft rejection).

Neurological and neurodegenerative disorders include Alzheimer's disease, Parkinson's disease, Huntington's disease, ischaemia, stroke, amyotrophic lateral sclerosis, spinal cord injury, head trauma, seizures and epilepsy.

Cardiovascular disorders include thrombosis, cardiac hypertrophy, hypertension, irregular contractility of the heart (e.g. during heart failure), and sexual disorders (including erectile dysfunction and female sexual dysfunction). Modulators of TNFα function may also be of use in the treatment and/or prevention of myocardial infarction (see J. J. Wu et al., *JAMA*, 2013, 309, 2043-2044).

Metabolic disorders include diabetes (including insulin-dependent diabetes mellitus and juvenile diabetes), dyslipidemia and metabolic syndrome.

Ocular disorders include retinopathy (including diabetic retinopathy, proliferative retinopathy, non-proliferative retinopathy and retinopathy of prematurity), macular oedema (including diabetic macular oedema), age-related macular degeneration (ARMD), vascularisation (including corneal vascularisation and neovascularisation), retinal vein occlusion, and various forms of uveitis and keratitis.

Oncological disorders, which may be acute or chronic, include proliferative disorders, especially cancer, and cancer-associated complications (including skeletal complications, cachexia and anaemia). Particular categories of cancer include haematological malignancy (including leukaemia and lymphoma) and non-haematological malignancy (including solid tumour cancer, sarcoma, meningioma, glioblastoma multiforme, neuroblastoma, melanoma, gastric carcinoma and renal cell carcinoma). Chronic leukaemia may be myeloid or lymphoid. Varieties of leukaemia include lymphoblastic T cell leukaemia, chronic myelogenous leukaemia (CML), chronic lymphocytic/lymphoid leukaemia (CLL), hairy-cell leukaemia, acute lymphoblastic leukaemia (ALL), acute myelogenous leukaemia (AML), myelodysplastic syndrome, chronic neutrophilic leukaemia, acute lymphoblastic T cell leukaemia, plasmacytoma, immunoblastic large cell leukaemia, mantle cell leukaemia, multiple myeloma, acute megakaryoblastic leukaemia, acute megakaryocytic leukaemia, promyelocytic leukaemia and erythroleukaemia. Varieties of lymphoma include malignant lymphoma, Hodgkin's lymphoma, non-Hodgkin's lymphoma, lymphoblastic T cell lymphoma, Burkitt's lymphoma, follicular lymphoma, MALT1 lymphoma and marginal zone lymphoma. Varieties of non-haematological malignancy include cancer of the prostate, lung, breast, rectum, colon, lymph node, bladder, kidney, pancreas, liver, ovary, uterus, cervix, brain, skin, bone, stomach and muscle. Modulators of TNFα function may also be used to increase the safety of the potent anticancer effect of TNF (see F. V. Hauwermeiren et al., *J. Clin. Invest.*, 2013, 123, 2590-2603).

The present invention also provides a pharmaceutical composition which comprises a compound in accordance with the invention as described above, or a pharmaceutically acceptable salt or solvate thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds of use in the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds of use in the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds of use in the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds of use in the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of use in the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

If desired, a compound in accordance with the present invention may be co-administered with another pharmaceutically active agent, e.g. an anti-inflammatory molecule such as methotrexate or prednisolone.

The compounds of formula (IB-A) above may be prepared by a process which comprises reacting a compound of formula Y-E-M$^1$ with a compound of formula (III):

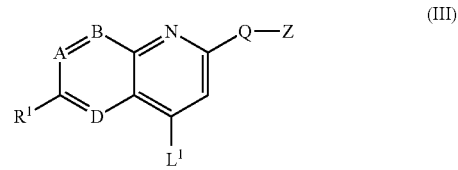

(III)

wherein A, B, D, E, Q, Y, Z and R$^1$ are as defined above, L$^1$ represents a suitable leaving group, and M$^1$ represents a boronic acid moiety —B(OH)$_2$ or a cyclic ester thereof formed with an organic diol, e.g. pinacol, 1,3-propanediol or neopentyl glycol, or M$^1$ represents —ZnHal in which Hal represents a halogen atom, e.g. chloro; in the presence of a transition metal catalyst.

The leaving group $L^1$ is typically a halogen atom, e.g. chloro or bromo; or an organic sulfonate derivative, e.g. trifluoromethylsulfonate.

The transition metal catalyst of use in the reaction between Y-E-$M^1$ and compound (III) is suitably [1,1'-bis(diphenylphosphino)ferrocene]dichloropalladium(II), dichloro-[1,1'-bis(di-tert-butylphosphino)ferrocene]palladium(II), tetrakis(triphenylphosphine)-palladium(0), or bis [3-(diphenylphosphanyl)cyclopenta-2,4-dien-1-yl]iron-dichloropalladium-dichloromethane complex. The reaction is suitably performed in the presence of a base, e.g. an inorganic base such as sodium carbonate or potassium carbonate, or potassium phosphate. The reaction is conveniently carried out at an elevated temperature in a suitable solvent, e.g a cyclic ether such as 1,4-dioxane or tetrahydrofuran.

Alternatively, the compounds of formula (IB-A) above may be prepared by a variant of the Skraup reaction which comprises reacting a compound of formula (IV) with a compound of formula (V):

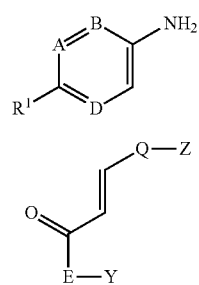

(IV)

(V)

wherein A, B, D, E, Q, Y, Z and $R^1$ are as defined above; in the presence of a suitable oxidant (cf. *Organic Reactions*, 1953, 7, 59).

The compounds of formula (IB-B) above may be prepared by a process which comprises reacting a compound of formula Y-E-$M^1$ with a compound of formula (VI):

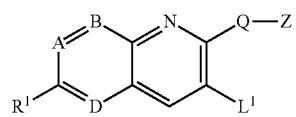

(VI)

wherein A, B, D, E, Q, Y, Z, $R^1$, $L^1$ and $M^1$ are as defined above; in the presence of a transition metal catalyst; under conditions analogous to those described above for the reaction between Y-E-$M^1$ and compound (III).

Alternatively, the compounds of formula (IB-B) may be prepared by a method analogous to that described by C. S. Cho & J. U. Kim, *Tetrahedron Lett.*, 2007, 48, 3775; or by S. C. Kim, *Bull. Korean Chem. Soc.*, 2005, 26, 1001.

The compounds of formula (IB-B) wherein E represents C(O) may be prepared by a method analogous to that described by Y. T. Reddy, *Synth. Commun.*, 2008, 38, 3201.

The compounds of formula (IB-B) wherein -Q-Z represents $-NH_2$ may be prepared by a method analogous to that described in WO 2007/022946.

The compounds of formula (IB-C) above may be prepared by a process which comprises reacting a compound of formula Y-E-$M^1$ with a compound of formula (VII):

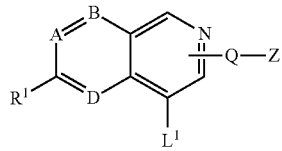

(VII)

wherein A, B, D, E, Q, Y, Z, $R^1$, $L^1$ and $M^1$ are as defined above; in the presence of a transition metal catalyst; under conditions analogous to those described above for the reaction between Y-E-$M^1$ and compound (III).

The intermediates of formula (VII) wherein $L^1$ is bromo may be prepared by treating a compound of formula (VIII):

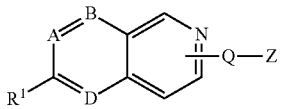

(VIII)

wherein A, B, D, Q, Z and $R^1$ are as defined above; with a brominating agent, e.g. N-bromosuccinimide.

The intermediates of formula (VIII) may be prepared by a method analogous to that described in WO 2012/148808.

Alternatively, the compounds of formula (IB-C) above may be prepared by a method analogous to that described by D. E. Minter & M. A. Re, *J. Org. Chem.*, 1988, 53, 2653.

The compounds of formula (IB-D) above may be prepared by a process which comprises reacting a compound of formula Y-E-$M^1$ with a compound of formula (IX):

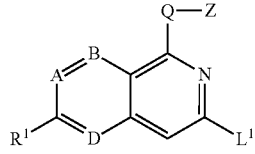

(IX)

wherein A, B, D, E, Q, Y, Z, $R^1$, $L^1$ and $M^1$ are as defined above; in the presence of a transition metal catalyst; under conditions analogous to those described above for the reaction between Y-E-$M^1$ and compound (III).

Alternatively, the compounds of formula (IB-D) wherein E represents —O— or —S— may be prepared by a process which comprises reacting a compound of formula (IX) above with a compound of formula Y—OH or Y—SH respectively, typically in the presence of a base.

The intermediates of formula (IX) may be prepared by a method analogous to that described in WO 2013/003315.

The compounds of formula (IB-E) above may be prepared by a process which comprises reacting a compound of formula Y-E-$M^1$ with a compound of formula (X):

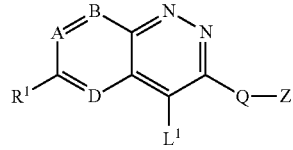

(X)

wherein A, B, D, E, Q, Y, Z, R¹, L¹ and M¹ are as defined above; in the presence of a transition metal catalyst; under conditions analogous to those described above for the reaction between Y-E-M¹ and compound (III).

Where L¹ represents trifluoromethylsulfonate, the intermediates of formula (X) above may be prepared by reacting a compound of formula (XI):

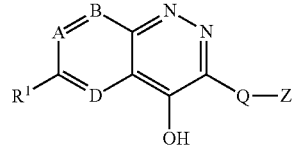
(XI)

wherein A, B, D, Q, Z and R¹ are as defined above; with a triflating agent, e.g. Comins reagent.

The intermediates of formula (XI) may be prepared by a method analogous to that described in U.S. Pat. No. 4,620,000; or in DD 258809.

The compounds of formula (IB-F) above may be prepared by a process which comprises reacting a compound of formula Y-E-M¹ with a compound of formula (XII):

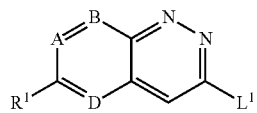
(XII)

wherein A, B, D, E, Y, R¹, L¹ and M¹ are as defined above; in the presence of a transition metal catalyst; under conditions analogous to those described above for the reaction between Y-E-M¹ and compound (III).

Alternatively, the compounds of formula (IB-F) wherein E represents —O— or —S— may be prepared by a process which comprises reacting a compound of formula (XII) above with a compound of formula Y—OH or Y—SH respectively, typically in the presence of a base.

The intermediates of formula (XII) may be prepared by a method analogous to that described by N. Le Fur et al., *Tetrahedron*, 2004, 60, 7983.

Alternatively, the compounds of formula (IB-F) wherein E represents C(O) may be prepared by a method analogous to that described by N. A. Al-Awadi, *Tetrahedron*, 2001, 57, 1609.

The compounds of formula (IB-G) above may be prepared by a process which comprises reacting a compound of formula Y-E-M¹ with a compound of formula (XIII):

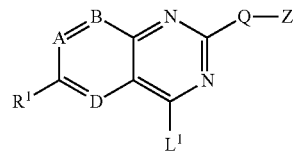
(XIII)

wherein A, B, D, E, Q, Y, Z, R¹, L¹ and M¹ are as defined above; in the presence of a transition metal catalyst; under conditions analogous to those described above for the reaction between Y-E-M¹ and compound (III).

The intermediates of formula (XIII) wherein L¹ is chloro may be prepared by treating a compound of formula (XIV):

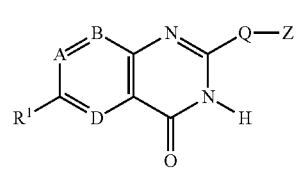
(XIV)

wherein A, B, D, Q, Z and R¹ are as defined above; with phosphorus oxychloride.

The intermediates of formula (XIV) may be prepared by reacting a compound of formula Z-Q-CO₂H with a compound of formula (XV):

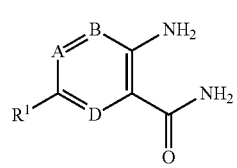
(XV)

wherein A, B, D, Q, Z and R¹ are as defined above.

The compounds of formula (IB-H) above may be prepared by a process which comprises reacting a compound of formula (XVI) with a compound of formula (XVII):

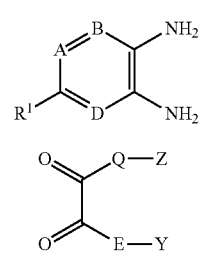
(XVI)

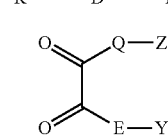
(XVII)

wherein A, B, D, E, Q, Y, Z and R¹ are as defined above; under conditions analogous to those described by D. Van Leusen & A. M. Van Leusen, *Tetrahedron Lett.*, 1977, 48, 4233.

The intermediates of formula (XVII) above may be prepared by a method analogous to that described by J. Ji & K-I. Lee, *J. Korean Chem. Soc.*, 2005, 49, 150.

Alternatively, the compounds of formula (IB-H) above may be prepared by a method analogous to that described in US-A-2005/0176717; or a method analogous to that described by A. Kaschers et al., *Tetrahedron*, 1992, 49, 381.

The compounds of formula (IB-H) above may be prepared by a process which comprises reacting a compound of formula Y-E-M¹ with a compound of formula (XVIII):

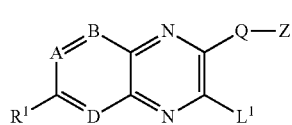
(XVIII)

wherein A, B, D, E, Q, Y, Z, $R^1$, $L^1$ and $M^1$ are as defined above; in the presence of a transition metal catalyst; under conditions analogous to those described above for the reaction between Y-E-$M^1$ and compound (III).

The compounds of formula (IB-H) wherein E represents —O— may be prepared by a process which comprises reacting a compound of formula Y—OH with a compound of formula (XVIII) as defined above. The reaction is suitably performed in the presence of a base, e.g. an inorganic base such as potassium carbonate. The reaction is conveniently carried out at an elevated temperature in a suitable solvent, e.g a dialkylsulfoxide derivative such as dimethylsulfoxide.

The compounds of formula (IB-J) above may be prepared by a process which comprises reacting a compound of formula Y-E-$M^1$ with a compound of formula (XIX):

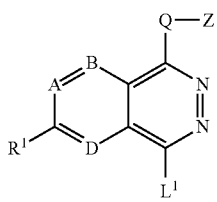
(XIX)

wherein A, B, D, E, Q, Y, Z, $R^1$, $L^1$ and $M^1$ are as defined above; in the presence of a transition metal catalyst; under conditions analogous to those described above for the reaction between Y-E-$M^1$ and compound (III).

The intermediates of formula (XIX) wherein $L^1$ is chloro may be prepared by treating a compound of formula (XX):

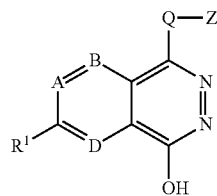
(XX)

wherein A, B, D, Q, Z and $R^1$ are as defined above; with phosphorus oxychloride.

The intermediates of formula (XX) may be prepared by reacting hydrazine with a compound of formula (XXI):

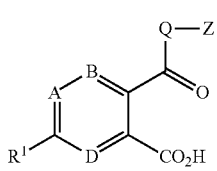
(XXI)

wherein A, B, D, Q, Z and $R^1$ are as defined above.

The compounds of formula (IB-K) above may be prepared by a process which comprises reacting a compound of formula Y-E-$M^1$ with a compound of formula (XXII):

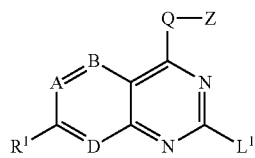
(XXII)

wherein A, B, D, E, Q, Y, Z, $R^1$, $L^1$ and $M^1$ are as defined above; in the presence of a transition metal catalyst; under conditions analogous to those described above for the reaction between Y-E-$M^1$ and compound (III).

The intermediates of formula (XXII) wherein $L^1$ is chloro may be prepared by treating a compound of formula (XXIII):

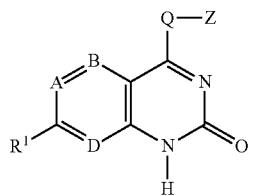
(XXIII)

wherein A, B, D, Q, Z and $R^1$ are as defined above; with phosphorus oxychloride.

The intermediates of formula (XXIII) wherein -Q-Z represents —$NH_2$ may be prepared by reacting urea with a compound of formula (XXIV):

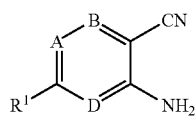
(XXIV)

wherein A, B, D and $R^1$ are as defined above; under conditions analogous to those described by J. A. Seijas et al., *Tetrahedron Lett.*, 2000, 41, 2215.

Alternatively, the compounds of formula (IB-K) above may be prepared by a method analogous to that described by J. Bergman et al., *Tetrahedron*, 1986, 42, 3697.

The compounds of formula (IB-L) above may be prepared by a method analogous to that described by R. Cerri, *J. Heterocycl. Chem*, 1979, 16, 1005; or by B. Pal, *Magyar Kemiai Folyoirat*, 1976, 82, 166.

Alternatively, the compounds of formula (IB-L) above may be prepared by a method analogous to that described by S. Y. Kang, *Bull. Korean Chem. Soc.*, 2011, 32, 2938, commencing from an appropriately substituted fused 1,3,4-benzotriazine-4-oxide (prepared as described by K. Pchalek & M. P. Hay, *J. Org. Chem.*, 2006, 71, 6530).

Where they are not commercially available, the starting materials of formula (III), (IV), (V), (VI), (XV), (XVI), (XVIII), (XXI) and (XXIV) may be prepared by standard methods well known from the art.

It will be understood that any compound of formula (I) initially obtained from any of the above processes may, where appropriate, subsequently be elaborated into a further compound of formula (I) by techniques known from the art. By way of example, a compound wherein E represents —C(O)— may be converted into the corresponding compound wherein E represents —CH(OH)— by treatment with a reducing agent such as sodium borohydride.

A compound wherein E represents —CH(OH)— may be converted into the corresponding compound wherein E represents —CH$_2$— by heating with elemental iodine and phosphinic acid in acetic acid; or by treating with triethylsilane and an acid, e.g. an organic acid such as trifluoroacetic acid, or a Lewis acid such as boron trifluoride diethyl etherate; or by treating with chlorotrimethylsilane and sodium iodide; or by a two-step procedure which comprises: (i) treatment with thionyl bromide; and (ii) treatment of the product thereby obtained with a transition metal catalyst, e.g. (2,2'-bipyridine)dichloro-ruthenium(II) hydrate, in the presence of diethyl 1,4-dihydro-2,6-dimethyl-3,5-pyridine-dicarboxylate (Hantzsch ester) and a base, e.g. an organic base such as N,N-diisopropylethylamine.

A compound wherein E represents —CH$_2$— may be converted into the corresponding compound wherein E represents —CH(CH$_3$)— by treatment with a methyl halide, e.g. methyl iodide, in the presence of a base such as lithium hexamethyldisilazide.

A compound which contains a hydroxy group may be alkylated by treatment with the appropriate alkyl halide in the presence of a base, e.g. sodium hydride, or silver oxide. A compound which contains hydroxy may be converted into the corresponding fluoro-substituted compound by treatment with diethylaminosulfur trifluoride (DAST) or bis(2-methoxyethyl)aminosulfur trifluoride (BAST). A compound which contains hydroxy may be converted into the corresponding difluoro-substituted compound via a two-step procedure which comprises: (i) treatment with an oxidising agent, e.g. manganese dioxide; and (ii) treatment of the carbonyl-containing compound thereby obtained with DAST.

A compound which contains an N—H moiety may be alkylated by treatment with the appropriate alkyl halide, typically at an elevated temperature in an organic solvent such as acetonitrile; or at ambient temperature in the presence of a base, e.g. an alkali metal carbonate such as potassium carbonate or cesium carbonate, in a suitable solvent, e.g. a dipolar aprotic solvent such as N,N-dimethylformamide. Alternatively, a compound which contains an N—H moiety may be alkylated by treatment with the appropriate alkyl tosylate in the presence of a base, e.g. an inorganic base such as sodium hydride, or an organic base such as 1,8-diazabicyclo[5.4.0]undec-7-ene (DBU).

A compound which contains an N—H moiety may be methylated by treatment with formaldehyde in the presence of a reducing agent, e.g. sodium triacetoxyborohydride.

A compound which contains an N—H moiety may be acylated by treatment with the appropriate acid chloride, e.g. acetyl chloride, or with the appropriate carboxylic acid anhydride, e.g. acetic anhydride, typically at ambient temperature in the presence of a base, e.g. an organic base such as triethylamine.

A compound which contains an N—H moiety may be converted into the corresponding compound wherein the nitrogen atom is substituted by $C_{1-6}$ alkylsulphonyl, e.g. methylsulphonyl, by treatment with the appropriate $C_{1-6}$ alkylsulphonyl chloride, e.g. methanesulphonyl chloride, or with the appropriate $C_{1-6}$ alkylsulphonic acid anhydride, e.g. methanesulphonic anhydride, typically at ambient temperature in the presence of a base, e.g. an organic base such as triethylamine or N,N-diisopropylethylamine.

A compound substituted by amino (—NH$_2$) may be converted into the corresponding compound substituted by $C_{1-6}$ alkylsulphonylamino, e.g. methylsulphonylamino, or bis[($C_{1-6}$)alkylsulphonyl]amino, e.g. bis(methylsulphonyl) amino, by treatment with the appropriate $C_{1-6}$ alkylsulphonyl halide, e.g. a $C_{1-6}$ alkylsulphonyl chloride such as methanesulphonyl chloride. Similarly, a compound substituted by hydroxy (—OH) may be converted into the corresponding compound substituted by $C_{1-6}$ alkylsulphonyloxy, e.g. methylsulphonyloxy, by treatment with the appropriate $C_{1-6}$ alkylsulphonyl halide, e.g. a $C_{1-6}$ alkylsulphonyl chloride such as methanesulphonyl chloride.

A compound containing the moiety —S— may be converted into the corresponding compound containing the moiety —S(O)— by treatment with 3-chloroperoxybenzoic acid. Likewise, a compound containing the moiety —S(O)— may be converted into the corresponding compound containing the moiety —S(O)$_2$— by treatment with 3-chloroperoxybenzoic acid. Alternatively, a compound containing the moiety —S— may be converted into the corresponding compound containing the moiety —S(O)$_2$— by treatment with Oxone® (potassium peroxymonosulfate).

A compound containing an aromatic nitrogen atom may be converted into the corresponding N-oxide derivative by treatment with 3-chloroperoxybenzoic acid.

A bromophenyl derivative may be converted into the corresponding optionally substituted 2-oxopyrrolidin-1-yl-phenyl or 2-oxooxazolidin-3-ylphenyl derivative by treatment with pyrrolidin-2-one or oxazolidin-2-one, or an appropriately substituted analogue thereof. The reaction is conveniently effected at an elevated temperature in the presence of copper(I) iodide, trans-N,N'-dimethylcyclohexane-1,2-diamine and an inorganic base such as potassium carbonate.

A compound wherein $R^1$ represents halogen, e.g. chloro, bromo or iodo, may be converted into the corresponding compound wherein $R^1$ represents an optionally substituted aryl or heteroaryl moiety by treatment with the appropriately substituted aryl or heteroaryl boronic acid or a cyclic ester thereof formed with an organic diol, e.g. pinacol, 1,3-propanediol or neopentyl glycol. The reaction is typically effected in the presence of a transition metal catalyst, e.g. [1,1'-bis(diphenylphosphino)ferrocene]dichloropalladium (II), tetrakis(triphenylphosphine)palladium(0), or bis[3-(diphenylphosphanyl)cyclopenta-2,4-dien-1-yl]iron-dichloro-palladium-dichloromethane complex, or dichlorobis (triphenyl-phosphine)palladium(II), and a base, e.g. an inorganic base such as sodium carbonate or potassium carbonate, or potassium phosphate.

A compound wherein $R^1$ represents halogen, e.g. bromo, may be converted into the corresponding compound wherein $R^1$ represents an optionally substituted aryl, heteroaryl or heterocycloalkenyl moiety via a two-step procedure which comprises: (i) reaction with bis(pinacolato)diboron or bis (neopentyl glycolato)diboron; and (ii) reaction of the compound thereby obtained with an appropriately functionalised halo- or tosyloxy-substituted aryl, heteroaryl or heterocycloalkenyl derivative. Step (i) is conveniently effected in the presence of a transition metal catalyst such as [1,1'-bis (diphenylphosphino)-ferrocene]dichloropalladium(II), or bis[3-(diphenylphosphanyl)cyclopenta-2,4-dien-1-yl]iron-dichloropalladium-dichloromethane complex. Step (ii) is conveniently effected in the presence of a transition metal catalyst such as tetrakis(triphenylphosphine)-palladium(0), or bis[3-(diphenylphosphanyl)cyclopenta-2,4-dien-1-yl] iron-dichloropalladium-dichloromethane complex, and a base, e.g. an inorganic base such as sodium carbonate or potassium carbonate.

A compound wherein $R^1$ represents halogen, e.g. bromo, may be converted into the corresponding compound wherein R¹ represents an optionally substituted $C_{2-6}$ alkynyl moiety by treatment with an appropriately substituted alkyne derivative, e.g. 2-hydroxybut-3-yne. The reaction is conveniently accomplished with the assistance of a transition metal catalyst, e.g. tetrakis(triphenylphosphine)palladium (0), typically in the presence of copper(I) iodide and a base, e.g. an organic base such as triethylamine.

A compound wherein R¹ represents halogen, e.g. bromo, may be converted into the corresponding compound wherein R¹ represents an optionally substituted imidazol-1-yl moiety by treatment with the appropriately substituted imidazole derivative, typically in the presence of copper(II) acetate and an organic base such as N,N,N',N'-tetramethyl-ethylenediamine (TMEDA).

A compound wherein R¹ represents halogen, e.g. bromo, may be converted into the corresponding compound wherein R¹ represents 2-(methoxycarbonyl)ethyl via a two-step procedure which comprises: (i) reaction with methyl acrylate; and (ii) catalytic hydrogenation of the alkenyl derivative thereby obtained, typically by treatment with a hydrogenation catalyst, e.g. palladium on charcoal, under an atmosphere of hydrogen gas. Step (i) is typically effected in the presence of a transition metal catalyst, e.g. palladium(II) acetate or bis(dibenzylideneacetone)palladium(0), and a reagent such as tri(ortho-tolyl)-phosphine.

In general, a compound containing a —C≡C— functionality may be converted into the corresponding compound containing a —CH—CH— functionality by catalytic hydrogenation, typically by treatment with a hydrogenation catalyst, e.g. palladium on charcoal, under an atmosphere of hydrogen gas, optionally in the presence of a base, e.g. an alkali metal hydroxide such as sodium hydroxide, or an organic base such as triethylamine.

A compound wherein R¹ represents 6-methoxypyridin-3-yl may be converted into the corresponding compound wherein R¹ represents 2-oxo-1,2-dihydropyridin-5-yl by treatment with pyridine hydrochloride; or by heating with a mineral acid such as hydrochloric acid. By utilising similar methodology, a compound wherein R¹ represents 6-methoxy-4-methylpyridin-3-yl may be converted into the corresponding compound wherein R¹ represents 4-methyl-2-oxo-1,2-dihydropyridin-5-yl; and a compound wherein R¹ represents 6-methoxy-5-methylpyridin-3-yl may be converted into the corresponding compound wherein R¹ represents 3-methyl-2-oxo-1,2-dihydropyridin-5-yl.

A compound wherein R¹ represents 2-oxo-1,2-dihydropyridin-5-yl may be converted into the corresponding compound wherein R¹ represents 2-oxopiperidin-5-yl by catalytic hydrogenation, typically by treatment with gaseous hydrogen in the presence of a hydrogenation catalyst such as platinum(IV) oxide.

A compound containing an ester moiety, e.g. a $C_{2-6}$ alkoxycarbonyl group such as methoxycarbonyl or ethoxycarbonyl, may be converted into the corresponding compound containing a carboxy (—CO$_2$H) moiety by treatment with an acid, e.g. a mineral acid such as hydrochloric acid.

A compound containing an N-(tert-butoxycarbonyl) moiety may be converted into the corresponding compound containing an N—H moiety by treatment with an acid, e.g. a mineral acid such as hydrochloric acid, or an organic acid such as trifluoroacetic acid.

A compound containing an ester moiety, e.g. a $C_{2-6}$ alkoxycarbonyl group such as methoxycarbonyl or ethoxycarbonyl, may alternatively be converted into the corresponding compound containing a carboxy (—CO$_2$H) moiety by treatment with a base, e.g. an alkali metal hydroxide selected from lithium hydroxide, sodium hydroxide and potassium hydroxide; or an organic base such as sodium methoxide or sodium ethoxide.

A compound containing a carboxy (—CO$_2$H) moiety may be converted into the corresponding compound containing an amide moiety by treatment with the appropriate amine in the presence of a condensing agent such as 1-ethyl-3-(3-dimethylaminopropyl)-carbodiimide, or a coupling agent such as 1-[bis(dimethylamino)methylene]-1H-1,2,3-triazolo[4,5-b]pyridinium 3-oxid hexafluorophosphate (HATU).

A compound containing a carbonyl (C=O) moiety may be converted into the corresponding compound containing a —C(CH$_3$)(OH)— moiety by treatment with methylmagnesium bromide. Similarly, a compound containing a carbonyl (C=O) moiety may be converted into the corresponding compound containing a —C(CF$_3$)(OH)— moiety by treatment with (trifluoromethyl)trimethylsilane and cesium fluoride. A compound containing a carbonyl (C=O) moiety may be converted into the corresponding compound containing a —C(CH$_2$NO$_2$)(OH)— moiety by treatment with nitromethane.

A compound containing a hydroxymethyl moiety may be converted into the corresponding compound containing a formyl (—CHO) moiety by treatment with an oxidising agent such as Dess-Martin periodinane. A compound containing a hydroxymethyl moiety may be converted into the corresponding compound containing a carboxy moiety by treatment with an oxidising agent such as tetrapropylammonium perruthenate. Similarly, a compound containing a —CH(OH)— moiety may be converted into the corresponding compound containing a —C(O)— moiety by treatment with an oxidising agent such as tetrapropylammonium perruthenate.

A compound wherein R¹ represents a substituent containing at least one nitrogen atom, which substituent is linked to the remainder of the molecule via a nitrogen atom, may be prepared by reacting a compound wherein R¹ represents halogen, e.g. bromo, with the appropriate compound of formula R¹—H [e.g. 1-(pyridin-3-yl)piperazine or morpholine]. The reaction is conveniently effected with the assistance of a transition metal catalyst, e.g. tris(dibenzylideneacetone)dipalladium(0), in the presence of an amination ligand such as 2-dicyclohexylphosphino-2',4',6'-triisopropylbiphenyl (XPhos) or 2,2'-bis(diphenylphosphino)-1,1'-binaphthalene (BINAP) and a base, e.g. an inorganic base such as sodium tert-butoxide. Alternatively, the reaction may be effected using palladium diacetate, in the presence of a reagent such as [2',6'-bis(propan-2-yloxy)-biphenyl-2-yl](dicyclohexyl)phosphane and a base, e.g. an inorganic base such as cesium carbonate.

A compound containing an oxo moiety can be converted into the corresponding compound containing an ethoxycarbonylmethylidene moiety by treatment with triethyl phosphonoacetate in the presence of a base such as sodium hydride.

A compound wherein R²¹ represents ethenyl may be prepared by reacting a compound wherein R²¹ represents halogen, e.g. chloro, with potassium vinyl trifluoro-borate. The reaction is typically effected in the presence of a transition metal catalyst, e.g. [1,1'-bis(diphenylphosphino)ferrocene]dichloropalladium(II), and a base, e.g. an organic base such as triethylamine.

A compound wherein R²¹ represents halogen, e.g. chloro, may be converted into the corresponding compound wherein R²¹ represents an optionally substituted $C_{4-7}$ cycloalkenyl moiety by treatment with the appropriately substituted cycloalkenyl boronic acid or a cyclic ester thereof formed with an organic diol, e.g. pinacol, 1,3-propanediol or neopentyl glycol. The reaction is typically effected in the presence of a transition metal catalyst, e.g. bis[3-(diphenylphosphanyl)cyclopenta-2,4-dien-1-yl]iron-dichloropalladium-dichloromethane complex, and a base, e.g. an inorganic base such as potassium carbonate.

A compound wherein $R^{21}$ represents a substituent containing at least one nitrogen atom, which substituent is linked to the remainder of the molecule via a nitrogen atom, may be prepared by reacting a compound wherein $R^{21}$ represents halogen, e.g. chloro, with the appropriate compound of formula $R^{21}$—H [e.g. 2-methoxyethylamine, N-methyl-L-alanine, 2-aminocyclopentanecarboxylic acid, 3-aminocyclopentanecarboxylic acid, 1-(aminomethyl)cyclopropanecarboxylic acid, methyl azetidine-3-carboxylate, pyrrolidin-3-ol, pyrrolidine-3-carboxylic acid, piperidine-2-carboxylic acid, piperidine-3-carboxylic acid, 4-(1H-tetrazol-5-yl)piperidine, piperazine, 1-(methylsulfonyl)piperazine, piperazin-2-one, 2-(piperazin-1-yl)propanoic acid, morpholine, morpholine-2-carboxylic acid, thiomorpholine, thiomorpholine 1,1-dioxide, 1,4-diazepan-5-one, 2-oxa-5-azabicyclo-[2.2.1]heptane or an appropriately substituted azaspiroalkane], optionally in the presence of a base, e.g. an organic base such as triethylamine or N,N-diisopropylethylamine and/or 1-methyl-2-pyrrolidinone, or pyridine, or an inorganic base such as potassium carbonate.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I), this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode.

Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3$^{rd}$ edition, 1999. The protecting groups may be removed at any convenient subsequent stage utilising methods known from the art.

The following Examples illustrate the preparation of compounds according to the invention.

The compounds in accordance with this invention potently inhibit the binding of a fluorescence conjugate to TNFα when tested in the fluorescence polarisation assay described below. Moreover, certain compounds in accordance with this invention potently inhibit TNFα-induced NF-κB activation in the reporter gene assay described below.

Fluorescence Polarisation Assay
Preparation of Compound (A)
1-(2,5-Dimethylbenzyl)-6-[4-(piperazin-1-ylmethyl)phenyl]-2-(pyridin-4-ylmethyl)-1H-benzimidazole—hereinafter referred to as "Compound (A)"—can be prepared by the procedure described in Example 499 of WO 2013/186229; or by a procedure analogous thereto.

Preparation of Fluorescence Conjugate
Compound (A)
(27.02 mg, 0.0538 mmol) was dissolved in DMSO (2 mL). 5(-6) Carboxy-fluorescein succinimyl ester (24.16 mg, 0.0510 mmol) (Invitrogen catalogue number: C1311) was dissolved in DMSO (1 mL) to give a bright yellow solution. The two solutions were mixed at room temperature, the mixture turning red in colour. The mixture was stirred at room temperature. Shortly after mixing a 20 μL aliquot was removed and diluted in a 80:20 mixture of AcOH:$H_2O$ for LC-MS analysis on the 1200RR-6140 LC-MS system. The chromatogram showed two closely eluting peaks at retention times of 1.42 and 1.50 minutes, both with mass $(M+H)^+$= 860.8 amu, corresponding to the two products formed with the 5- and 6-substituted carboxyfluorescein group. A further peak at retention time 2.21 minutes had a mass of $(M+H)^+$= 502.8 amu, corresponding to Compound (A). No peak was observed for unreacted 5(-6) carboxyfluorescein succinimyl ester. The peak areas were 22.0%, 39.6% and 31.4% for the three signals, indicating a 61.6% conversion to the two isomers of the desired fluorescence conjugate at that time-point. Further 20 μL aliquots were extracted after several hours and then after overnight stirring, diluted as before and subjected to LC-MS analysis. The percentage conversion was determined as 79.8% and 88.6% respectively at these time-points. The mixture was purified on a UV-directed preparative HPLC system. The pooled purified fractions were freeze-dried to remove excess solvent. After freeze-drying, an orange solid (23.3 mg) was recovered, equivalent to 0.027 mmol of fluorescence conjugate, corresponding to an overall yield of 53% for the reaction and preparative HPLC purification.

Inhibition of Binding of Fluorescence Conjugate to TNFα
Compounds were tested at 10 concentrations starting from 25 μM in a final assay concentration of 5% DMSO, by pre-incubation with TNFα for 60 minutes at ambient temperature in 20 mM Tris, 150 mM NaCl, 0.05% Tween 20, before addition of the fluorescence conjugate and a further incubation for 20 hours at ambient temperature. The final concentrations of TNFα and the fluorescence conjugate were 10 nM and 10 nM respectively in a total assay volume of 25 pt. Plates were read on a plate reader capable of detecting fluorescence polarisation (e.g. an Analyst HT plate reader; or an Envision plate reader). An $IC_{50}$ value was calculated using XLfit™ (4 parameter logistic model) in ActivityBase.

When tested in the fluorescence polarisation assay, the compounds of the accompanying Examples were all found to exhibit $IC_{50}$ values of 50 µM or better.

Reporter Gene Assay

Inhibition of TNFα-Induced NF-κB Activation

Stimulation of HEK-293 cells by TNFα leads to activation of the NF-κB pathway. The reporter cell line used to determine TNFα activity was purchased from InvivoGen. HEK-Blue™ CD40L is a stable HEK-293 transfected cell line expressing SEAP (secreted embryonic alkaline phosphatase) under the control of the IFNβ minimal promoter fused to five NF-κB binding sites. Secretion of SEAP by these cells is stimulated in a dose-dependent manner by TNFα, with an EC50 of 0.5 ng/mL for human TNFα. Compounds were diluted from 10 mM DMSO stocks (final assay concentration 0.3% DMSO) to generate a 10-point 3-fold serial dilution curve (e.g. 30,000 nM to 2 nM final concentration). Diluted compound was preincubated with TNFα for 60 minutes prior to addition to a 384-well microtitre plate and incubated for 18 h. The final TNFα concentration in the assay plate was 0.5 ng/mL. SEAP activity was determined in the supernatant using a colorimetric substrate, e.g. QUANTI-Blue™ or HEK-Blue® Detection media (InvivoGen). Percentage inhibitions for compound dilutions were calculated between a DMSO control and maximum inhibition (by excess control compound) and an $IC_{50}$ value calculated using XLfit™ (4 parameter logistic model) in ActivityBase.

When tested in the reporter gene assay, certain compounds of the accompanying Examples were found to exhibit $IC_{50}$ values of 50 µM or better.

EXAMPLES

Abbreviations

DCM: dichloromethane EtOAc: ethyl acetate
MeOH: methanol DMSO: dimethylsulfoxide
DMF: N,N-dimethylformamide THF: tetrahydrofuran
Pd(dppf)Cl$_2$: [1,1'-bis(diphenylphosphino)ferrocene]dichloropalladium(II)
Barluenga's Reagent: bis(pyridine)iodonium(I) tetrafluoroborate
h: hour M: mass
r.t. room temperature RT: retention time
HPLC: High Performance Liquid Chromatography
LCMS: Liquid Chromatography Mass Spectrometry
ES+: Electrospray Positive Ionisation Nomenclature Compounds were named with the aid of ACD/Name Batch (Network) version 12.0 and/or Accelrys Draw 4.0.

Analytical Conditions

All reactions involving air- or moisture-sensitive reagents were performed under a nitrogen atmosphere using dried solvents and glassware.

LCMS data were determined by using Method 1 below.
Method 1
Column: Waters Acquity-SQD, Waters Acquity UPLC, BEH C18, 2.1×50 mm, 1.7 µm
Mobile phase A: 10 mM ammonium formate+0.1% ammonia
Mobile phase B: 95% acetonitrile+5% water+0.1% ammonia Gradient program (flow rate 1.0 mL/minute, column temperature 40° C.):

| Time | A % | B % |
| --- | --- | --- |
| 0.00 | 95.0 | 5.0 |
| 0.50 | 95.0 | 5.0 |
| 1.75 | 5.0 | 95.0 |
| 2.00 | 5.0 | 95.0 |
| 2.25 | 95.0 | 5.0 |

Intermediate 1

1-(2-Aminophenyl)propan-1-one

To a cooled (0° C.) solution of 2-aminobenzonitrile (5 g, 42.3 mmol) in THF (20 mL) was added dropwise ethylmagnesium chloride (2M in THF, 52.9 mL, 105.8 mmol) over 30 minutes via an addition funnel. The reaction mixture was allowed to warm to r.t. and stirred for 6 h. The reaction mixture was cooled to 0° C. and quenched by careful addition of 2M aqueous hydrochloric acid solution (ca. 60 mL). After 10 minutes, the mixture was basified at 0° C. by the slow addition of 2M aqueous sodium hydroxide solution (ca. 60 mL). The mixture was extracted with EtOAc (3×100 mL). The combined organic layers were dried (Na$_2$SO$_4$) and concentrated in vacuo. The residue was purified by flash column chromatography (SiO$_2$, 0-25% EtOAc/heptane), yielding the title compound (2.91 g, 46%) as a yellow oil which crystallised upon standing. $δ_H$ (250 MHz, CDCl$_3$) 7.77 (dd, J 8.5, 1.5 Hz, 1H), 7.42-7.12 (m, 1H), 6.71-6.62 (m, 2H), 6.28 (br s, 2H), 3.00 (q, J 7.5 Hz, 2H), 1.23 (t, J 7.5 Hz, 3H). LCMS (ES$^+$) 151.0 (M+H)$^+$, RT 1.12 minutes.

Intermediate 2

N-(2-Propanoylphenyl)acetamide

To a solution of Intermediate 1 (2.91 g, 19.5 mmol) in DCM (80 mL) was added triethylamine (2.99 mL, 21.5 mmol), followed by acetyl chloride (1.66 mL, 23.4 mmol). The reaction mixture was stirred at r.t. for 3 h, then washed with water (100 mL). The aqueous layer was back-extracted with DCM (2×50 mL). The combined organic layers were dried (Na$_2$SO$_4$) and concentrated in vacuo, yielding the title compound (3.72 g, 99%) as a pale yellow solid, which was used without further purification. $δ_H$ (500 MHz, CDCl$_3$) 11.75 (s, 1H), 8.74 (dd, J 8.5, 1.0 Hz, 1H), 7.93 (dd, J 8.0, 1.5 Hz, 1H), 7.58-7.51 (m, 1H), 7.15-7.08 (m, 1H), 3.08 (q, J 7.0 Hz, 2H), 2.24 (s, 3H), 1.23 (t, J 7.0 Hz, 3H). LCMS (ES$^+$) 192.0 (M+H)$^+$, RT 1.11 minutes.

Intermediate 3

N-(4-Bromo-2-propanoylphenyl)acetamide

To a solution of Intermediate 2 (3.72 g, 19.5 mmol) in acetic acid (40 mL) was added bromine (1.61 mL, 31.3 mmol) dropwise. The reaction mixture was stirred at r.t. for 1.5 h, then poured into water (80 mL). The resultant precipitate was collected by filtration, washed with water (50 mL) and heptane (50 mL), then dried in a vacuum oven at 40° C. for 18 h, yielding the title compound (4.82 g, 84%) as a pale yellow solid, which was used without further purification. $δ_H$ (500 MHz, CDCl$_3$) 11.63 (s, 1H), 8.68 (d, J 9.0 Hz, 1H), 8.02 (d, J 2.5 Hz, 1H), 7.63 (dd, J 9.0, 2.5 Hz, 1H), 3.05 (q, J 7.0 Hz, 2H), 2.24 (s, 3H), 1.23 (t, J 7.0 Hz, 3H). LCMS (ES$^+$) 270.0/272.0 (M+H)$^+$, RT 1.26 minutes.

Intermediate 4

6-Bromo-3-methyl-1H-cinnolin-4-one

To a solution of Intermediate 3 (4.82 g, 16.3 mmol) in THF (55 mL) were added conc. HCl (12 mL) and water (12 mL) and the resultant slurry was heated at 75° C. for 1.5 h. The reaction mixture was cooled to r.t. and the organic solvent was removed in vacuo. The resultant aqueous suspension was diluted with water (4 mL) and conc. HCl (4 mL), then cooled to −5° C. A solution of sodium nitrite (1.36 g, 19.5 mmol) in water (8 mL) was added in five portions, maintaining a reaction temperature below 0° C. The reaction mixture was warmed slowly to r.t. over 2 h, then stirred at r.t. for 18 h. After this time, the reaction mixture was heated at reflux for 6 h, then cooled to r.t. and filtered. The resultant solid was washed with water (2×20 mL) and diethyl ether (30 mL), then dried in a vacuum oven at 40° C. for 18 h, yielding the title compound (3.23 g, 83%) as a beige solid, which was used without further purification. $\delta_H$ (500 MHz, CDCl$_3$) 13.35 (s, 1H), 8.13 (d, J 2.0 Hz, 1H), 7.88 (dd, J 9.0, 2.0 Hz, 1H), 7.54 (d, J 9.0 Hz, 1H), 2.27 (s, 3H). LCMS (ES$^+$) 239.0/241.0 (M+H)$^+$, RT 0.99 minutes.

Intermediate 5

3-Methyl-6-[4-(methylsulfonyl)phenyl]-1H-cinnolin-4-one

A mixture of Intermediate 4 (500 mg, 1.97 mmol) and 4-(methylsulfonyl)phenyl-boronic acid (433 mg, 2.16 mmol) in 1,4-dioxane (30 mL) and 2M aqueous potassium carbonate solution (2.95 mL, 5.90 mmol) was degassed for 10 minutes under a stream of nitrogen prior to the addition of Pd(dppf)Cl$_2$.DCM (161 mg, 0.2 mmol). The reaction mixture was heated at 100° C. for 1 h. The reaction mixture was cooled to r.t, then partitioned between water (100 mL) and EtOAc (100 mL). The resultant precipitate between the layers was collected by filtration and dried in a vacuum oven at 40° C. for 18 h, yielding the title compound (484 mg, 78%) as a grey solid. $\delta_H$ (500 MHz, DMSO-d$_6$) 8.36 (d, J 2.0 Hz, 1H), 8.13 (dd, J 9.0, 2.0 Hz, 1H), 8.04 (s, 4H), 7.71 (d, J 9.0 Hz, 1H), 3.27 (s, 3H), 2.31 (s, 3H). LCMS (ES$^+$) 315.0 (M+H)$^+$, RT 1.02 minutes.

Intermediate 6

4-Chloro-3-methyl-6-[4-(methylsulfonyl)phenyl]cinnoline

A solution of Intermediate 5 (200 mg, 0.64 mmol) in phosphorus trichloride (1.48 mL, 15.9 mmol) was heated at 100° C. for 2 h. The reaction mixture was poured onto ice (20 mL) and the pH was adjusted to ca. pH 5 by the addition of 6M aqueous sodium hydroxide solution, then the mixture was extracted with EtOAc (3×20 mL). The combined organic layers were washed with brine (20 mL), then dried (Na$_2$SO$_4$) and concentrated in vacuo, yielding the title compound (223 mg, quantitative) as a dark purple solid, which was used without further purification. $\delta_H$ (500 MHz, DMSO-d$_6$) 8.67 (d, J 9.0 Hz, 1H), 8.45 (s, 1H), 8.39 (d, J 9.0 Hz, 1H), 8.27-8.08 (m, 4H), 3.02 (s, 3H). LCMS (ES$^+$) 332.9/334.8 (M+H)$^+$, RT 1.16 minutes.

Intermediates 7 & 8

6-Bromo-4-chloro-3-methylcinnoline and 4,6-Dichloro-3-methylcinnoline

A solution of Intermediate 4 (400 mg, 1.57 mmol) in phosphorus trichloride (2.49 mL, 26.7 mmol) was heated at 100° C. for 2 h. The reaction mixture was poured onto ice (20 mL) and the pH was adjusted to ca. pH 5 by the addition of 6M aqueous sodium hydroxide solution, then the mixture was extracted with EtOAc (3×20 mL). The combined organic layers were washed with brine (20 mL), then dried (Na$_2$SO$_4$) and concentrated in vacuo, yielding a 65:35 inseparable mixture of the title compounds (366 mg, 59%) as a grey solid, which was used without further purification. $\delta_H$ (500 MHz, DMSO-d$_6$) 8.46 (d, J 9.0 Hz, 1H), 8.37 (d, J 2.0 Hz, 1H), 8.12 (dd, J 9.0, 2.0 Hz, 1H), 2.98 (s, 3H). LCMS (ES$^+$) 256.8/258.0 (M+H)$^+$, RT 1.28 minutes; and 212.9/214.9 (M+H)$^+$ RT 1.25 minutes.

Intermediate 9

2-[5-(4-Chloro-3-methylcinnolin-6-yl)pyrimidin-2-yl]propan-2-ol

A solution of a 65:35 mixture of Intermediates 7 and 8 (366 mg, 0.92 mmol) and 2-[5-(4,4,5,5-tetramethyl-1,3,2-dioxaborolan-2-yl)pyrimidin-2-yl]propan-2-ol (245 mg, 0.93 mmol) in 1,4-dioxane (10 mL) and 2M aqueous potassium carbonate solution (1.39 mL, 2.78 mmol) was degassed for 10 minutes under a stream of nitrogen prior to the addition of Pd(dppf)Cl$_2$.DCM (38 mg, 0.05 mmol). The reaction mixture was heated at 70° C. for 2 h. The reaction mixture was cooled to r.t, diluted with water (25 mL) and extracted with DCM (3×25 mL). The combined organic layers were dried (Na$_2$SO$_4$) and concentrated in vacuo. The residue was purified by flash column chromatography (SiO$_2$, 0-100% EtOAc/heptane), yielding the title compound (223 mg, 77%) as a yellow solid. $\delta_H$ (500 MHz, DMSO-d$_6$) 9.37 (s, 2H), 8.67 (d, J 9.0 Hz, 1H), 8.54 (d, J 2.0 Hz, 1H), 8.43 (dd, J 9.0, 2.0 Hz, 1H), 5.19 (s, 1H), 3.01 (s, 3H), 1.58 (s, 6H). LCMS (ES$^+$) 315.0/317.0 (M+H)$^+$, RT 1.08 minutes.

Intermediate 10

6-Chloro-3-methyl-4-(2-methylphenoxy)cinnoline

To a cooled (0° C.) solution of 2-methylphenol (44 μL, 0.43 mmol) in DMF (3 mL) was added sodium hydride (60% suspension in mineral oil, 20 mg, 0.51 mmol). The reaction mixture was stirred at 0° C. for 15 minutes, prior to the addition of Intermediate 8 (90 mg, 0.39 mmol) in DMF (1 mL). The reaction mixture was stirred at r.t. for 5 h, then quenched by the addition of water (5 mL), further diluted with water (20 mL) and extracted with EtOAc (3×25 mL). The combined organic layers were washed with brine (30 mL), dried (Na$_2$SO$_4$) and concentrated in vacuo. The resultant crude material was purified by flash column chromatography (SiO$_2$, 0-50% EtOAc/heptane), yielding the title compound (91 mg, 77%) as a pale yellow solid. $\delta_H$ (250 MHz, CDCl$_3$) 8.50 (d, J 9.0 Hz, 1H), 7.88 (d, J 2.0 Hz, 1H), 7.72 (dd, J 9.0, 2.0 Hz, 1H), 7.40-7.30 (m, 1H), 7.10-6.94 (m, 2H), 6.23-6.11 (m, 1H), 2.70 (s, 3H), 2.53 (s, 3H). LCMS (ES$^+$) 284.9/287.0 (M+H)$^+$, RT 1.45 minutes.

Intermediate 11

2-Chloro-4-[4-(methanesulfonyl)phenyl]benzaldehyde

A mixture of 4-bromo-2-chlorobenzaldehyde (5.00 g, 22.8 mmol) and 4-(methanesulfonylphenyl)boronic acid (4.56 g, 22.8 mmol) in 1,4-dioxane (100 mL) and 2M aqueous sodium carbonate solution (34.6 mL, 69.2 mmol) was degassed for 10 minutes under a stream of nitrogen prior to the addition of Pd(dppf)Cl$_2$.DCM (930 mg, 1.14 mmol). The reaction mixture was heated at 80° C. for 2 h. The reaction mixture was cooled to r.t., diluted with water (50 mL) and extracted with EtOAc (3×50 mL). The combined organic layers were washed with brine (50 mL), dried (MgSO$_4$) and concentrated in vacuo. The resulting material was purified by flash column chromatography (SiO$_2$, 30-100% EtOAc/heptane), yielding the title compound (4.0 g, 58%) as an orange solid. $\delta_H$ (500 MHz, CDCl$_3$) 10.53 (d, J 1.0 Hz, 1H), 8.09-8.02 (m, 3H), 7.82-7.78 (m, 2H), 7.70 (d, J 1.5 Hz, 1H), 7.64-7.61 (m, 1H), 3.11 (s, 3H).

Intermediate 12

4-[4-(Methylsulfonyl)phenyl]-2-(prop-1-ynyl)benzaldehyde

A solution of Intermediate 11 (2.61 g, 8.77 mmol) in toluene (60 mL) was degassed for 10 minutes under a stream of nitrogen prior to the addition of tetrakis-(triphenylphosphine)palladium(0) (486 mg, 0.42 mmol), followed by tributyl(1-propynyl)tin (4.00 mL, 13.2 mmol). The reaction mixture was heated at 110° C. for 5 h. The reaction mixture was cooled to r.t., then poured into saturated aqueous potassium fluoride solution (100 mL) and extracted with EtOAc (3×75 mL). The combined organic layers were washed with brine (75 mL), dried (MgSO$_4$) and concentrated in vacuo. The residue was purified by flash column chromatography (SiO$_2$, 20-100% EtOAc/heptane), yielding the title compound (3.06 g, 52%) as an off-white solid. $\delta_H$ (500 MHz, CDCl$_3$) 10.56 (d, J 1.0 Hz, 1H), 8.07-8.03 (m, 2H), 8.00 (d, J 8.0 Hz, 1H), 7.82-7.78 (m, 2H), 7.75 (d, J 2.0 Hz, 1H), 7.62 (dd, J 8.0, 1.0 Hz, 1H), 3.11 (s, 3H), 2.17 (s, 3H). LCMS (ES$^+$) 299.0 (M+H)$^+$, RT 1.63 minutes.

Intermediate 13

{4-[4-(Methylsulfonyl)phenyl]-2-(prop-1-ynyl)phenyl}methanol

To a cooled (0° C.) suspension of Intermediate 12 (2.56 g, 8.58 mmol) in THF (30 mL) and MeOH (30 mL) was added sodium borohydride (649 mg, 17.2 mmol) portionwise. The reaction mixture was allowed to warm to r.t. over 1 h, then quenched with water (15 mL). The organic solvents were removed in vacuo. The resultant mixture was extracted with EtOAc (3×15 mL). The combined organic layers were washed with water (15 mL), then dried (MgSO$_4$) and concentrated in vacuo, yielding the title compound (2.59 g, 85%) as an off-white solid, which was used without further purification. $\delta_H$ (500 MHz, CDCl$_3$) 8.02-7.98 (m, 2H), 7.77-7.74 (m, 2H), 7.66 (s, 1H), 7.55-7.51 (m, 2H), 4.86 (d, J 6.5 Hz, 2H), 3.09 (s, 3H), 2.13 (s, 3H).

Intermediate 14

1-(Azidomethyl)-4-[4-(methanesulfonyl)phenyl]-2-(prop-1-yn-1-yl)benzene

To a solution of Intermediate 13 (2.59 g, 6.9 mmol) in toluene (50 mL) was added 1,8-diazabicyclo[5.4.0]undec-7-ene (1.55 mL, 10.3 mmol), followed by diphenyl phosphoryl azide (1.94 mL, 8.9 mmol). The reaction mixture was stirred at r.t. for 18 h. The reaction mixture was quenched by the addition of saturated aqueous ammonium chloride solution (20 mL), then extracted with EtOAc (3×50 mL). The combined organic layers were washed with water (30 mL), dried (MgSO$_4$) and concentrated in vacuo. The residue was purified by flash column chromatography (SiO$_2$, 10-100% EtOAc/heptane), yielding the title compound (1.79 g, 79%) as a yellow solid. $\delta_H$ (500 MHz, CDCl$_3$) 8.03-7.99 (m, 2H), 7.78-7.74 (m, 2H), 7.69 (d, J 2.0 Hz, 1H), 7.55-7.52 (m, 1H), 7.46 (d, J 8.0 Hz, 1H), 4.58 (s, 2H), 3.10 (s, 3H), 2.14 (s, 3H).

Intermediate 15

4-Iodo-3-methyl-6-[4-(methylsulfonyl)phenyl]isoquinoline

To a cooled (−78° C.) solution of Barluenga's Reagent (4.13 g, 10.8 mmol) in DCM (65 mL) was added tetrafluoroboric acid diethyl ether complex (2.93 mL, 10.8 mmol). The resultant solution was added slowly to a cooled (−78° C.) solution of Intermediate 14 (1.79 g, 5.4 mmol) in DCM (5 mL) and the reaction mixture was stirred at −78° C. for 1 h. The reaction mixture was quenched with saturated aqueous sodium thiosulfate solution (50 mL), then extracted with EtOAc (3×50 mL). The combined organic layers were washed with water (30 mL), dried (MgSO$_4$) and concentrated in vacuo. The residue was purified by flash column chromatography (SiO$_2$, 20-100% EtOAc/heptane), yielding the title compound (1.48 g, 64%) as a purple-brown solid. $\delta_H$ (500 MHz, CDCl$_3$) 9.09 (s, 1H), 8.30 (s, 1H), 8.13-8.10 (m, 2H), 8.01 (d, J 8.5 Hz, 1H), 7.95-7.92 (m, 2H), 7.83 (dd, J 8.5, 1.5 Hz, 1H), 3.13 (s, 3H), 3.03 (s, 3H). LCMS (ES$^+$) 424.0 (M+H)$^+$, RT 1.29 minutes.

Example 1 (Method A)

4-(2-Methoxybenzyl)-2-methylquinazoline

To a solution of 4-chloro-2-methylquinazoline (100 mg, 0.56 mmol) and tetrakis-(triphenylphosphine)palladium(0) (32 mg, 0.03 mmol) in THF (7 mL) was added 2-methoxybenzylzinc chloride (0.5M in THF, 2.02 mL, 1.01 mmol) dropwise over 5 minutes. The reaction mixture was heated at 50° C. for 18 h, then cooled to r.t. and quenched with saturated aqueous ammonium chloride solution (2 mL). The organic solvent was removed in vacuo. The residue was taken up in water (30 mL) and extracted with DCM (2×30 mL). The combined organic layers were dried (Na$_2$SO$_4$) and concentrated in vacuo. The residue was purified by flash column chromatography (SiO$_2$, 0-100% EtOAc/heptane), yielding the title compound (95 mg, 64%) as a yellow solid. $\delta_H$ (500 MHz, CDCl$_3$) 8.13 (d, J 8.0 Hz, 1H), 8.01-7.88 (m, 1H), 7.79 (t, J 7.5 Hz, 1H), 7.47 (t, J 7.5 Hz, 1H), 7.23-7.16 (m, 1H), 7.01 (d, J 7.0 Hz, 1H), 6.90 (d, J 8.0 Hz, 1H), 6.81 (t, J 7.5 Hz, 1H), 4.59 (s, 2H), 3.90 (s, 3H), 2.89 (s, 3H). LCMS (ES$^+$) 265.0 (M+H)$^+$, RT 1.45 minutes.

Example 2

3-(2-Methoxybenzyl)quinoline

Prepared from 3-bromoquinoline (65 μL, 0.48 mmol), tetrakis(triphenyl-phosphine)palladium(0) (28 mg, 0.02 mmol) and 2-methoxybenzylzinc chloride (0.5M in THF, 1.73 mL, 0.87 mmol) in THF (7 mL) by Method A to give the title compound (29 mg, 24%). $\delta_H$ (500 MHz, CDCl$_3$) 8.88 (s, 1H), 8.09 (d, J 8.5 Hz, 1H), 7.91 (s, 1H), 7.73 (d, J 8.5 Hz, 1H), 7.67-7.63 (m, 1H), 7.53-7.48 (m, 1H), 7.25-7.22 (m, 1H), 7.17 (dd, J 7.5, 1.5 Hz, 1H), 6.94-6.87 (m, 2H), 4.15 (s, 2H), 3.81 (s, 3H). LCMS (ES$^+$) 250.1 (M+H)$^+$, RT 1.59 minutes.

Example 3

4-(2-Methoxybenzyl)quinazoline

Prepared from 4-chloroquinazoline (100 mg, 0.61 mmol), tetrakis(triphenyl-phosphine)palladium(0) (35 mg, 0.03 mmol) and 2-methoxybenzylzinc chloride (0.5M in THF, 2.19 mL, 1.10 mmol) in THF (7 mL) by Method A to give the title compound (70 mg, 44%). $\delta_H$ (500 MHz, CDCl$_3$) 9.24 (s, 1H), 8.24 (d, J 8.5 Hz, 1H), 8.03 (d, J 8.5 Hz, 1H), 7.86 (ddd, J 8.5, 7.0, 1.5 Hz, 1H), 7.59 (ddd, J 8.5, 7.0, 1.0 Hz, 1H), 7.22 (td, J 8.0, 2.0 Hz, 1H), 7.11 (dd, J 7.5, 1.5 Hz, 1H), 6.93-6.84 (m, 2H), 4.63 (s, 2H), 3.84 (s, 3H). LCMS (ES$^+$) 251.0 (M+H)$^+$. RT 1.43 minutes.

Example 4

2-(2-Chlorophenoxy)-3-methylquinoxaline

A mixture of 2-chloro-3-methylquinoxaline (100 mg, 0.56 mmol), 2-chlorophenol (144 mg, 1.12 mmol) and potassium carbonate (929 mg, 6.72 mmol) in DMSO (5.6 mL) was heated at 120° C. in a sealed tube for 18 h. The reaction mixture was partitioned between EtOAc (60 mL) and water (60 mL). The organic layer was separated and the aqueous layer was back-extracted with 10% propan-2-ol in chloroform (2×60 mL). The combined organic layers were dried (Na$_2$SO$_4$) and concentrated in vacuo. The residue was purified by flash column chromatography (SiO$_2$, 0-100% EtOAc/heptane, followed by 1-100% MeOH/EtOAc), then repurified by preparative HPLC, yielding the title compound (37.5 mg, 24%) as an off-white solid. $\delta_H$ (500 MHz, DMSO-d$_6$) 8.03-7.99 (m, 1H), 7.73-7.58 (m, 4H), 7.56-7.45 (m, 2H), 7.44-7.35 (m, 1H), 2.80 (s, 3H). LCMS (ES$^+$) 271.0/273.0 (M+H)$^+$, RT 1.69 minutes.

Example 5

2-[(2-Methoxyphenyl)methyl]-3-methylquinoxaline

Prepared from 2-chloro-3-methylquinoxaline (100 mg, 0.56 mmol), tetrakis-(triphenylphosphine)palladium(0) (32 mg, 0.03 mmol) and 2-methoxybenzylzinc chloride (0.5M in THF, 2.02 mL, 1.01 mmol) in THF (8 mL) by Method A to give the title compound (52 mg, 35%). $\delta_H$ (500 MHz, DMSO-d$_6$) 8.01-7.92 (m, 2H), 7.78-7.69 (m, 2H), 7.24 (td, J 8.0, 2.0 Hz, 1H), 7.03 (d, J 7.5 Hz, 1H), 6.92 (dd, J 7.5, 2.0 Hz, 1H), 6.85 (td, J 7.5, 1.0 Hz, 1H), 4.31 (s, 2H), 3.78 (s, 3H), 2.64 (s, 3H). LCMS (ES$^+$) 265.0 (M+H)$^+$ RT 1.55 minutes.

Example 6

3-Methyl-6-[4-(methylsulfonyl)phenyl]-4-(1-phenylethyl)cinnoline

Prepared from Intermediate 6 (117 mg, 0.35 mmol), tetrakis(triphenylphosphine)-palladium(0) (81 mg, 0.07 mmol) and 1-phenylethylzinc chloride (0.5M in THF, 1.27 mL, 0.64 mmol) in THF (10 mL) by Method A to give the title compound (32 mg, 41%). $\delta_H$ (500 MHz, CDCl$_3$) 8.58 (d, J 9.5 Hz, 1H), 8.01-7.95 (m, 2H), 7.91-7.84 (m, 2H), 7.51-7.45 (m, 2H), 7.38-7.34 (m, 2H), 7.31-7.28 (m, 1H), 7.25-7.23 (m, 2H), 4.99 (q, J 7.0 Hz, 1H), 3.10 (s, 3H), 3.04 (s, 3H), 1.87 (d, J 7.0 Hz, 3H). LCMS (ES$^+$) 403.0 (M+H)$^+$, RT 1.48 minutes.

Example 7

4-[2-(Difluoromethoxy)benzyl]-3-methyl-6-[4-(methylsulfonyl)phenyl]cinnoline

A mixture of Intermediate 6 (50 mg, 0.14 mmol) and 2-{[2-(difluoromethoxy)-phenyl]methyl}-4,4,5,5-tetramethyl-1,3,2-dioxaborolane (64 mg, 0.21 mmol) in 1,4-dioxane (2 mL) and 2M aqueous potassium carbonate solution (214 µL, 0.43 mmol) was degassed for 10 minutes under a stream of nitrogen prior to the addition of Pd(dppf)Cl$_2$.DCM (12 mg, 0.01 mmol). The reaction mixture was heated in a sealed tube at 100° C. for 24 h. After this time, the reaction had not gone to completion so further 2-{[2-(difluoromethoxy)phenyl]methyl}-4,4,5,5-tetramethyl-1,3,2-dioxaborolane (64 mg, 0.21 mmol), 2M aqueous potassium carbonate solution (100 µL, 0.20 mmol) and Pd(dppf)Cl$_2$.DCM (12 mg, 0.01 mmol) were added. The reaction mixture was heated at 100° C. for 3 h, then diluted with water (20 mL) and extracted with EtOAc (3×25 mL). The combined organic layers were washed with brine (30 mL), dried (Na$_2$SO$_4$) and concentrated in vacuo. The residue was purified by flash column chromatography (SiO$_2$, 0-100% EtOAc/heptane), then repurified by preparative HPLC, yielding the title compound (9 mg, 15%) as a pale yellow solid. $\delta_H$ (500 MHz, CDCl$_3$) 8.64 (d, J 9.0 Hz, 1H), 8.08-8.02 (m, 3H), 7.99 (dd, J 8.5, 1.7 Hz, 1H), 7.79 (d, J 8.5 Hz, 2H), 7.27-7.19 (m, 2H), 7.00 (t, J 7.5 Hz, 1H), 6.69 (t, J 75.0 Hz, 1H), 6.60 (d, J 8.0 Hz, 1H), 4.53 (s, 2H), 3.10 (s, 3H), 2.97 (s, 3H). LCMS (ES$^+$) 455.0 (M+H)$^+$, RT 1.47 minutes.

Example 8

2-{5-[3-Methyl-4-(1-phenylethyl)cinnolin-6-yl]pyrimidin-2-yl}propan-2-ol

Prepared from Intermediate 9 (93 mg, 0.30 mmol), tetrakis(triphenylphosphine)-palladium(0) (68 mg, 0.06 mmol) and 1-phenylethylzinc chloride (0.5M in THF, 1.06 mL, 0.53 mmol) in THF (10 mL) by Method A to give the title compound (17 mg, 15%). $\delta_H$ (500 MHz, CDCl$_3$) 8.66 (s, 2H), 8.62 (d, J 9.0 Hz, 1H), 7.88-7.82 (m, 2H), 7.38-7.35 (m, 2H), 7.32-7.29 (m, 1H), 7.24-7.22 (m, 2H), 4.99 (q, J 7.5 Hz, 1H), 4.56 (s, 1H), 3.06 (s, 3H), 1.89 (d, J 7.5 Hz, 3H), 1.64 (s, 6H). LCMS (ES$^+$) 385.0 (M+H)$^+$, RT 1.43 minutes.

Example 9

2-(5-{4-[2-(Difluoromethoxy)benzyl]-3-methylcinnolin-6-yl}pyrimidin-2-yl)propan-2-ol A mixture of Intermediate 9 (80 mg, 0.25 mmol) and 2-{[2-(difluoromethoxy)-phenyl]methyl}-4,4,5,5-tetramethyl-1,3,2-dioxaborolane (152 mg, 0.51 mmol) in 1,4-dioxane (5 mL) and 2M aqueous potassium carbonate solution (381 pt, 0.76 mmol) was degassed for 10 minutes under a stream of nitrogen prior to the addition of Pd(dppf)Cl$_2$.DCM (10 mg, 0.01 mmol). The reaction mixture was heated in a sealed tube at 100° C. for 6 h. After this time, the reaction had not gone to completion so further 2-{[2-(difluoromethoxy)phenyl]methyl}-4,4,5,5-tetramethyl-1,3,2-dioxaborolane (152 mg, 0.51 mmol) in 1,4-dioxane (1 mL), 2M aqueous potassium carbonate solution (381 pt, 0.76 mmol) and Pd(dppf)Cl$_2$.DCM (10 mg, 0.01 mmol) were added. The reaction mixture was heated in a sealed tube at 100° C. for 18 h. The reaction mixture was cooled to r.t., diluted with water (10 mL) and brine (10 mL), then extracted with DCM (3×20 mL). The combined organic layers were dried (Na$_2$SO$_4$) and concentrated in vacuo. The residue was purified by flash column chromatography (SiO$_2$, 20-100% EtOAc/heptane), then repurified by preparative HPLC, yielding the title compound (24 mg, 24%) as a pale yellow solid. $\delta_H$ (500 MHz, CDCl$_3$) 8.94 (s, 2H), 8.69 (d, J 9.0 Hz, 1H), 8.03 (d, J 1.5 Hz, 1H), 7.96 (dd, J 9.0, 1.5 Hz, 1H), 7.28-7.20 (m, 2H), 7.00 (t, J 7.5 Hz, 1H), 6.69 (t, J 75.0 Hz, 1H), 6.58 (d, J 7.5 Hz, 1H), 4.56 (s, 1H), 4.53 (s, 2H), 2.98 (s, 3H), 1.65 (s, 6H). LCMS (ES$^+$) 437.0 (M+H)$^+$, RT 1.42 minutes.

Example 10

2-{5-[3-Methyl-4-(2-methylphenoxy)cinnolin-6-yl]pyrimidin-2-yl}propan-2-ol

A mixture of Intermediate 10 (90 mg, 0.32 mmol) and 2-[5-(4,4,5,5-tetramethyl-1,3,2-dioxaborolan-2-yl)pyrimidin-2-yl]propan-2-ol (100 mg, 0.38 mmol) in 1,4-dioxane (4 mL) and 2M aqueous potassium carbonate solution (474 µl, 0.95 mmol) was degassed for 10 minutes under a stream of nitrogen prior to the addition of Pd(dppf)Cl$_2$.DCM (13 mg, 0.02 mmol). The reaction mixture was heated at 100° C. in a sealed tube for 2 h. After this time, the reaction had not gone to completion so further 2-[5-(4,4,5,5-tetramethyl-1,3,2-dioxaborolan-2-yl)pyrimidin-2-yl]propan-2-ol (50 mg, 0.19 mmol) was added and the reaction mixture was heated at 100° C. in a sealed tube for 2 h. The reaction mixture was cooled to r.t, then diluted with water (20 mL) and extracted with EtOAc (20 mL). The organic layer was separated and the aqueous layer was back-extracted with EtOAc (2×20 mL). The combined organic layers were washed with brine (20 mL), dried (Na$_2$SO$_4$) and concentrated in vacuo. The residue was purified by flash column chromatography (SiO$_2$, 0-100% EtOAc/heptane), then repurified by preparative HPLC, yielding the title compound (56 mg, 46%) as a yellow solid. $\delta_H$ (500 MHz, CDCl$_3$) 8.94 (s, 2H), 8.71 (d, J 9.0 Hz, 1H), 8.04 (d, J 2.0 Hz, 1H), 7.99 (dd, J 9.0, 2.0 Hz, 1H), 7.34 (d, J 7.0 Hz, 1H), 7.07-6.96 (m, 2H), 6.22 (d, J 8.0 Hz, 1H), 4.55 (s, 1H), 2.75 (s, 3H), 2.54 (s, 3H), 1.64 (s, 6H). LCMS (ES$^+$) 387.0 (M+H)$^+$, RT 1.48 minutes.

Example 11

4-[2-(Difluoromethoxy)benzyl]-3-methyl-6-[4-(methylsulfonyl)phenyl]isoquinoline

A mixture of Intermediate 15 (70 mg, 0.16 mmol) and 2-{[2-(difluoromethoxy)-phenyl]methyl}-4,4,5,5-tetramethyl-1,3,2-dioxaborolane (95 mg, 0.32 mmol) in 1,4-dioxane (5 mL) and 2M aqueous potassium carbonate solution (238 µL, 0.48 mmol) was degassed for 10 minutes under a stream of nitrogen prior to the addition of Pd(dppf)Cl$_2$.DCM (6 mg, 0.01 mmol). The reaction mixture was heated in a sealed tube at 100° C. for 3 h. After this time, the reaction had not gone to completion so further 2-{[2-(difluoromethoxy)phenyl]methyl}-4,4,5,5-tetramethyl-1,3,2-dioxaborolane (95 mg, 0.32 mmol) was added and the mixture was stirred at 100° C. for 1.5 h. To push the reaction to completion, further 2-{[2-(difluoromethoxy)phenyl]methyl}-4,4,5,5-tetramethyl-1,3,2-dioxaborolane (95 mg, 0.32 mmol), 2M aqueous potassium carbonate solution (238 µL, 0.48 mmol) and Pd(dppf)Cl$_2$.DCM (6 mg, 0.01 mmol) were added and the mixture was stirred at 100° C. for 18 h. Further 2-{[2-(difluoromethoxy)phenyl]-methyl}-4,4,5,5-tetramethyl-1,3,2-dioxaborolane (95 mg, 0.32 mmol), 2M aqueous potassium carbonate solution (238 µL, 0.48 mmol) and Pd(dppf)Cl$_2$.DCM (6 mg, 0.01 mmol) were added and the mixture was stirred at 100° C. for 2 h. The reaction mixture was cooled to r.t., diluted with water (10 mL) and brine (10 mL), then extracted with DCM (3×20 mL). The combined organic layers were dried (Na$_2$SO$_4$) and concentrated in vacuo. The residue was purified by flash column chromatography (SiO$_2$, 30-100% EtOAc/heptane), then repurified by preparative HPLC, yielding the title compound (19 mg, 29%) as an off-white solid. $\delta_H$ (500 MHz, CDCl$_3$) 9.22 (s, 1H), 8.09 (d, J 8.5 Hz, 1H), 8.04-7.98 (m, 3H), 7.78-7.74 (m, 3H), 7.24-7.18 (m, 2H), 7.00-6.95 (m, 1H), 6.70 (t, J 74.0 Hz, 1H), 6.64 (d, J 7.5 Hz, 1H), 4.51 (s, 2H), 3.09 (s, 3H), 2.73 (s, 3H). LCMS (ES$^+$) 454.0 (M+H)$^+$, RT 1.52 minutes.

Example 12

3-Methyl-6-[4-(methylsulfonyl)phenyl]-4-(1-phenylethyl)isoquinoline

Prepared from Intermediate 15 (200 mg, 0.47 mmol), tetrakis(triphenyl-phosphine)palladium(0) (109 mg, 0.09 mmol) and 1-phenylethylzinc chloride (0.5M in THF, 1.70 mL, 0.85 mmol) in THF (10 mL) by Method A to give the title compound (31 mg, 28%). $\delta_H$ (500 MHz, CDCl$_3$) 9.14 (s, 1H), 8.01 (d, J 8.5 Hz, 1H), 7.97-7.93 (m, 2H), 7.85 (s, 1H), 7.65 (dd, J 8.5, 1.5 Hz, 1H), 7.44-7.41 (m, 2H), 7.36-7.32 (m, 2H), 7.30-7.26 (m, 3H), 5.03 (q, J 7.0 Hz, 1H), 3.09 (s, 3H), 2.82 (s, 3H), 1.86 (d, J 7.0 Hz, 3H). LCMS (ES$^+$) 402.0 (M+H)$^+$, RT 1.55 minutes.

The invention claimed is:
1. A compound represented by formula (IIB), or a pharmaceutically acceptable salt thereof:

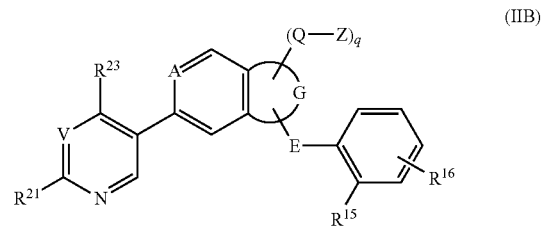

wherein
V represents C—R$^{22}$ or N;
R$^{21}$ represents hydroxy(C$_{1-6}$)alkyl or R$^{21}$ represents (C$_{3-7}$)cycloalkyl, which group is optionally substituted by one, two, or three substituents independently selected from halogen, halo(C$_{1-6}$)alkyl, cyano, C$_{1-6}$ alkyl, trifluoromethyl, hydroxy, hydroxy(C$_{1-6}$)alkyl, C$_{1-6}$ alkoxy, C$_{1-6}$ alkylthio, C$_{1-6}$ alkylsulphinyl, C$_{1-6}$ alkylsulphonyl, amino, C$_{1-6}$ alkylamino, di(C$_{1-6}$)alkylamino, C$_{2-6}$ alkylcarbonylamino, (C$_{2-6}$)alkylcarbonylamino(C$_{1-6}$)alkyl, C$_{2-6}$ alkoxycarbonylamino, (C$_{2-6}$)alkoxycarbonylamino-(C$_{1-6}$)alkyl, C$_{1-6}$ alkyl sulphonylamino, (C$_{1-6}$)alkyl-sulphonylamino(C$_{1-6}$)alkyl, formyl, $C_{2-6}$ alkylcarbonyl, carboxy, carboxy($C_{1-6}$)alkyl, $C_{2-6}$ alkoxycarbonyl, $C_{2-6}$ alkoxycarbonyl($C_{1-6}$)alkyl, aminosulphonyl, ($C_{1-6}$)alkylsulphoximinyl, [($C_{1-6}$)alkyl][N—($C_{1-6}$)alkyl]sulphoximinyl, ($C_{1-6}$)alkylsulphonylaminocarbonyl, ($C_{2-6}$)alkylcarbonyl-aminosulphonyl, ($C_{1-6}$)alkoxyaminocarbonyl, tetrazolyl and hydroxyoxadiazolyl;

$R^{22}$ represents hydrogen, halogen or $C_{1-6}$ alkyl;

$R^{23}$ represents hydrogen, $C_{1-6}$ alkyl, trifluoromethyl or $C_{1-6}$ alkoxy;

q is zero or 1;

A represents C—$R^2$ or N;

G represents the residue of a six-membered heteroaromatic ring selected from pyridinyl, pyridazinyl, pyrimidinyl, and pyrazinyl;

E represents —O—, —CH$_2$—, or —CH(CH$_3$);

Q represents —CH$_2$— or —CH$_2$O;

Z represents hydrogen or methyl;

$R^2$ represents hydrogen or halogen;

$R^{15}$ represents hydrogen, halogen, $C_{1-6}$ alkyl, $C_{1-6}$ alkoxy or difluoromethoxy; and $R^{16}$ represents hydrogen, halogen, cyano, $C_{1-6}$ alkyl, trifluoromethyl, difluoromethoxy or amino.

2. The compound as claimed in claim 1 wherein $R^{21}$ represents hydroxy($C_{1-6}$)alkyl.

3. The compound as claimed in claim 1 represented by formula (IIF), (IIG), (IIH), or (IIJ), or a pharmaceutically acceptable salt thereof:

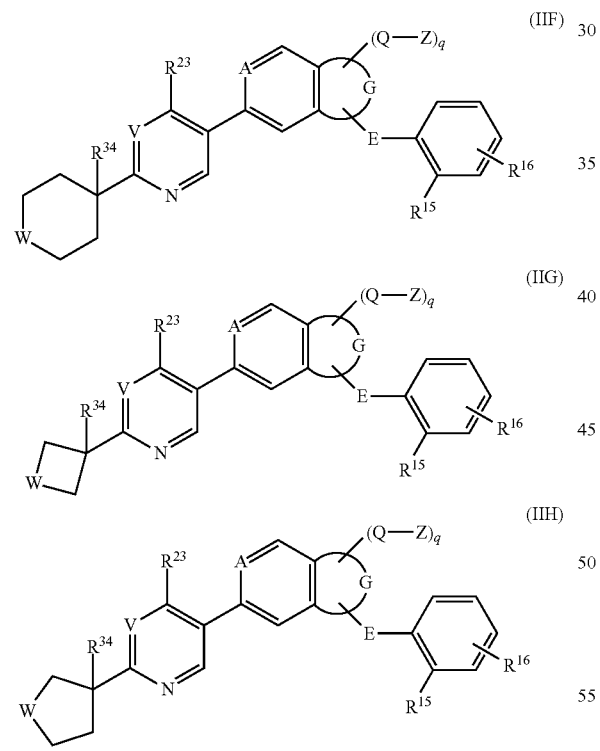

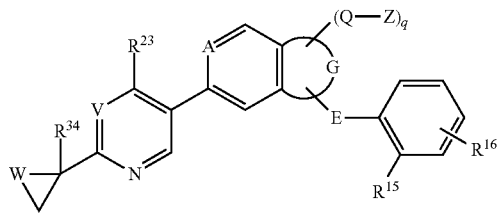

wherein

W represents $C(R^{32})(R^{33})$;

$R^{32}$ represents hydrogen, halogen, cyano, hydroxy, hydroxy($C_{1-6}$)alkyl, $C_{1-6}$ alkylsulphonyl, formyl, carboxy, carboxy($C_{1-6}$)alkyl, $C_{2-6}$ alkoxycarbonyl, $C_{2-6}$ alkoxycarbonyl($C_{1-6}$)alkyl, aminosulphonyl, ($C_{1-6}$)alkylsulphoximinyl, [($C_{1-6}$)alkyl][N—($C_{1-6}$)alkyl]sulphoximinyl, ($C_{1-6}$)alkylsulphonylaminocarbonyl, ($C_{2-6}$)alkylcarbonyl-aminosulphonyl, ($C_{1-6}$)alkoxyaminocarbonyl, tetrazolyl or hydroxyoxadiazolyl;

$R^{33}$ represents hydrogen, halogen, $C_{1-6}$ alkyl, trifluoromethyl, hydroxy, hydroxy-($C_{1-6}$)alkyl, $C_{1-6}$ alkoxy, amino or carboxy;

$R^{34}$ represents hydrogen, halogen, halo($C_{1-6}$)alkyl, hydroxy, $C_{1-6}$ alkoxy, $C_{1-6}$ alkylthio, $C_{1-6}$ alkylsulphinyl, $C_{1-6}$ alkylsulphonyl, amino, $C_{1-6}$ alkylamino, di($C_{1-6}$)alkyl-amino, ($C_{2-6}$)alkylcarbonylamino, ($C_{2-6}$)alkylcarbonylamino($C_{1-6}$)alkyl, ($C_{1-6}$)alkyl-sulphonylamino or ($C_{1-6}$)alkylsulphonylamino($C_{1-6}$)alkyl;

q is zero or 1.

4. The compound as claimed in claim 3 wherein $R^{34}$ represents hydrogen, fluoro or hydroxy.

5. The compound as claimed in claim 1 wherein $R^{15}$ represents difluoromethoxy.

6. A compound that is

2-{5-[3-Methyl-4-(1-phenylethyl)cinnolin-6-yl]pyrimidin-2-yl}propan-2-ol, 2-(5-{4-[2-(Difluoromethoxy)benzyl]-3-methylcinnolin-6-yl}pyrimidin-2-yl)propan-2-ol, or 2-{5-[3-Methyl-4-(2-methylphenoxy)cinnolin-6-yl]pyrimidin-2-yl}propan-2-ol.

7. A pharmaceutical composition comprising a compound of formula (IIB) as defined in claim 1 or a pharmaceutically acceptable salt thereof, in association with a pharmaceutically acceptable carrier.

8. The pharmaceutical composition as claimed in claim 7 further comprising an additional pharmaceutically active ingredient.

* * * * *